(12) United States Patent
Shimizu et al.

(10) Patent No.: US 7,732,784 B2
(45) Date of Patent: Jun. 8, 2010

(54) WAVELENGTH-TUNABLE LIGHT GENERATOR AND OPTICAL COHERENCE TOMOGRAPHY DEVICE

(75) Inventors: Kimiya Shimizu, Tokyo (JP); Kohji Ohbayashi, Chiba (JP); Takuji Amano, Tokyo (JP); Hideaki Hiro-Oka, Tokyo (JP); DongHak Choi, Kanagawa (JP); Hiroyuki Furukawa, Tokyo (JP); Motoi Nakanishi, Kanagawa (JP); Fumiyoshi Kano, Kanagawa (JP); Takeo Miyazawa, Kanagawa (JP); Ryoko Yoshimura, Kanagawa (JP)

(73) Assignee: School Juridical Person Kitasato Institute, Tokyo (JP)

( * ) Notice: Subject to any disclaimer, the term of this patent is extended or adjusted under 35 U.S.C. 154(b) by 99 days.

(21) Appl. No.: 11/867,732

(22) Filed: Oct. 5, 2007

(65) Prior Publication Data

US 2008/0031410 A1 Feb. 7, 2008

Related U.S. Application Data

(62) Division of application No. 10/573,113, filed as application No. PCT/JP2004/014302 on Sep. 22, 2004.

(30) Foreign Application Priority Data

| Sep. 26, 2003 | (JP) | ............................. 2003-335207 |
| Jul. 9, 2004 | (JP) | ............................. 2004-202956 |
| Jul. 9, 2004 | (JP) | ............................. 2004-202957 |

(51) Int. Cl.
*G01T 1/166* (2006.01)
*H01S 5/00* (2006.01)

(52) U.S. Cl. ......................... 250/393; 356/497; 356/479

(58) Field of Classification Search ............ 250/339.01, 250/339.05, 339.09, 393; 356/450, 498, 356/FOR. 107, 479, 497
See application file for complete search history.

(56) References Cited

U.S. PATENT DOCUMENTS 3,471,788 A 10/1969 Bickford et al.

(Continued)

FOREIGN PATENT DOCUMENTS

EP 0389453 A1 3/1990

(Continued)

OTHER PUBLICATIONS

Zuyuan, He et al., "Synthesized optical coherence object by use of a stepwise frequency-modulated tunable laser diode", Optics Letters, vol. 24, No. 21, Nov. 1, 1999, pp. 1502 to 1504.

(Continued)

*Primary Examiner*—David P Porta
*Assistant Examiner*—Mark R Gaworecki
(74) *Attorney, Agent, or Firm*—Volentine & Whitt, P.L.L.C.

(57) ABSTRACT

An OCT technique that permits tomographic observation of biological body parts that are difficult to restrain, and also provides a tomographic observation technique for the observation of a constrainable part that does not require constraint and thus removes a burden on the biological body. A wavelength-tunable light generator (wavelength-tunable light source) is employed as the light source of the optical coherence tomography device. The wavelength-tunable light generator has a wave number tunable range width of at least $4.7 \times 10^{-2}$ $\mu m^{-1}$ and an emitted-light frequency width of no more than 13 GHz, for example, and is capable of changing the wave number stepwise at wave number intervals of no more than $3.1 \times 10^{-4}$ $\mu m^{-1}$ and time intervals of no more than 530 μs.

10 Claims, 39 Drawing Sheets

U.S. PATENT DOCUMENTS

| | | | |
|---|---|---|---|
| 4,890,925 A | | 1/1990 | Kitamori et al. |
| 4,896,325 A | | 1/1990 | Coldren |
| 5,565,986 A | | 10/1996 | Knuttel |
| 5,994,690 A | * | 11/1999 | Kulkarni et al. ............ 250/216 |
| 6,134,003 A | * | 10/2000 | Tearney et al. ............ 356/479 |

FOREIGN PATENT DOCUMENTS

| | | | |
|---|---|---|---|
| JP | 63044149 A | * | 2/1988 |
| JP | 06-053616 | | 2/1994 |
| JP | 06-061578 | | 3/1994 |
| JP | 10-223971 | | 8/1998 |
| JP | 11-150324 A | | 6/1999 |
| JP | 2000-342589 A | | 12/2000 |
| JP | 2001-289785 A | | 10/2001 |
| JP | 2003516531 W | * | 5/2003 |
| JP | 2003-172690 A | | 6/2003 |
| WO | 01/42735 A1 | | 6/2001 |

OTHER PUBLICATIONS

Piao, Daqing et al., "Coherent artifacts in optical coherence tomography observation and cancellation", proceedings of the IEEE 27th Annual Northeast Bioengineering Conference, 2001, pp. 53 to 54.

Wang, Xiao-Jun et al., "Characterization of dentin and enamel by use of optical coherence tomography", Applied Optics, vol. 38, No. 10, Apr. 1, 1999, pp. 2092 to 2096.

Edited by Brett E. Bouma et al., Handbook of Optical Coherence tomography, (USA), Marcel Dekker Inc., 2002, p. 591 to 612.

Choi, Donghak, "Fast high-resolution OFDR-OCT with SGG-DBR laser", Twenty-eighth Optical symposium lecture proceedings, Corp, Applied Physics 'Subcommittee meeting, Optical Society of Japan, Jun. 19, 2003, pp. 39 to 40.

Teramura, Yuichi et al., Proceeding of 23rd Meeting on Lightwave Sensing Technology, Jun. 2, 1999, p. 39.

Handbook of Optical Coherence Tomography (edited by Brett E. Bouma, Guillermo J. Tearney), Nov. 15, 2001, pp. 364-367.

* cited by examiner

FIG. 1
(A)
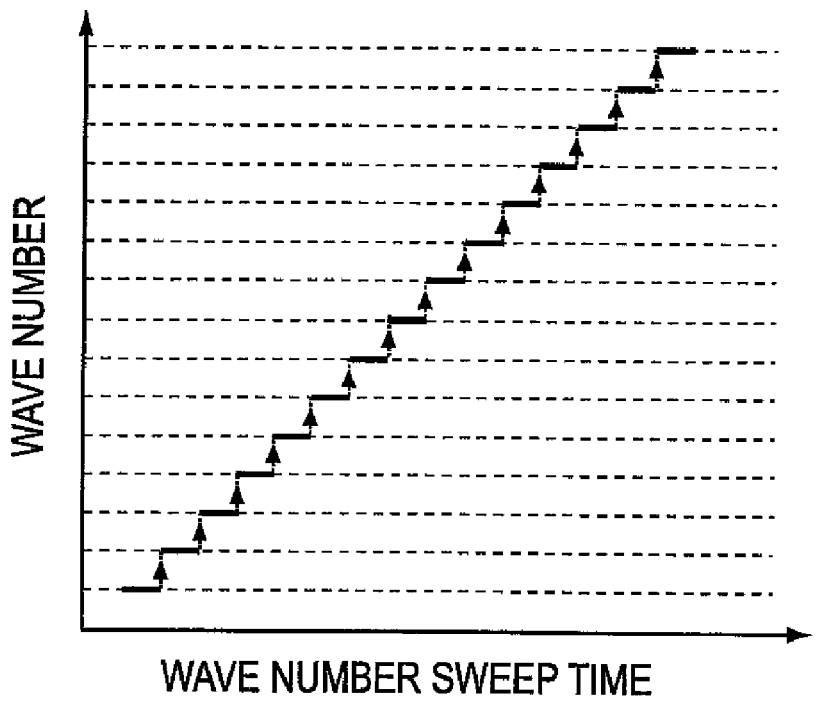
WAVE NUMBER SWEEP TIME
(B)
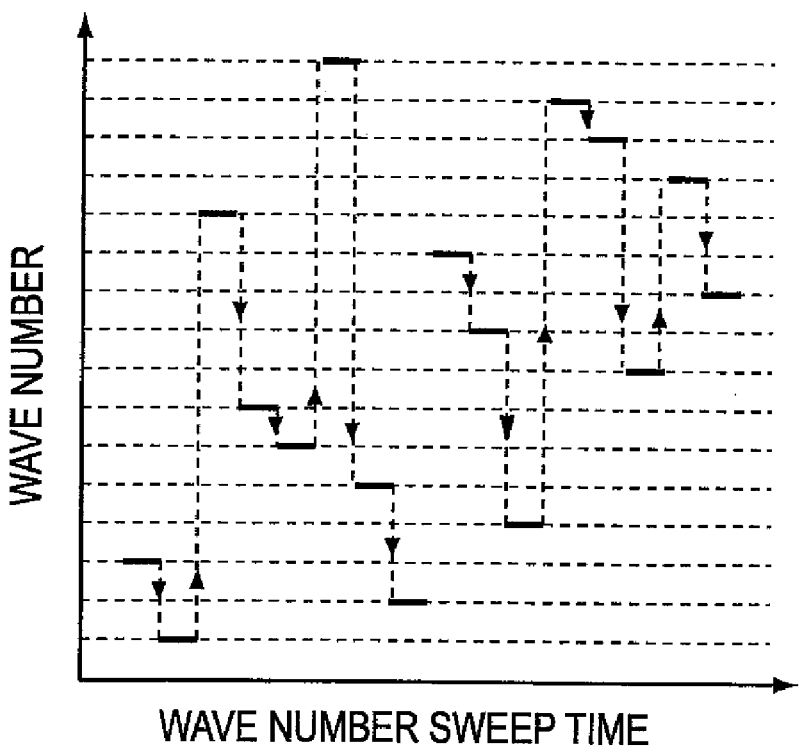
WAVE NUMBER SWEEP TIME

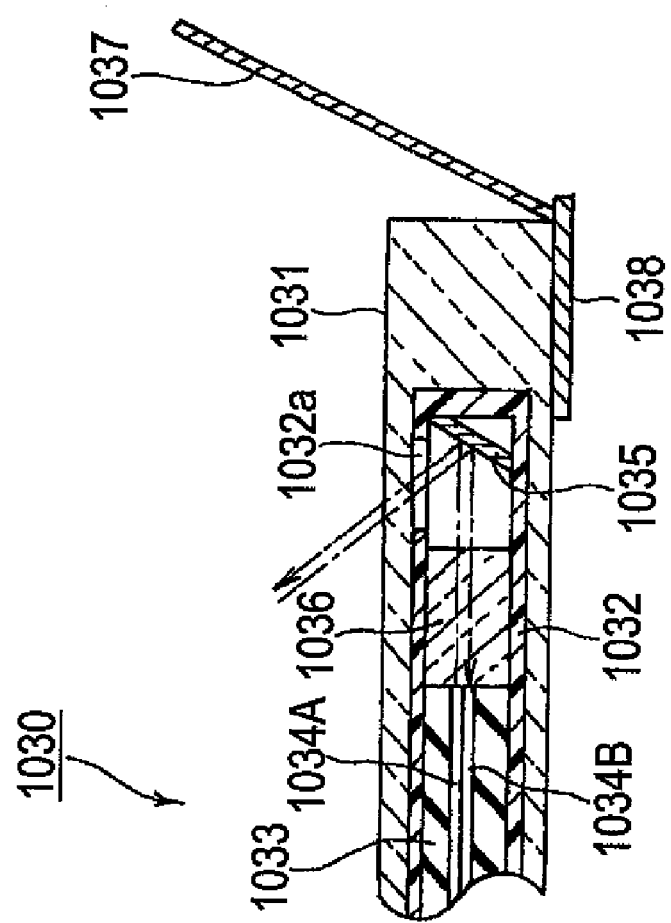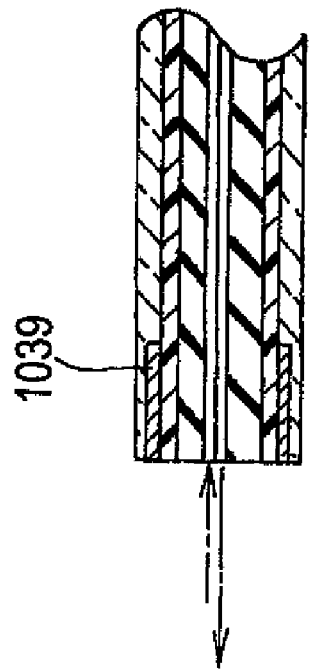
FIG.22

FIG.24
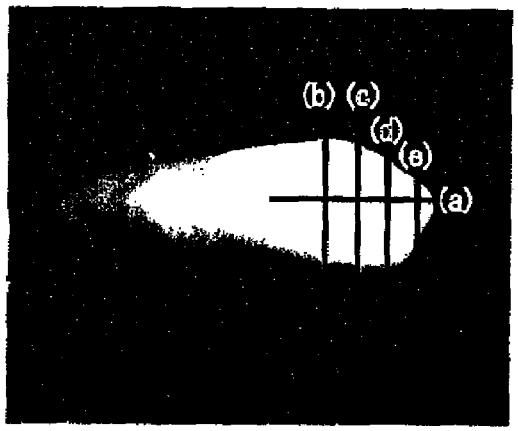
(P)
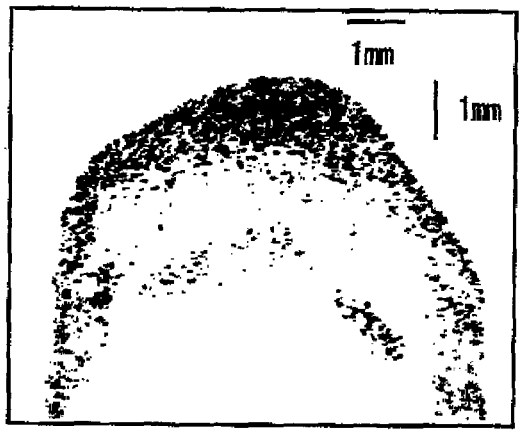
(C)
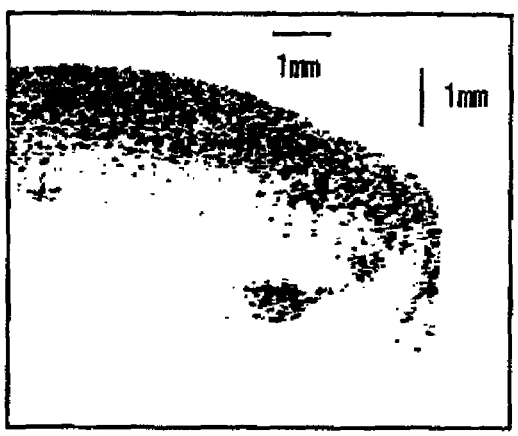
(A)
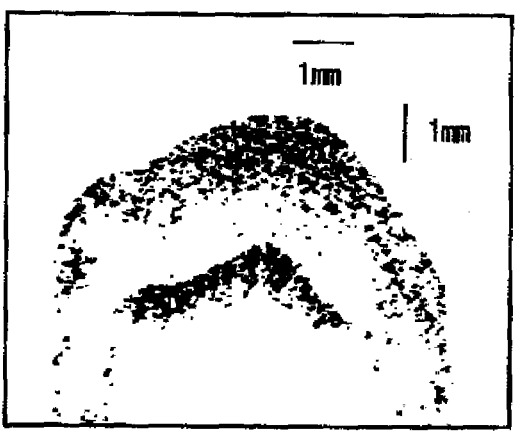
(D)
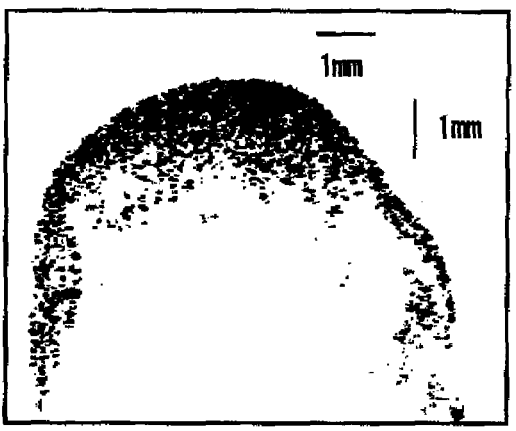
(B)
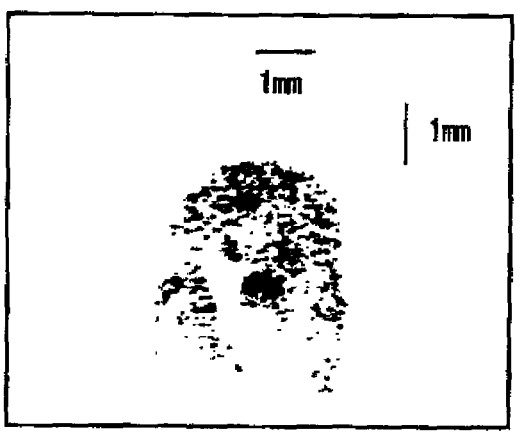
(E)

FIG.25
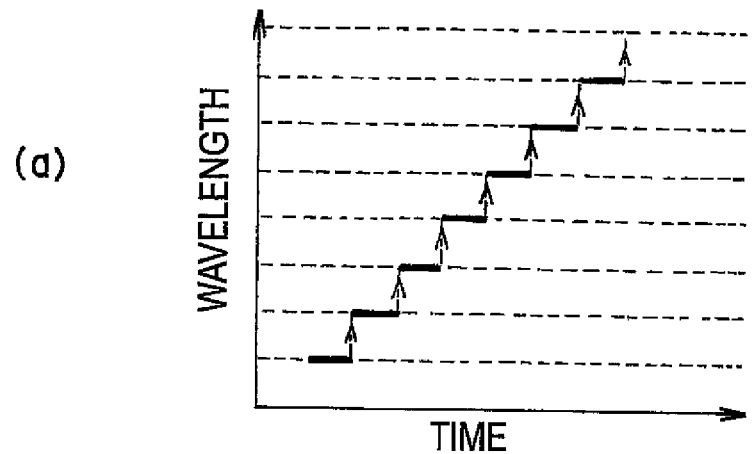
(a)
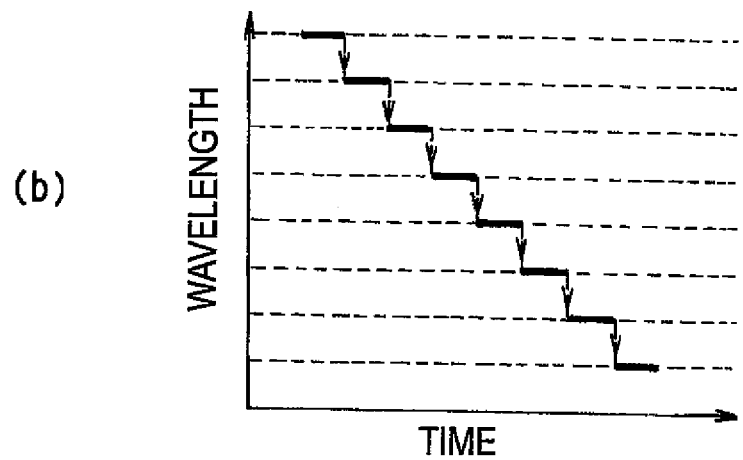
(b)
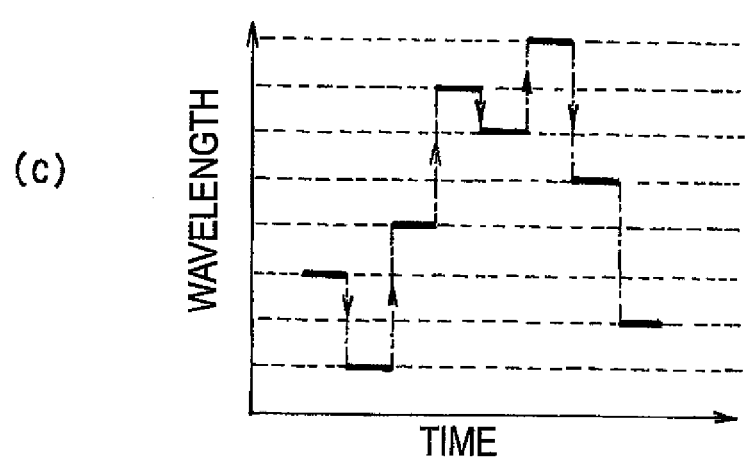
(c)

FIG.36
(a)
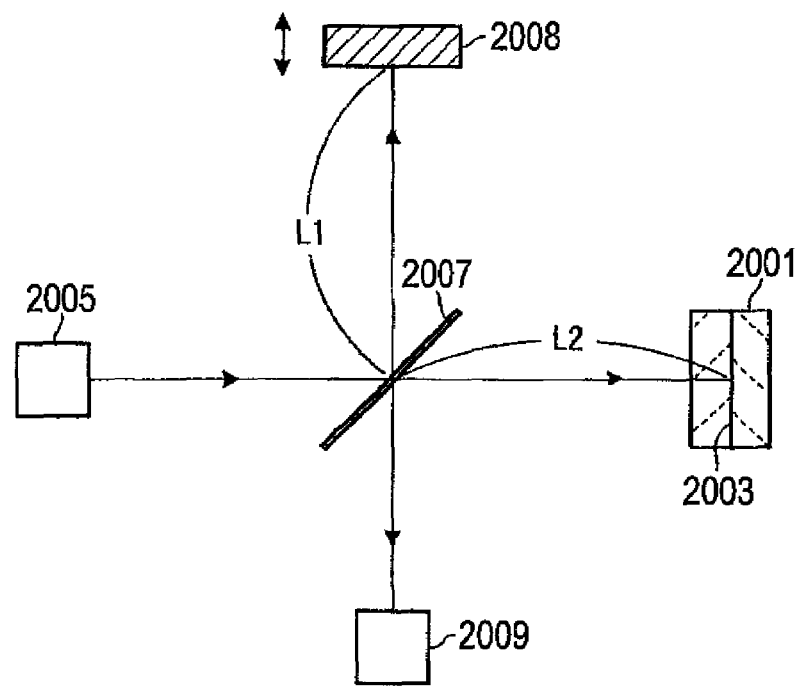
(b)
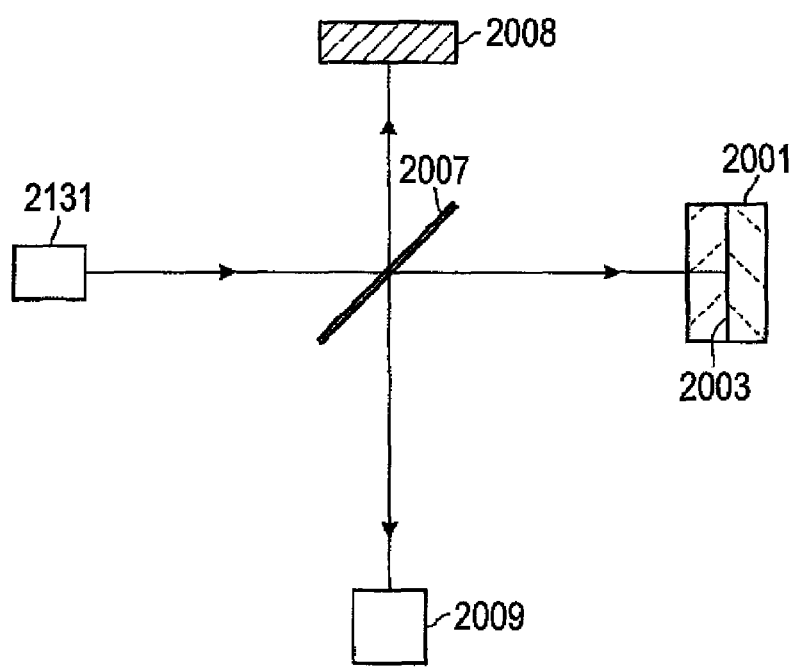

US 7,732,784 B2

WAVELENGTH-TUNABLE LIGHT GENERATOR AND OPTICAL COHERENCE TOMOGRAPHY DEVICE

CROSS REFERENCE TO RELATED APPLICATION

This is a Divisional of U.S. Non-provisional application Ser. No. 10/573,113, which is a U.S. national stage application of International Application No. PCT/JP2004/014302, filed Sep. 22, 2004, and which is incorporated herein by reference in its entirety.

TECHNICAL FIELD

The present invention relates to wavelength-tunable light generators for optical coherence tomography and optical coherence tomographs.

Further, the present invention relates to wavelength-tunable light generators for dental optical coherence tomography and dental optical coherence tomographs, and is very effective when applied to cavity-detection devices that scan the characteristics of a tooth by obtaining a tomographic image of the tooth.

The present invention also relates to optical coherence tomographs and to wavelength-tunable light generators that is used in the optical coherence tomographs. More particularly, the present invention relates to devices that measure tomograms of various structures such as living bodies or coated surfaces or the like by using optical interference and to a wavelength-tunable light generator that are used as the light generator of this device.

BACKGROUND ART

<A> Wavelength-Tunable Light Generator and Optical Coherence Tomography (1) Optical Coherence Tomography (OCT)

Optical coherence tomography (OCT) that utilizes low-coherence light is a new medical measurement technique that permits observation of a tomogram close to the surface of living bodies at a resolution on the order of several tens of μm. OCT has already been practically used in the clinical observation of eye tissue and makes it possible to perform tomographic observation of eye tissue lesions (for example, detachment of the retina) with microscopic accuracy (See Non-Patent Document 1, for example). Clinical applications of this technique have started, but further development of tomographic observation within living bodies combined with an endoscope and so forth are expected.

OCT, which is being practically used now, utilizes a measurement technique known as 'Optical Coherence Domain Reflectometry' (OCDR) that requires mechanical scanning. Meanwhile, research on techniques known as Frequency Domain (FD)-OCT and Optical Frequency Domain Reflectometry (OFDR)-OCT=began recently, which do not require mechanical scanning. Each of these techniques will be described hereinbelow. Further, although referred to as OFDR-OCT in previous documents, because this technique is also called FD-OCT in recent documents, FD-OCT, which is the recent term, will be used in the description that follows. The OCT of the present invention is similar to FD-OCT in that measurements are done in optical frequency regions. Therefore, the name OFDR-OCT is subsequently used for the OCT of the present invention to differentiate it from FD-OCT.

(2) OCDR-OCT

The measurement principle of OCDR-OCT involves using a Michelson interferometer with a low-coherence light source to measure the optical path-length that is rendered as a result of measurement light 2 being irradiated into a sample (living bodies, for example) 1, reflected or backscattered at tissue boundaries 3 within the sample 1, then re-emitted from the sample 1, as shown in FIG. 7. Subsequently, in order to simplify the description of 'reflection' or 'backscattering', these are also simply referred to as 'reflection'.

A portion of the light 2 that enters the sample 1 is reflected as a result of the difference in the refractive indices of tissues on both sides of the tissue boundaries 3 and is re-emitted from the sample 1. The structure in the depth direction within the sample 1 can be found by measuring the optical path-lengths through which re-emitted light 4 has passed. Here, the position of the surface of the sample 1, used as the depth reference point, is provided by reflected light from the surface. Therefore, a cross-sectional image or three-dimensional image or the like of the inside of the sample 1 can be obtained by scanning the entry position of the measurement light 2 on the surface of the sample 1.

FIG. 8 is a schematic view of an OCDR-OCT device. As shown in FIG. 8, light emitted from a light source 5, usually a superluminescence diode (also referred to as 'SLD' hereinafter) is used, is input to a Michelson interferometer 6. This light is divided by a beam splitter 7 and one of the light components is made to converge in the form of a narrow beam and irradiated into the sample 1. The other divided light component is irradiated onto a reference mirror 8. Each of the light components is reflected by the sample 1 and the reference mirror 8, respectively. They are combined by the beam splitter 7 and the combined light enters a photodetector 9.

An SLD has a broad spectral width of approximately 20 nm and, therefore, the coherence length of the emitted light is short at several tens of μm. For example, the coherence length of SLD light with a center wavelength of 850 nm and a spectral width of 20 nm is 15 μm. Hence, the signal light 10 and reference light 11 only interfere with each other when the optical path-lengths of the signal light 10 and reference light 11 agree within the short coherence length range. That is, when the reference mirror 8 is scanned in the direction of the optical axis of the reference light 11, the output of the photodetector 9 shows an interference pattern 15 (called an 'interferogram 15' hereinbelow), as shown in FIG. 9, with a width on the order of the coherence length, only within the short distance 14 where the optical path-length of the signal light 10 and reference light 11 match. In FIG. 9, the vertical axis 12 represents the output of the photodetector 9 and the horizontal axis 13 represents the displacement-distance of the reference mirror 8. The optical path-length of the signal light 10 can be directly found from the position of the reference mirror 8 where the interferogram 15 appears.

The resolution of this method is determined by the coherence length of the light source used and is typically on the order of 10 to 15 μm. Further, the time required for a single measurement is determined by the time required for scanning of the reference mirror 8 and is typically on the order of one second (See Non-Patent Document 1, for example) even for fast measurements.

(3) FD-OCT

The occurrence of mechanical vibrations due to the requirement for the mechanical scanning of the reference mirror 8 is unavoidable in OCDR-OCT and there are restrictions on the scanning distance at a high speed and also on the scanning speed. Because the scanning speed is restricted, there is the problem that the sample (biological sample, for example) must be constrained during measurement, and so forth. As a result, tomographic applications to tissues other than eye tissue, which is relatively easy to constrain, are not straightforward.

As a method not requiring scanning of the reference mirror 8, a frequency domain FD-OCT has been proposed (Non-Patent Document 2, for example), in which a diffraction grating 21 and a charge-coupled device (CCD) 16 are arranged on the output side of the Michelson interferometer as shown in FIG. 10. The spectrum of the output light is measured by the CCD 16, while the reference mirror 8 remains fixed, and the interferogram is calculated and constructed from the spectrum.

The principles of the FD-OCT are as follows. First, while measurement light 18 is focused onto the surface 17 of the sample 1 as an elongated shape, reference light is returned to the beam splitter 7, which is reflected by the reference mirror 8. In such an arrangement, the signal light 10 and reference light 11 are combined and imaged on the CCD 16. Thereupon, a fringe (spatial interference pattern) is produced on the surface of the CCD 16. The intensity of the fringe pattern is measured. Interferogram is calculated by Fourier transforms of the intensity of the fringe pattern with a computer. Further, the focusing/imaging of the measurement light and so forth is performed by two cylindrical lenses 19 that condense only in the x' axis direction and one cylindrical lens 20 that condenses only in the y' axis direction.

In the FD-OCT, because translation of the reference mirror 8 is unnecessary, the measurement time can be short. As an example, measurement time of about 150 msec has been reported. However, this method has following problems.

(Problem 1) The resolution in the transverse direction is low (transverse resolution; on the order of 100 µm).

When a spectral density function is calculated, it is assumed that the reflective faces within the sample extend to a fixed depth and, therefore, an accurate spectral density function is not obtained in a sample in which the depth of the reflective face changes abruptly in the transverse direction (y' axis direction). Therefore, the resolution in the direction (y' axis direction) parallel to the surface of the sample is poor, only values on the order of 100 µm having been reported.

(Problem 2) Narrow measurable range in the depth direction (measurable range; 6.0 mm)

The measurable range $L_m$ in the depth direction is determined by the effective coherence length of each frequency component detected by the CCD. Suppose that the spectral width of each frequency component is $\Delta f$, and c is light speed, the measurable range $L_m$ is given by Equation (1) (refer to the Equations appearing in Non-Patent Document 2). However, what is referred to here as the measurable range is not the measurable range in the depth direction of the sample but instead represents the measurable range according to the optical path difference between the light irradiated into the sample and the reference light. Therefore, the measurable range that appears in Non-Patent Document 2 is two times the measurable range in the depth direction of the sample.

(Equation 1)

$$|L_m| = \frac{c}{\Delta f} \quad (1)$$

In the FD-OCT, $\Delta f$ depends on the pixel width of the CCD in the frequency axis direction (x axis). When an SLD of coherent length 34 µm is the light source, and a CCD with a pixel number in the frequency axis direction of 640 and a pixel interval of 13.3 µm is used, the measurable range calculated by means of Equation (1) is 9.0 mm (See Non-Patent Document 2). However, in moving away from zero on the y axis, the optical path length difference (OPD) between the signal light 10 and reference light 11 following division by the beam splitter 7 increases. As a result, when the fringe cycle approaches the pixel width of the CCD, averaging of the fringe is produced. As a result, the S/N drops and the range over which a clear interferogram can be calculated is reduced to ±6.0 mm for the OPD value (6.0 mm in the depth direction).

(Problem 3)

In measurement of a biological body, the intensity of the light that can be irradiated onto the sample is restricted. Therefore, efficient detection of signal light is important. However, in the FD-OCT, the signal light enters the photodetector (CCD) after a diffraction grating 21 and, therefore, there is the problem that a portion of the signal light is lost by the diffraction grating 21 and the detection efficiency of the signal light is poor.

(Problem 4)

Further, when detection using CCD is performed, the dynamic range representing the number of digits of the measurable intensity is no more than approximately 70 dB. Possibility of application of such detection to retina has been reported. However, that does not necessarily mean that such detection is sufficient for observation of a biological body.

(Problem 5)

Furthermore, there is also the problem that the measurement time is limited by the speed of the CCD, and there is a limit on increasing the measurement speed.

<B> Wavelength-Tunable Light Generator for Dental OCT and Dental OCT Device

The present invention described hereinbelow relates to wavelength-tunable light generator for dental OCT and dental OCT devices. It is extremely effective when applied to a cavity detecting device for diagnosis of the characteristics of a tooth by obtaining a tomographic image of a tooth. OCT is noninvasive to a biological body and has a high resolution. Therefore, applications not only to the tomography of retina but also to that of other organs have been tried (See Non-Patent Document 1, for example), and detecting the characteristics of a tooth, for example, may be considered (See Non-Patent Document 5, for example).

<C> Device for Measuring a Tomogram of Various Structures such as a Biological Body or Coated Surfaces OCT is optical coherence tomography that is useful for imaging a tomogram of a retina or the like (See Non-Patent Document 7, for example). The OCT has attracted attention for being noninvasive to a biological body and for its high resolution. Applications to organs other than eye have also been tried (See Non-Patent Document 7, for example). One of the characteristics of this measurement method is its spatial resolution in the depth direction, and measurement devices with a resolution on the order of approximately 10 µm have been put to practical use. The resolution is determined by the spectral width of the light source. However, for OCT in practical use, to realize user-friendly, reliable, small-scaled and light-weighted systems, usually a semiconductor light-emitting element and, more specifically, a near-infrared SLD is used for the light source. That is, the resolution of OCT devices in practical use is limited by the spectral width of the SLD. The spatial resolution of OCT is inversely proportional to the spectral width of the light source and, therefore, the spectral width of the light source may be increased in order to increase the resolution. However, the spectral width of SLD is determined by the physical nature of the light-emitting layer and so forth and it is therefore difficult to increase the spectral width above the value realized now.

To overcome this limit, a trial, in which a plurality of SLDs of different center wavelengths are combined to substantially implement a broadband light source, has been proposed by Satou et al (See Non-Patent Document 8, for example).

[Patent Document 1] Japanese Patent Application Laid Open No. H6-53616

[Patent Document 2] Japanese Patent Application Laid Open No. H6-61578

[Patent Document 3] U.S. Pat. No. 4,896,325

[Patent Document 4] U.S. Pat. No. 3,471,788

[Patent Document 5] Patent Application No. 2003-335207

[Non-Patent Document 1] Chan Kin Pui, 'Microscopic diagnostics using optical coherence tomography for clinical applications', Optronics, Optronics Corp, Jul. 10, 2002, 247th Edition, pages 179 to 183

[Non-Patent Document 2] TERAMURA Yuichi, MIKUNI Masayuki, KAMINARI Fumihiko Proceeding of 23rd Meeting on Lightwave Sensing Technology, page 39

[Non-Patent Document 3] Handbook of Optical Coherence Tomography (edited by Brett E. Bouma, Guillermo J. Tearney), pages 364 to 367

[Non-Patent Document 4] YOSHIKUNI Yuzo 'Developmental trends of wavelength-tunable lasers and expectations for system applications', Applied Physics, Applied Physics Scientific society, 2002, 71st Volume, Eleventh edition, pages 1362 to 1366

[Non-Patent Document 5] Edited by Brett E. Bouma et al., Handbook of Optical Coherence Tomography, (USA), Marcel Dekker Inc., 2002, p. 591 to 612

[Non-Patent Document 6] CHOI, Donghak 'High-speed, high-resolution OFDR-OCT using SSG-DBR laser', Twenty-eighth Optical symposium lecture proceedings, Corp, Applied Physics Subcommittee meeting, Optical Society of Japan, Jun. 19, 2003, pages 39 to 40

[Non-Patent Document 7] Chan Kin Pui, 'Microscopic diagnostics using optical coherence tomography for clinical applications', Optronics, Optronics Corp, Jul. 10, 2002, 247th Edition, pages 179 to 183

[Non-Patent Document 8] Applied Optics February 2003, pages 7 to 11, SATOU, Manabu

[Non-Patent Document 9] Twenty-eighth Optical Symposium proceedings, Pages 39 to 40 (Published Jun. 19, 2003)

PROBLEMS TO BE SOLVED BY THE INVENTION

<A> Wavelength-Tunable Light Generator and OCT Device

The reason why OCDR-OCT is practically used in retina measurement is that constraining the measurement object is relatively easy. However, there are a number of parts in a biological body that show movements difficult to constrain, such as peristaltic movements of the gastrointestinal tract. Tomographic observation by conventional OCT (both OCDR-OCT and FD-OCT) is not suitable for the observation of such parts.

For example, when parts that move at speeds of a number of mm per second are observed by means of OCDR-OCT, the distance (a number of mm) moved by the observation object during the measurement time (approximately one second) is quite large in comparison with the resolution (several tens of μm) and, therefore, imaging of the tomogram is impossible.

Although tomography using FD-OCT is rapid compared with tomography using OCDR-OCT, the currently obtained measurement times (150 msec) are still inadequate for the observation of parts such as those mentioned above. This is because the data processing to obtain interferogram takes time due to the complex calculation process. That is, there is the problem that current OCT is not suitable for the observation of biological body parts, that are difficult to constrain. There is also the problem that, as mentioned earlier, the resolution in the transverse direction is low or the measurable range in the depth direction is also short.

An object of the present invention provide an OCT technique that solves the above problems and permits tomographic observation of biological body parts that are difficult to constrain and to provide a tomographic observation technique that removes the burden on the biological body by rendering constraint unnecessary even for the observation of constrainable parts.

<B> Wavelength-Tunable Light Generator for Dental OCT and Dental OCT Device

An OCT device that uses conventional OCT as described earlier requires broadband light source and, for this reason, a light-emitting light source of an SLD or spontaneous emission of a fiber amplifier is used. Hence, observation has been performed with a currently available wavelength range of 0.85 μm or 1.31 μm (See page 594 of Non-Patent Document 5, for example). However, in order to obtain deeper penetration, measurement at longer wavelengths is required. Therefore, a readily available light source that emits light in a longer wavelength range and a method that permits OCT measurement by using this light source have become necessary.

Furthermore, an OCT signal becomes weaker for deeper penetration and, in order to enable measurement at such deeper penetration, it is necessary to use an OCT method with a higher-sensitivity.

Moreover, when an early cavity in enamel is to be detected, for example, because microcrystals (hydroxylated apatite) constituting enamel have a birefringent index, there is blurring in a tomogram that employs a device incapable of measuring polarization characteristics. There is a need for tomogram imaging OCT that permits OCT measurement of a higher sensitivity in longer wavelength ranges than the prior art and which also permits measurement of polarization characteristics.

Furthermore, in place of the conventional OCT that permits the measurement of intensity-tomogram, spectral OCT is required, that permits not only the measurement of intensity-tomogram but also the measurement of the compositional ratio of constituent substances to obtain more accurate diagnostic knowledge.

Further, because a reference mirror must be mechanically moved in conventional OCT, there are restrictions on the measurement speed. The slow measurement speed allows motion of the measurement object, i.e. tooth, during measurement, which leads to deformation of the tomographic image (motion artifact) (See page 596 of Non-Patent Document 5, for example). Hence, an OCT method is required that makes implementation of the above performance and also faster measurement speeds possible.

To implement above requirements, an object of the present invention is to enable detection of minute early-stage cavity and detailed diagnosis of teeth by providing wavelength-tunable light generator for dental OCT and dental OCT device, that enable high speed and high sensitivity discrimination of tissue composition.

An object of the present invention is to enable detailed diagnoses teeth.

<C> Device for Imaging Tomogram of Various Structures such as Biological Body or Coated Surface or the Like Satou et al. have argued that (1) resolution improves with a light source combining a plurality of SLDs of different center wavelengths, and (2) side lobes occurring as a result of the combination of light sources can also be suppressed by optimizing the light source intensity, center wavelengths, and spectral widths. However, as will be described hereinbelow, the present inventors discovered, by resolving the OCT signal for the combined light source, that (1) the resolution does not necessarily narrow in inverse proportion to the spectral of the combined source (2) large side lobes are produced, and (3) as the number of combined light sources increases, the amplitude of the side lobes increases.

The schematic diagram of the light source ('combined light source' hereinafter) proposed by Satou et al. is shown in FIG. 35. An example of an OCT device, in which the combined light source is used, is shown in FIG. 36(a). This OCT device comprises a combined light source 2005, a photodetector 2009, a reference mirror 2008, and a beam splitter 2007.

Equation 32 represents an OCT signal F(x) from the reflective face 2003 in the sample 2001 that is obtained by using the combined light source 2005.

(Equation 2)

$$F(\chi) = \sqrt{r_r r_s} \sum_{i=1}^{N} I_i \exp\left[-\left(\frac{2\sqrt{\ln 2}}{\Delta Z_i}\chi\right)^2\right] \cos(4\pi f_{ci}\chi/C) \quad (32)$$

Here, x is the difference $(L_1-L_2)$ between the optical path length $L_1$ of the reference mirror 2008 and the beam splitter 2007 and the optical path length $L_2$ between the reflective face 2003 and the beam splitter 2007. $r_r$ and $r_s$ are the optical reflectivity of the reference mirror 2008 and reflective face 2003, respectively. $I_i$ represents the intensity of the i-th light source comprising the combined light source 2005. C is the light speed. The combined light source 2005 is produced by multiplexing a plurality of light sources 2021 of different center wavelengths as shown in FIG. 35 and, more specifically, combining SLD outputs by means of an optical coupler 2022. $\Delta Z_i$ is the full width at half maximum of the OCT signal obtained by the i-th light source alone and $f_{ci}$ is the center frequency of the i-th light source.

In the OCT device shown in FIG. 36(a) which is employed by Satou et al., the broadband light source 2005 is used and the reference mirror 2008 is moved at a speed v. In this case, x is related to v by the relation x=vt at measurement time t and Equation (32) is rewritten by the following equation as a function of time t.

(Equation 3)

$$F_t(t) = \sqrt{r_r r_s} \sum_{i=1}^{N} I_i \exp\left[-\left(\frac{2\sqrt{\ln 2}}{\Delta Z_i}v\right)^2 t^2\right] \cos\left(\frac{4\pi f_{ci}v}{C}t\right) \quad (33)$$

Although actual measurement involves measuring a signal that changes with time, the function F(x) representing position information for the measured results will be described hereinbelow. Further, the OCT method shown in FIG. 36(a) is known as OCDR-OCT. In Equation (32), it should be noted that the OCT signal observed with the combined light source is only superposition of the OCT signals produced by individual light sources. That is, the OCT signal observed with the combined light source expressed by Equation (32) above is the result of superposition of OCT signals produced by the i-th light source expressed by Equation (34) below.

(Equation 4)

$$I_i \exp\left[-\left(\frac{2\sqrt{\ln 2}}{\Delta Z_i}\chi\right)^2\right] \cos(4\pi f_{ci}\chi/C) \quad (34)$$

The apparent narrowing of the half width of the OCT signal nevertheless is due to the production of a beat signal when the oscillation term in Equation (34)

(Equation 5)

$$\cos(4\pi f_{ci}\chi/C) \quad (35)$$

are superposed because each light source has a slightly different frequency each other.

Because the envelope term in Equation (34)

(Equation 6)

$$\exp\left[-\left(\frac{2\sqrt{\ln 2}}{\Delta Z_i}\chi\right)^2\right] \quad (36)$$

modulated by a decrease in the amplitude of this beat signal, the width of the OCT signal appears to narrow in the neighborhood of x=0. However, in actual signal, because the amplitude of the beat signal returns temporarily to the origin as x increases from x=0, a side lobe 2031 is produced (FIG. 37). The side lobe is produced by the product of the beat oscillating signal and the envelope produced by individual light sources 2021. Therefore, a large side lobe 2031 is produced.

This phenomenon will be described hereinbelow on the basis of a specific example. Use of wave number k $(=2\pi/\lambda)$ instead of wavelength $\lambda$ is more convenient to describe the spectra of the light sources. Assume that the combined light source is composed of a light source 1 and light source 2 whose spectral form is Gaussian and which have the same integral intensity I and the same spectral width $\sigma$ with the center frequencies $k_1$ and $k_2$, respectively. Therefore, the spectrum S(k) of the combined light source is expressed as follows.

(Equation 7)

$$S(k) = \sum_{i=1}^{2} I \frac{1}{\sqrt{\pi}\sigma} \exp\left[-\frac{(k-k_1)^2}{\sigma^2}\right] \quad (37)$$

Here, the half width at half maximum $W_f$ of the individual light source is as follows.

(Equation 8)

$$W_f = \sigma\sqrt{\ln 2} \quad (38)$$

When $W_f$ is used, the full width at half maximum of the OCT signal is given by the following equation.

$$\Delta Z = (2\ln 2)/W_f$$

Here, for the case that the center frequencies of the light sources 1 and 2 are separated by twice the half width at half maximum $W_f$, the spectral shape 2031 of the combined light source becomes as shown in FIG. 38. The vertical axis is normalized by the integral intensity I of the individual light sources. Here, spectrum 2032 and spectrum 2033 are the respective spectrum of light source 1 and light source 2.

Then, the OCT signal f(x) for the combined light source is expressed as follows by using the spectral width σ and the wave numbers of the light sources 1 and 2.

(Equation 9)

$$f(\chi) = \sqrt{r_r r_s} I \cos(2\chi k_1)e^{-\sigma^2 \chi^2} + \sqrt{r_r r_s} I \cos(2\chi k_2)e^{-\sigma^2 \chi^2} \quad (39)$$
$$= \sqrt{r_r r_s} e^{-\sigma^2 \chi^2} 2\cos\left[\frac{k_1+k_2}{2} 2\chi\right] \cos[(k_1-k_2)\chi]$$

Here, the term (Equation 10)

$$\cos\left[\frac{k_1+k_2}{2} 2\chi\right] \quad (40)$$

oscillates at the cycle of the same order as $k_1$ (or $k_2$). Meanwhile, the term (Equation 11)

$$\cos[(k_1-k_2)\chi] \quad (41)$$

provides the envelope of the beats of the above oscillations. Further, the term (Equation 12)

$$\sqrt{r_r r_s} e^{-\sigma^2 \chi^2} \quad (42)$$

gives the envelope of the OCT signal for individual light sources.

FIG. 39 shows the envelope (right half) of an OCT signal produced by the combined light source, where the oscillation term in Equation (40) is neglected. The horizontal axis x is normalized by 1/σ. The vertical axis is normalized by the value when x=0. The envelope 2042 is for the above combined light source. The envelope 2041 is for individual light sources and envelope 2043 is the envelope for the case where four light sources are combined. The equation for the OCT signal with four light sources is not shown here but the similar beat signal to the case with two light sources is produced.

It can be seen from FIG. 39 that the half width of the OCT signal surely decreases with an increase of the number of light sources but the decrease is not inversely proportional to the number of light sources. That is, the half width does not decrease inversely proportional to an increase in the spectral width of the combined light source. More specifically, the half width with two light sources is 0.62 times of that with one light source and the half width with four light sources is only 0.33 times of that with light source. The decreases by 0.5 and 0.25 are expected if the resolution were inversely proportional to the spectral width. In FIG. 39, side lobes with large vertical oscillations crossing 0 are observed (The reason why the OCT signal reaches a negative value is that Equation (39) only expresses the interference component and the intensity of the background reference light and signal light are omitted). Further, the amplitude of the side lobe is clearly larger with the four light sources than with the two.

That is, the shape of the OCT signal of the combined light source is affected by the envelope 2041 for the individual light sources, which is determined by the spectral width of the individual light source. Even though the width of the OCT signal may appear to narrow, the extent of the narrowing is small and large side lobes appear. Therefore, even when a combined light source is used, there is the problem that there is actually not much improvement in the resolution of the OCT image. That is, while the resolution does not improve as expected with the combined light source, large side lobes appear, which result in ghosts in the OCT image. Therefore, the problem to be solved by the present invention is to increase the resolution of the OCT signal for OCT devices and to prevent an increase in side lobes.

DISCLOSURE OF THE INVENTION

<A> Wavelength-Tunable Light Generator and OCT Device (1) First Invention

The first invention is the wavelength-tunable light generator comprising means capable of changing the wave number stepwise, that can be suitably used as the light source for OCT device that measures a cross-sectional image of a measurement object by irradiating the measurement object with light and detecting the reflected light or the backscattered light produced within the measurement object by means of a detector. The wavelength-tunable light source is characterized in that the output wave number of the source is changed stepwise. More specifically, the wavelength-tunable light generator is characterized in the capability to change the output wave number gradually and stepwise or randomly.

(2) Second Invention

The second invention is a wavelength-tunable light generator in which the width of the tunable range of the wave number is at least $4.7 \times 10^{-2}$ μm$^{-1}$ and the frequency width of the emitted light is no more than 13 GHz, comprising: means capable of changing the wave number stepwise at wave number intervals of no more than $3.1 \times 10^{-4}$ μm$^{-1}$ and time intervals of no more than 530 μs. By using the said wavelength-tunable light generator as the light source for the OCT device, tomographic observation of biological body parts that are difficult to constrain is made possible. Here, the wave number is equal to 2π divided by the wavelength.

(3) Third Invention

The third invention is a wavelength-tunable light generator in which the width of the tunable range of the wave number is at least $4.7 \times 10^{-2}$ μm$^{-1}$ and the frequency width of the emitted light is no more than 52 GHz, comprising: means capable of changing the wave number stepwise at the wave number intervals of no more than $12.4 \times 10^{-4}$ μm$^{-1}$ and time intervals of no more than 530 μs. By using this wavelength-tunable light generator as the light source for the OCT device, the measurable distance shortens compared with that of the second invention, but tomographic observation of biological body parts, that are difficult to constrain and move at a higher speed, is made possible.

(A) Effects Afforded by 'Comprising: Means Capable of Changing the Wave Number Stepwise'

In conventional OCT, broadband (low coherence) continuous output light (CW light) emitted by an SLD is used as measurement light, the interferogram (FIG. 9) is measured in OCDR-OCT, and the fringe 22 (FIG. 11) is measured in FD-OCT. Meanwhile, according to the constitutional requirement 'comprising: means capable of changing the wave number stepwise' of the present invention, the response of the inteferometer for each wave number can be measured by changing the wave number of the light source used in the measurement stepwise a little at a time as shown in FIG. 1(a), for example. According to this characteristic, an increase in the speed of the tomography and an improvement in the resolution in the horizontal direction are achieved as described hereinbelow. Moreover, various problems such as a drop in the detection rate of the signal optical intensity due to the presence of a diffraction grating constituting a problem for FD-OCT, an insufficient dynamic range attributable to the performance of the CCD, and the tomography speed being rate-limited by the response speed of the CCD are resolved.

Further, although the wave number increases gradually with respect to the wave number sweep time in FIG. 1(A), there is not necessarily a need for the gradual increase and there is no problem whatsoever even when a gradual decrease of the wave number takes place. Further, the wave number need not necessarily change gradually. The whole of a predetermined wave number may be scanned within the measurement time. That is, the change in the wave number may be irregular as shown in FIG. 1(B). That is, stepwise shapes include not only cases where the wave number undergoes a gradual stepwise increase with respect to time but also a gradual decrease. Moreover, the wave number need not necessarily be changed gradually. Stepwise shapes include all discontinuous forms of scanning where all of a predetermined wave numbers are scanned within the measurement time.

Here, the predetermined wave numbers are desirably a set of wave numbers with equal intervals but is not necessarily limited to such a set. A set of wave numbers in which the wave number interval is not equal is also acceptable. When the wave number interval is not equal, correction in the data processing for the tomogram construction mentioned subsequently in the first embodiment is required but the correction method can be derived based on the knowledge related to a Fourier transform corresponding to the wave number-scanning forms. As mentioned earlier, with the means capable of changing the wave number stepwise, the wave number interval and the order of the wave number are not limited as long as the construction of the tomogram is possible. Further, although a discontinuous change in the wave number is desirable, as long as the wave number can be kept at a specified value during necessary time, the change may be continuous. Such cases are also included in 'stepwise'.

Because scanning of the reference mirror, required in OCDR-OCT, is not required in the measurement process of the present invention, measurement can be performed at a speed faster than OCDR-OCT. On the other hand, with the present invention, because an interferogram is obtained from a spectroscopic characteristic (FIG. 2) that combines the output optical intensities of the interferometer for the respective wave numbers, there is no need to construct an interferogram by computing a spectral density function that includes both intensity information and phase information as like FD-OCT. As a result, in the case of the present invention, interferogram can be calculated by simple data processing. Further, the calculation itself of a spectral density function is not necessary and, therefore, data processing can be performed in a shorter time than in conventional FD-OCT and high-speed measurement is possible. The data processing of the present invention will be described in the first embodiment.

Further, the assumption (the depth distribution in the transverse direction must be the same), that causes degradation of the transverse resolution in conventional FD-OCT and is assumed in order to calculate the spectral density function, is also unnecessary with the present invention and, therefore, deterioration of the transverse resolution does not occur.

Further, a mechanical operation such as reference mirror scanning is not necessary in the tomography implemented by using the present invention and interferogram can be calculated by a simple procedure in tomography that employs the present invention as will be described subsequently. Hence, the imaging speed of tomography can be increased. Further, because the assumption, that causes the transverse resolution degradation in conventional FD-OCT, is not necessary in tomography implemented by using the present invention, there is also no such degradation in the transverse resolution.

In addition, problems associated with the diffraction grating and CCD such as a reduction in the detection efficiency of the signal light due to the diffraction grating, an insufficient dynamic range attributable to the performance of the CCD, and the acquisition speed of tomography being rate-limited by the response speed of the CCD, which are problems pertaining to FD-OCT that employs a diffraction grating and CCD, are naturally resolved by the present invention which does not use a diffraction grating and CCD.

Furthermore, as will be described subsequently, the present invention affords the effect that the intensity of the interferogram, that is obtained under the condition that the intensity of the light that can be irradiated onto the sample is limited to be lower than a certain maximum value, is stronger by approximately 100 to 1000 times the signal intensity of OCDR and several ten times stronger than that of FD-OCT.

Further, chirp OCT has been proposed as OCT that is similar to the present invention (See pages 364 to 367 of Non-Patent Document 3). Details of this technique are not explained here because this technique is not practically used due to problems listed below. Following differences exist between the present invention and this technique.

That is, although chirp OCT agrees with the present invention in that the light source is a wavelength-tunable light source, chirp OCT differs in that the wave number of the light source is swept at a fixed speed continuously. Further, based on the measurement principle, there is the shortcoming that jumps in the wave number, that is, mode hops, are not allowed for the light source used in chirp OCT. Therefore, when chirp OCT is used, it is necessary to obtain a light source that is free from mode hops over a wide frequency range. However, it is difficult to obtain such a light source. As a result, this technique has not been put to use.

On the other hand, with the present invention, there is no need to change the wave number continuously and, even if there were a slight mode hop in the wavelength-tunable light source, because the change in the wave number may be stepwise, it is not an obstacle to measurement of a tomogram.

(B) Effect of Limiting the Wave Number Range and so on

Thus, the present invention is suited for increasing the speed of tomography. Further, by restricting usage to the wavelength-tunable light generator that comprises means capable of changing the wave number stepwise at wave-number intervals of no more than $3.1 \times 10^{-4}$ $\mu m^{-1}$ and time intervals of no more than 530 µs, which is a wavelength-tunable light generator in which the width of the tunable range of the wave number is $4.7 \times 10^{-2}$ $\mu m^{-1}$ or more and the frequency width of the emitted light is no more than 13 GHz, a resolution of 80 µm and a measurable range of 10 mm can be secured and observation of a sample that moves at no more than 1 mm per second is made possible. That is, the second invention makes the observation of biological body parts, that are difficult to constrain and move 1 mm per second, possible.

In addition, by restricting the usage of the wavelength-tunable light generator that comprises means capable of changing the wave number stepwise at wave-number intervals of no more than $12.4 \times 10^{-4}$ µm and time intervals of no more than 530 µs, which is a wavelength-tunable light generator in which the width of the tunable range of the wave number is $4.7 \times 10^{-2}$ µm$^{-1}$ or more and the frequency width of the emitted light is no more than 52 GHz, a resolution of 80 µm and a measurable range of 2.5 mm can be secured and observation of a sample that moves at no more than 4 mm per second is made possible. That is, the second invention makes the observation of biological body parts, that are difficult to constrain and move 4 mm per second, possible.

The reason why such effects are realized is described hereinbelow.

When a sample moves during measurement, the positions of the reflective faces within the sample are not fixed and the measured values for the positions of the reflective faces are unreliable. The calculation of position itself is not possible when the movement of the sample is intense. However, even if it does not come to this, the resolution (called the 'dynamic resolution' hereinbelow) of a moving sample generally become worse than the resolution (called the 'static resolution' hereinbelow) of a stationary sample. Therefore, in order to obtain a dynamic resolution of 80 µm, a static resolution of 80 µm must be secured first.

As described in the section on the principles of the first embodiment (described subsequently), the inventors of the present invention discovered that, for the width of the tunable range of the wave number $W_k$, the static resolution $\Delta Z$ is given by Equation (2) below. Here, it is assumed that the bundle of the measurement light has a rectangular spectral shape.

(Equation 13)

$$\Delta Z = \frac{3.79}{W_k} \quad (2)$$

Equation (2) shows the condition to obtain a dynamic resolution 80 µm is the width of the tunable range of the wave number must be $4.7 \times 10^{-2}$ µm$^{-1}$ or more. This corresponds to the constitutional requirement 'the width of the tunable range of the wave number is $4.7 \times 10^{-2}$ µm$^{-1}$ or more' of the second and third inventions above.

Further, the measurable range in the depth direction depends on the coherent lengths of the measurement light at each wave number. Therefore, the measurable range is limited by the spectral frequency width $\Delta f$ of the measurement light. Because the following Equation (3) holds for the relation between the measurable range $L_m$ in the depth direction and the spectral frequency width $\Delta f$ (full width at half maximum), in order to secure a 10 mm measurable range, the frequency width of the emitted light must be no more than 13 GHz. This corresponds to the constitutional requirement 'a wavelength-tunable light generator in which the frequency width of the emitted light is no more than 13 GHz' of the second invention.

Further, the measurable range 2.5 mm can be secured by setting the frequency width of the emitted light at no more than 52 GHz. This corresponds to using a wavelength-tunable light generator in which the frequency width of emitted light is no more than 52 GHz, which is a constitutional requirement of the third invention.

(Equation 14)

$$L_m = \frac{2c \ln 2}{\pi} \frac{1}{\Delta f} \quad (3)$$

This equation (3) is obtained by modifying Equation (22) on page 46 of Non-Patent Document 3. Here, c represents light speed. For a semiconductor LD of single longitudinal mode, such a value can be easily achieved.

On the other hand, as described subsequently in the first embodiment, the measurable range $L_m$ in the depth direction of the sample is also limited by the wave number interval $\Delta k$ of the measurement light. That is, according to the Nyquist theorem, the measurable range $L_m$ is expressed by the following Equation (4).

(Equation 15)

$$L_m = \frac{\pi}{\Delta k} \quad (4)$$

It can be seen from Equation (4) that, in order to obtain a measurable range of 10 mm, the wave number interval must also be no more than $3.1 \times 10^{-4}$ µm$^{-1}$. This corresponds to the constitutional requirement of the second invention for a wave number interval of no more than $3.1 \times 10^{-4}$ µm$^{-1}$.

Furthermore, it can be seen from Equation (4) that, in order to obtain a measurable range of 2.5 mm, the wave number interval must also be no more than $12.4 \times 10^{-4}$ µm$^{-1}$. This corresponds to the constitutional requirement of the third invention for the wave number interval of no more than $12.4 \times 10^{-4}$ µm$^{-1}$.

Based on the above requirements, by sufficiently shortening the wave number changing time interval $t_h$ as indicated below, a sample that moves at a speed of 1 mm per second can be observed at a dynamic resolution of 80 µm while securing a measurable range of 10 mm. The conditions required for the wave number changing time interval are as detailed below.

For degradation of the resolution by motions of the sample to be prevented, the measurement time $t_m$ must be short so that the distance that the sample moves within the measurement time is no more than the static resolution. That is, blurring at or below the static resolution is allowed. According to this condition, for the static resolution $\Delta Z$ and the sample movement speed v, the measurement time $t_m$ required in order to prevent resolution degradation caused by motions of the sample is expressed by Equation (5) below:

(Equation 16)

$$t_m \leq \frac{\Delta Z}{v} \quad (5)$$

Further, the total number of wave numbers used in the measurement is obtained by dividing the tunable wave number range $W_k$ by the wave number interval $\Delta k$ and, therefore, the following relationship holds between the measurement time $t_m$ and the wave number changing time interval $t_h$.

(Equation 17)

-continued $$t_m = \frac{W_k}{\Delta k} \times t_h \quad (6)$$

Therefore, it can be seen from Equations (5) and (6) that in order to measure a sample, the movement speed v of which is 1 mm/s, the wave number changing time interval $t_h$ must be no more than 530 µs. This corresponds to the constitutional requirement of the second invention for means capable of changing the wave number stepwise at time intervals of no more than 530 µs.

Furthermore, it can be seen that, in order to measure a sample, the movement speed v of which is 4 mm/s, for the wave number interval $\Delta k$ no more than $12.4 \times 10^{-4}$ µm$^{-1}$, the wave number changing time interval $t_h$ must be no more than 530 µs. This corresponds to the constitution requirement of the third invention for means capable of changing the wave number stepwise at time intervals of no more than 530 µs As is clear from the description above, by restricting the wavelength-tunable light generator to a wavelength-tunable light generator comprising means capable of changing the wave number stepwise at wave number intervals of no more than $3.1 \times 10^{-4}$ µm$^{-1}$ and time intervals of no more than 530 µs, which is a wavelength-tunable light generator in which the width of the tunable range of the wave number is at least $4.7 \times 10^{-2}$ µm$^{-1}$ and the frequency width of the emitted light is no more than 13 GHz, observation of a sample that moves at a speed of 1 mm per second is possible while securing a resolution of 80 µm and a measurable range of 10 mm.

Moreover, by restricting the wavelength-tunable light generator to a wavelength-tunable light generator comprising means capable of changing the wave number stepwise at time intervals of no more than 530 µs and wave number intervals of no more than $12.4 \times 10^{-4}$ µm$^{-1}$, which is a wavelength-tunable light generator in which the width of the tunable range of the wave number is at least $4.7 \times 10^{-2}$ µm$^{-1}$ and the frequency width of the emitted light is no more than 52 GHz, observation of a sample that moves at a speed of 4 mm per second is possible while securing a resolution of 80 µm and a measurable range of 2.5 mm.

Further, although it is assumed in the above description that wave number scanning is performed only once, tomography can be performed by irradiating the sample with oblong measurement light and using a CCD as a photodetector. Equations (2) and (4) are strict for a case where the bundle of the measurement light has a rectangular spectral shape. However, even when the spectral shape is changed to another shape such as a Gaussian shape, the results obtained are substantially the same as those in the case where the spectral shape is a rectangle, without changing the resolution and so forth greatly.

(C) Preferable Wave Number Range and so Forth

As is clear from the above description, the preferred wave number range or the like is automatically determined by Equations (2) to (6) as long as the resolution, measurable range, and measurable movement-speed of the sample are determined. A preferred example of the resolution and so forth is as described above, but the resolution, measurable range and movement speed of the sample are more preferably no more than 40 µm, at least 100 mm, and no more than 3 mm/s respectively. The most preferred values are no more than 20 µm, at least 1000 mm, and no more than 9 mm/s respectively. As a result, the wave number range and so forth to meet respective demand are as follows.

(a) When the Sample Speed is No More than 1 mm/s

Combinations of the wave number interval, frequency width, tunable wave number width and wave number changing time interval when the sample speed is no more than 1 mm/s are as follows.

TABLE 1

| wave number interval + frequency width (horizontal fields) vs tunable wave number width (vertical fields) | No more than $3.1 \times 10^{-4}$ µm$^{-1}$ No more than 13 GHz | No more than $3.1 \times 10^{-5}$ µm$^{-1}$ No more than 1.3 GHz | No more than $3.1 \times 10^{-6}$ µm$^{-1}$ No more than 130 MHz |
|---|---|---|---|
| At least $4.7 \times 10^{-2}$ µm$^{-1}$ | No more than 530 µs | No more than 53.0 µs | No more than 5.30 µs |
| At least $9.5 \times 10^{-2}$ µm$^{-1}$ | No more than 133 µs | No more than 13.3 µs | No more than 1.33 µs |
| At least $1.9 \times 10^{-1}$ µm$^{-1}$ | No more than 33.1 µs | No more than 3.31 µs | No more than 0.331 µs |

In Table 1, the horizontal fields indicate the preferred wave number intervals and frequency width and the vertical fields indicate the preferred tunable wave number widths.

Here, the values of the wave number interval and frequency width, namely, no more than $3.1 \times 10^{-4}$ µm$^{-1}$ and no more than 13 GHz, no more than $3.1 \times 10^{-5}$ µm$^{-1}$ and no more than 1.3 GHz, and no more than $3.1 \times 10^{-6}$ µm$^{-1}$ and no more than 130 MHz correspond to measurable ranges of at least 10 mm, at least 100 mm, and at least 1000 mm, respectively. Further, the values for the tunable wave number width, namely, at least $4.7 \times 10^{-2}$ µm$^{-1}$ at least $9.5 \times 10^{-2}$ µm$^{-1}$ and at least $1.9 \times 10^{-1}$ µm$^{-1}$ correspond to resolutions of no more than 80 µm, no more than 40 µm, and no more than 20 µm.

Here, because the measurable range is sufficiently long when the measurable range is at least 100 mm, even when the measurement point is changed, re-adjustment of the reference mirror is not required.

Further, although the expression that the wave number interval is 'no more than' a fixed value is employed, cases where the wave number interval is 0 µm$^{-1}$ are not included. This is because 'wave number interval' means that a plurality of wave numbers should exist at finite intervals. With a wave number interval of 0 µm$^{-1}$, the wave numbers are unified.

(b) When the Sample Speed is No More than 3 mm/s

The respective wave number changing time interval in Table 1 may be one third.

(c) When the Sample Speed is No More than 9 mm/s

The respective wave number changing time interval in Table 1 may be one ninth.

(d) When Tomography is Performed by Scanning the Sample Surface with Measurement Light that is Focused at One Point When the number of measurement points for scanning is n (n=10, 50, 100, 200, 400, and 800, for example) or more, the wave number changing time interval shown in (a) to (c) may be no more than 1/n.

Although a tomogram is obtained with one scan of the wave numbers as mentioned earlier, when a Mach-Zehnder type interferometer is used as in the first embodiment (described subsequently), scanning of the measurement points is also required. The number of scanning points is desirably 10 or more, and preferably 50 or more, 100 or more, 200 or more, 400 or more, and 800 or more.

In the above example, an increase in the speed of the sample motion is dealt with by shortening the wave number changing time interval. As another method of dealing with increases in the sample speed, shortening of the measurable range is also effective. More specifically, multiplying the wave number intervals (and frequency width) that appear in the top row of Table 1 by two and four correspond to respective cases where the sample speed is 2 mm/s or more and the sample speed is 4 mm/s or more.

Further, when the number of measurement points for scanning is n (n=10, 50, 100, 200, 400, or 800, for example) or more, the wave number changing time interval shown in (a) to (c) may be no more than 1/n, is as described above.

(D) The wavelength-tunable light generator for OCT that is described above is preferably constituted by a wavelength-tunable light-emitting element having the 'width of the tunable range of the wave number' and 'frequency width' that is described in B and C above and capable of changing the wave number stepwise at the 'wave number interval' and 'time interval' that is described in B and C above and a control circuit thereof. Further, the control circuit must change the wave number of the output light of the wavelength-tunable light-emitting element stepwise at the 'width of the tunable range of the wave number', the 'frequency interval', the 'wave number interval' and the 'time interval' above.

Alternatively, the wavelength-tunable light source generator for OCT may be a broadband light-emitting element having the 'width of the tunable range of the wave number' that appears in (B) or (C) above, a wavelength-tunable filter capable of extracting the output light out of the broadband light-emitting element stepwise in the 'width of the tunable range of the wave number', the 'frequency width', the 'wave number interval' and the 'time interval' that appear in (B) or (C) above, and a control circuit thereof.

(4) Fourth Invention

The first and second inventions can also be expressed as follows. That is, when the first and second inventions are expressed from another perspective, the fourth invention for resolving the above problem is a wavelength-tunable light generator that is used as a wavelength-tunable light source of an optical coherence tomography device comprising a wavelength-tunable light source, means for dividing the output light of the wavelength-tunable light source into a first light beam and a second light beam, means for irradiating a measurement object with the first light beam, means for combining the first light beam that has been reflected or backscattered by the measurement object and the second light beam, means for measuring the intensity of the output light combined by the means for combining each wave number of the wavelength-tunable light source, and means for specifying, in the depth direction of the measurement object, the position at which the first light beam is reflected by the measurement object from a set of intensities of output light obtained for each of the wave numbers by means of the means for measuring, wherein the width of the tunable range of the wave number is increased so that the resolution is no more than 80 µm and the frequency width and wave number interval of the emitted light are reduced so that the measurable range is at least 10 mm, the wavelength-tunable light generator further comprising: means capable of changing the wave number stepwise at time intervals of no more than the time obtained by dividing the first value obtained by dividing the resolution by the speed 1 mm/s by the second value obtained by dividing the width of the tunable range by the wave number interval.

(5) Fifth Invention

The first and third inventions can also be implemented as follows. That is, when the first and third inventions are expressed from another perspective, the fifth invention for resolving the above problem is a wavelength-tunable light generator that is used as a wavelength-tunable light source of an optical coherence tomography device comprising a wavelength-tunable light source, means for dividing the output light of the wavelength-tunable light source into a first light beam and a second light beam, means for irradiating a measurement object with the first light beam, means for combining the first light beam that has been reflected or backscattered by the measurement object, and the second light beam, means for measuring the intensity of the output light combined by the combining means for each wave number of the wavelength-tunable light source, and means for specifying, in the depth direction of the measurement object, the position and intensity with which the first light beam is reflected or backscattered by the measurement object from a set of intensities of the output light obtained for each of the wave numbers by means of the means for measuring, wherein the width of the tunable range of the wave number is increased so that the resolution is no more than 80 µm and the frequency width and wave number interval of the emitted light are reduced so that the measurable range is at least 10 mm, the wavelength-tunable light generator further comprising: means capable of changing the wave number stepwise at time intervals of no more than the time obtained by dividing the first value obtained by dividing the resolution by the speed 1 mm/s by a second value obtained by dividing the width of the tunable range by the wave number interval.

According to the fourth invention, the preferred value for the resolution is at least 40 µm or at least 20 µm. Further, a more preferable range for the measurable range is at least 100 mm or at least 1000 mm. In addition, a more preferable range for the speed, by which the resolution is divided, is no more than 3 mm/s or no more than least 9 mm/s. Further, when the number of measurement points for scanning is at least n (n=10, 50, 100, 200, 400, 800, for example), the wave number changing time interval may be no more than 1/n.

In the fifth invention, a more preferable value for the resolution is at least 40 µm or at least 20 µm. Further, a more preferable range for the measurable range is at least 5 mm. In addition, a more preferable range for the speed, by which the resolution is divided, is no more than 2 mm/s. Further, when the number of measurement points for scanning is at least n (n=10, 50, 100, 200, 400, 800, for example), the wave number changing time interval may be no more than 1/n.

(6) Sixth Invention

The wavelength-tunable light generator of the sixth invention is a wavelength-tunable light generator that is used as a wavelength-tunable light source of an optical coherence tomography device comprising a wavelength-tunable light source, means for dividing the output light of the wavelength-tunable light source into a first light beam and a second light beam, means for irradiating a measurement object with the first light beam, means for combining the first light beam that has been reflected or backscattered by the measurement object, and the second light beam, means for measuring the intensity of the output light combined by the means for combining for each of wave number of the wavelength-tunable light source, and means for specifying, in the depth direction of the measurement object the position and intensity with which the first light beam is reflected or backscattered by the measurement object from a set of intensities of the output light obtained for each of the wave numbers by means of the means for measuring, wherein the width of the tunable range of the wave number is increased so that the resolution is no more than 80 μm and the frequency width and wave number interval of the emitted light are reduced so that the measurable range is at least 2.5 mm, further comprising: means capable of changing the wave number stepwise at time intervals of no more than the time obtained by dividing the first value obtained by dividing the resolution by the speed 4 mm/s by a second value obtained by dividing the width of the tunable range by the wave number interval.

(7) Seventh Invention

The wavelength-tunable light generator of the seventh invention is the light source used by an OCT device according to the fourth to sixth inventions, wherein the means for irradiating a measurement object with the first light beam are capable of scanning an irradiation position at which the measurement object is irradiated with the first light beam, the wavelength-tunable light generator further comprising: means for constructing a tomogram of the measurement object on the basis of information specified by the means for specifying and information relating to the irradiation position. A tomogram of the measurement object can be efficiently obtained by providing means for irradiating the measurement object with the first light beam and the above specifying means, as described above.

(8) Eighth Invention

The wavelength-tunable light generator of the eighth invention is the wavelength-tunable light generator according to the first to seventh inventions, wherein the means for specifying subject a combination of real numbers comprising the intensity of the output light and the wave number to a Fourier transform. A high-speed Fourier transform (FFT) procedure capable of processing at an extremely high speed is established for the Fourier transform method and high-speed FD-OCT can be implemented by a FFT with data comprising combinations of real numbers.

(9) Ninth Invention

The wavelength-tunable light generator of the ninth invention is the wavelength-tunable light generator according to the first to eighth inventions, further comprising: means for constructing a motion image of a tomogram of the measurement object by constructing a plurality of the tomogram. The present invention permits high-speed measurement and, therefore, permits measurement of a tomogram motion image of the peristaltic movement of the digestive organ or a pulsating blood vessel or the like, and can be applied to medical diagnostics.

(10) Tenth Invention

The wavelength-tunable light generator of the tenth invention is the wavelength-tunable light generator according to the first to ninth inventions, wherein a light-emitting element constituting the wavelength-tunable light generator is a wavelength-tunable laser.

(11) Eleventh Invention

The wavelength-tunable light generator of the eleventh invention uses a super structure grating distributed Bragg reflector semiconductor laser as a light-emitting element constituting the wavelength-tunable light generator of the first to tenth inventions (See Patent Document 1, Patent Document 2, Non-Patent Document 4). A super structure grating distributed Bragg reflector semiconductor laser satisfies all the requirements for the wavelength-tunable light generator of the first invention above. That is, the wavelength tunable width exceeds 100 nm ($\Delta k=0.261$ $\mu m^{-1}$) and a high-speed response in which the wave number changing time interval is on the order of a few nanoseconds is also possible. Further, continuous wavelength sweeping is possible and the frequency width is a few MHz.

(12) Twelfth Invention

The wavelength-tunable light generator of the twelfth invention uses a sampled grating distributed Bragg reflector semiconductor laser as a light-emitting element constituting the wavelength-tunable light generator of the first to tenth inventions. A sampled grating distributed Bragg reflector semiconductor laser satisfies all the requirements of the wavelength-tunable light generator of the first invention. That is, the wavelength tunable width exceeds 100 nm ($\Delta k=0.261$ $\mu m^{-1}$) and a high-speed response in which the wave number changing time interval is on the order of a few nanoseconds is also possible. Further, a continuous wavelength sweeping is possible and the frequency width is a few MHz.

(13) Thirteenth Invention

The thirteenth invention is an OCT device, wherein the wavelength-tunable light generator for OCT of the first to twelfth inventions is used as the light source.

(14) Fourteenth Invention

The fourteenth invention is an OCT device, comprising: the wavelength-tunable light generator for OCT according to any one of the first to twelfth inventions; means for dividing the output light of the wavelength-tunable light generator into a first light beam and a second light beam; means for irradiating a measurement object with the first light beam; means for combining the first light beam that has been reflected or backscattered by the measurement object, and the second light beam; means for measuring the intensity of the output light combined by the means for combining for each of wave numbers of the wavelength-tunable light generator; and means for specifying, in the depth direction of the measurement object, the position at which the first light beam is reflected or backscattered by the measurement object from a set of the intensities of output light obtained for each of the wave numbers by means of the means for measuring. This OCT device uses the wavelength-tunable light generator of the first to twelfth inventions and is therefore capable of solving the above problems.

(15) Fifteenth Invention

The fifteenth invention is an OCT device, comprising: the wavelength-tunable light generator of any of the first to twelfth inventions; means for dividing the output light of the wavelength-tunable light generator into a first light beam and a second light beam; means for irradiating a measurement object with the first light beam; means for combining the first light beam that has been reflected or backscattered by the measurement object, and the second light beam; means for measuring the intensity of the output light combined by the means for combining for each of wave numbers of the wavelength-tunable light generator; and means for specifying, in the depth direction of the measurement object, the position and intensity with which the first light beam is reflected or backscattered by the measurement object from a set of intensities of the output light obtained for each of the wave numbers by means of the means for measuring.

Here, a variety of interferometers may be considered as the means for dividing the output light of the wavelength-tunable light generator into a first light beam and a second light beam, means for irradiating the measurement object with the first light beam, means for combining the first light beam reflected by the measurement object and the second light beam, the Michelson interferometer and Mach-Zehnder interferometer being representative examples. When a Mach-Zehnder-type interferometer is used, the light-collection efficiency is higher than that when using a Michelson interferometer.

(16) Sixteenth Invention

The sixteenth invention is the OCT device of the fourteenth or fifteenth invention, wherein the means for irradiating the measurement object with the first light beam are capable of scanning an irradiation position of the first light beam, further comprising: means for constructing a tomogram of the measurement object on the basis of information specified by the means for specifying and information relating to the irradiation position.

(17) Seventeenth Invention

The seventeenth invention is the OCT device according to the fourteenth or sixteenth invention, wherein the means for specifying subject a combination of real numbers comprising the intensity of the output light and the wave numbers to a Fourier transform.

(18) Eighteenth Invention

The eighteenth invention is the OCT device of the fourteenth to seventeenth inventions, further comprising: means for constructing a motion image of a tomogram of the measurement object by constructing a plurality of the tomogram.

(19) Nineteenth Invention

The nineteenth invention is an OCT device, comprising: the wavelength-tunable light generator according to any one of the first to third inventions; a sample optical path that guides output light of the wavelength-tunable light generator to a sample without dividing the output light; a partial reflection mechanism that returns a portion of the irradiated light of the sample optical path along the sample optical path; and an optical detection optical path that guides the reflected light and backscattered light from the sample along the sample optical path and the reflected light from the partial reflection mechanism to a photodetector.

When a light source that is capable of changing the wave number stepwise of the present invention is used, the coherence distance (coherent length) of the light source for each of the wave numbers can be at least 10 mm. In this case, even when a Michelson-type interferometer or Mach-Zehnder-type interferometer as used by a conventional OCT is not used, the OCT device can be implemented by placing a partial reflective mirror on a sample optical path whose distance from the sample is shorter than the coherence distance and causing interference between the reflected light from the partial-reflection mirror and the reflected or backscattered light from the sample.

In comparison with conventional methods that use an interferometer, the number of optical parts used can be markedly reduced, the fabrication costs can be lowered, and the device can be made more stable.

(20) Twentieth Invention

The twentieth invention is an OCT device, comprising: the wavelength-tunable light generator according to any one of the first to third inventions; a sample optical path that guides output light of the wavelength-tunable light generator to a sample without dividing the output light; a partial reflection mechanism that reflects a portion of the light of the sample optical path along the sample optical path after affording the portion of light a desired polarization characteristic; a sample light polarization-specifying mechanism that irradiates the sample with light that has been transmitted by the partial reflection mechanism in the sample optical path after affording the transmitted light the desired polarization characteristic; an optical detection optical path that guides the reflected light and backscattered light from the sample and the reflected light from the partial reflection mechanism to a polarization beam splitter, and means for detecting two outputs of the polarization beam splitter by using a photodetector and an amplifier respectively, and for data-processing the output data of the amplifier in order to construct a tomogram showing the polarization characteristic of the sample.

<B> Wavelength-Tunable Light Generator for Dental OCT and Dental OCT Device

(21) Twenty-First Invention

The wavelength-tunable light generator for dental OCT according to the twenty-first invention, which solves the above problems, comprises means the wavelength of which is in the range 0.9 to 5.0 µm that are capable of changing the wavelength stepwise, that is, the wavelength can be changed stepwise in the range 0.9 to 5.0 µm.

(22) Twenty-Second Invention

In the wavelength-tunable light generator for dental OCT of the twenty-second invention, the wavelength of the wavelength-tunable light generating means is in the range 0.9 to 5.0 µm, the width of the tunable range of the wave number is at least $4.7\times10^{-2}$ µm$^{-1}$ the frequency width of the emitted light is no more than 13 GHz. And the wavelength-tunable light generator for dental OCT comprises means of changing the wave number stepwise at wave number intervals of no more than $3.1\times10^{-4}$ µm$^{-1}$ and at the time intervals of no more than 530 µs. That is, in the twenty-first invention, the width of the tunable range of the wave number is at least $4.7\times10^{-2}$ µm$^{-1}$, the frequency width of the emitted light is no more than 13 GHz, the wave number interval is no more than $3.1\times10^{-4}$ µm$^{-1}$, and the wave number can be changed stepwise at time intervals of no more than 530 µs.

(23) Twenty-Third Invention

The light source of the dental OCT device of the twenty-third invention is the wavelength-tunable light-emitting device of the twenty-first or twenty-second invention, that is, the wavelength-tunable light generator for dental OCT of the twenty-first or twenty-second invention is used in the light source as wavelength-tunable light generating means.

(24) Twenty-Fourth Invention

The light source of the dental OCT device of the twenty-fourth invention is the wavelength-tunable light generator of the twenty-first or twenty-second invention and comprises means for measuring the polarization characteristic of a tooth, that is, polarization characteristic measurement means for measuring the polarization characteristic of a tooth are provided in the twenty-third invention.

(25) Twenty-Fifth Invention

The dental OCT device of the twenty-fifth invention is the dental OCT device according to the twenty-fourth invention, wherein the polarization characteristic measuring means comprise: main dividing means for dividing the light from the wavelength-tunable light generating means into measurement light and reference light with controlling the polarization direction of the light; measurement light irradiating means for irradiating a tooth in an oral cavity with the measurement light divided by the main dividing means; signal light collecting means for collecting signal light that is reflected by the tooth following irradiation of the tooth; combining means for separating the signal light collected by the signal light collecting means into components of two or more polarization directions and or respectively combining the separated light components with the reference light divided by the main dividing means; and computation control means for finding the polarization characteristic of the tooth on the basis of the intensity of the signal light of different polarization directions thus combined.

(26) Twenty-Sixth Invention

The dental OCT device of the twenty-sixth invention is the dental OCT device according to either the twenty-fourth or twenty-fifth invention, wherein the polarization characteristic measuring means comprise: main dividing means for dividing the light from the wavelength-tunable light generating means into measurement light and reference light; measurement light irradiating means for irradiating a tooth in an oral cavity with the measurement light divided by the main dividing means; signal light collecting means for collecting the signal light that is reflected by the tooth following the irradiation of the tooth; combining means for combining the signal light collected by the signal light collecting means and the reference light divided by the main dividing means; and computation control means for controlling the wavelength-tunable light generating means so that the light from the wavelength-tunable light generating means has the intended wavelength range and for finding the characteristics of the tooth on the basis of the wavelength range of the light from the wavelength-tunable light generating means and the intensity of the light combined by the combining means, wherein the computation control means control the wavelength-tunable light generating means so that light of a plurality of different wavelength ranges is output and find the characteristics of the tooth by finding the intensity of the light combined by the combining means for each wavelength range.

(27) Twenty-Seventh Invention

The dental OCT device of the twenty-seventh invention comprises: wavelength-tunable light generating means; main dividing means for dividing the light from the wavelength-tunable light generating means into measurement light and reference light; measurement light irradiating means for irradiating a tooth in an oral cavity with the measurement light divided by the main dividing means; signal light collecting means for collecting the signal light that is reflected by the tooth following the irradiation of the tooth; combining means for combining the signal light collected by the signal light collecting means and the reference light divided by the main dividing means; and computation control means for controlling the wavelength-tunable light generating means so that the light from the wavelength-tunable light generating means has the intended wavelength range and for finding the characteristics of the tooth on the basis of the wavelength range of the light from the wavelength-tunable light generating means and the intensity of the light combined by the combining means, wherein the computation control means control the wavelength-tunable light generating means so that light of a plurality of different wavelength ranges is output and find the characteristics of the tooth by finding the intensity of the light combined by the combining means for each wavelength range.

(28) Twenty-Eighth Invention

The dental OCT device of the twenty-eighth invention is the OCT device according to the twenty-sixth or twenty-seventh invention, wherein the computation control means find the light absorption coefficient of the tooth by finding the intensity of the light combined by the combining means for each wavelength range and find the characteristics of the tooth on the basis of the light absorption coefficient.

(29) Twenty-Ninth Invention

The dental OCT device of the twenty-ninth invention is the dental OCT device according to the twenty-eighth invention, wherein the computation control means find the abundance per unit volume of the composition of the enamel or dentine of the tooth on the basis of the light absorption coefficient.

(30) Thirtieth Invention

The dental OCT device of the thirtieth invention is the dental OCT device according to the twenty-ninth invention, wherein the computation control means further find the abundance of water concentration per unit volume of the enamel or dentine of the tooth on the basis of the light absorption coefficient.

(31) Thirty-First Invention

The dental OCT device of the thirty-first invention is the dental OCT device according to any of the twenty-third to thirtieth inventions, wherein the wavelength-tunable light generating means are wavelength-tunable semiconductor laser light generator.

(32) Thirty-Second Invention

The dental OCT device of the thirty-second invention comprises wavelength-tunable light generating means; main dividing means for dividing the light from the wavelength-tunable light generating means into measurement light and reference light; measurement light irradiating means for irradiating a tooth in an oral cavity with the measurement light divided by the main dividing means; signal light collecting means for collecting the signal light that is reflected by the tooth following the irradiation of the tooth; combining means for combining the signal light collected by the signal light collecting means and the reference light divided by the main dividing means; and computation control means for controlling the wavelength-tunable light generating means so that the light from the wavelength-tunable light generating means has the intended wavelength range and for finding the characteristics of the tooth on the basis of the wavelength range of the light from the wavelength-tunable light generating means and the intensity of the light combined by the combining means, wherein the wavelength-tunable light generating means are a wavelength-tunable semiconductor laser light generator.

(33) Thirty-Third Invention

The dental OCT device of the thirty-third invention is the dental OCT device according to the twenty-seventh or thirty-second invention, wherein the wavelength-tunable light generating means output light in a wavelength range between 1.2 µm and 5.0 µm.

(34) Thirty-Fourth Invention

The dental OCT device of the thirty-fourth invention is the dental OCT device according to the thirty-third invention, wherein the wavelength-tunable light generating means output light in a wavelength range wider than 1.3 µm to 1.6 µm within 1.2 µm and 5.0 µm.

(35) Thirty-Fifth Invention

The dental OCT device of the thirty-fifth invention is the dental OCT device according to the thirty-third or thirty-fourth invention, wherein the main dividing means and the combining means are combined to serve as main dividing and combining means.

(36) Thirty-Sixth Invention

The dental OCT device of the thirty-sixth invention is the dental OCT device according to any of the thirty-third to thirty-fifth inventions, wherein the measurement light irradiating means and the signal light collecting means are combined to serve as irradiating and collecting means.

(37) Thirty-Seventh Invention

The dental OCT device of the thirty-seventh invention is the dental OCT device according to the thirty-sixth invention, wherein the irradiating and collecting means comprise: an outer tube that is flexible and optically transparent at least at the leading end; a flexible inner tube that is laid within the outer tube so as to be capable of rotating in a circumferential direction and is formed with an I/O light window for the measurement light and the signal light at the leading end thereof; an optical fiber that is laid within the inner tube and that guides the measurement light and the signal light; and a probe that is provided at the leading end within the inner tube and that comprises connecting means for optically connecting the leading end of the optical fiber and the I/O light window of the inner tube.

(38) Thirty-Eighth Invention

The dental OCT device of the thirty-eighth invention is the dental OCT device according to thirty-seventh invention, wherein the probe comprises an observation mirror used for visual confirmation at the leading end of the outer tube.

(39) Thirty-Ninth Invention

The dental OCT device of the thirty-ninth invention is an OCT device which comprises a wavelength-tunable light generator capable of changing the wave number of light stepwise and which measures the structure in the depth direction of a measurement object by irradiating the measurement object with light that is output from the wavelength-tunable light generator and detecting reflected light or backscattered light that is produced within the measurement object by means of a detector, wherein the measurement object is biological tissue.

(40) The Fortieth Invention

The diagnostics method for the tissue constituting a human body according to the fortieth invention comprises the steps of: irradiating tissue constituting a human body with light output from the wavelength-tunable light generator according to any of the first to twelfth inventions; detecting reflected light or backscattered light that is produced within the tissue constituting a human body by means of a detector; and constructing, by means of an OCT, a tomographic image of tissue constituting the human body on the basis of detection data detected by the detector.

<C> Device for Measuring Tomogram of Various Structures such as a Biological Body or Coated Surface.

(41) Forty-First Invention

The wavelength-tunable light generator for optical coherence tomography of the forty-first invention comprises a light-emitting section that combines and outputs the outputs of a plurality of wavelength-tunable light sources of different wave number sweep ranges; and a control device that permits a wave number sweep in excess of the wave number sweep range of individual wavelength-tunable light sources by sweeping the wavelength-tunable light sources one at a time.

(42) Forty-Second Invention

The wavelength-tunable light generator for optical coherence tomography of the forty-second invention is the wavelength-tunable light generator for optical coherence tomography according to the forty-first invention, wherein the wavelength-tunable range is at least $0.2\ \mu m^{-1}$ in wave number.

(42) Forty-Third Invention

The wavelength-tunable light generator for optical coherence tomography of the forty-third invention comprises a light-emitting section that combines and outputs the outputs of a plurality of wavelength-tunable light sources of different sweep wave numbers; and a control device that permits a wave number sweep so that the wave numbers that can be output by the individual wavelength-tunable light sources supplement one another by sweeping the wavelength-tunable light sources one at a time.

(44) Forty-Fourth Invention

The wavelength-tunable light generator for optical coherence tomography of the forty-fourth invention is the wavelength-tunable light generator for optical coherence tomography according to the forty-first to forty-third inventions, wherein the plurality of wavelength-tunable light sources of different sweep wave numbers are capable of changing the wave number stepwise.

(45) Forty-Fifth Invention

The wavelength-tunable light generator for optical coherence tomography of the forty-fifth invention is the wavelength-tunable light generator for optical coherence tomography according to any of the forty-first to forty-fourth inventions, wherein the light-emitting section comprises an optical switch and the outputs are combined and output by the optical switch.

(46) Forty-Sixth Invention

The wavelength-tunable light generator for optical coherence tomography of the forty-sixth invention is the wavelength-tunable light generator for optical coherence tomography according to any of the forty-first to forty-fifth inventions, wherein the wavelength-tunable light source comprises a wavelength-tunable semiconductor laser.

(47) Forty-Seventh Invention

The optical coherence tomography device of the forty-seventh invention is an optical coherence tomography device, comprising: a wavelength-tunable light generator; means for dividing the output light of the wavelength-tunable light generator into measurement light and reference light; means for irradiating a measurement object with the measurement light and for collecting signal light produced as a result of the measurement light being reflected or backscattered by the measurement object; means for combining the signal light and the reference light; means for measuring the intensity of the output light combined by the combining means for each wave number of the wavelength-tunable light generator; and means for specifying, in the depth direction of the measurement object, the position at which the measurement light is reflected or backscattered by the measurement object and the reflection or backscatter intensity, from a set of intensities of the combined output light measured for each of the wave numbers by the measuring means. Further, the wavelength-tunable light generator is a wavelength-tunable light generator according to the forty-first to forty-sixth inventions.

(48) Forty-Eighth Invention

The optical coherence tomography device of the forty-eighth invention is the optical coherence tomography device according to the forty-seventh invention, wherein the dividing means and the combining means are the same means.

(49) Forty-Ninth Invention

The optical coherence tomography device of the forty-ninth invention is the optical coherence tomography device according to the forty-seventh or forty-eighth invention, comprising, instead of means for collecting the reflected or backscattered signal light: means for irradiating the measurement object with the measurement light; and means for collecting signal light produced as a result of the measurement light being reflected or backscattered by the measurement object.

(50) Fiftieth Invention

The optical coherence tomography device of the fiftieth invention is the optical coherence tomography device according to any of the forty-seventh to forty-ninth inventions, wherein the specifying means subject a combination of real numbers comprising the intensity of the output light and the wave number to a Fourier transform.

(51) Fifty-First Invention

The optical coherence tomography device of the fifty-first invention employs the wavelength-tunable light generator according to any of the forty-first to forty-sixth inventions.

(52) Fifty-Second Invention

The optical coherence tomography device of the fifty-second invention is the optical coherence tomography device according to any of the forty-seventh to fiftieth inventions, wherein the specifying means correct the fluctuations in the intensity with respect to the wave number of the output light of the wavelength-tunable light generator.

(53) Fifty-Third Invention

The optical coherence tomography device of the fifty-third invention is the optical coherence tomography device according to any of the forty-seventh to fiftieth inventions or the fifty-second invention, wherein the specifying means correct the intensity of the output light by using a window function.

(54) Fifty-Fourth Invention

The wavelength-tunable light generator for optical coherence tomography of the fifty-fourth invention combines and outputs the outputs of a plurality of wavelength-tunable light sources of a different frequency sweep range or sweep wave number.

(55) Fifty-Fifth Invention

The optical coherence tomography device of the fifty-fifth invention is the optical coherence tomography device according to any of the forty-seventh to fiftieth inventions, wherein the specifying means subject a combination of real numbers comprising the intensity of the combined output light and the wave number to a Fourier transform.

(56) Fifty-Sixth Invention

The optical coherence tomography device of the fifty-sixth invention is the optical coherence tomography device according to the fifty-fifth invention, wherein the specifying means correct the intensity of the combined output light so as to eliminate the effect of fluctuations in the intensity with respect to the wave number of the output light of the wavelength-tunable light source generator.

(57) Fifty-Seventh Invention

The optical coherence tomography device of the fifty-seventh invention is the optical coherence tomography device according to the fifty-sixth invention, wherein the correction is performed by multiplying a reciprocal number of a value that is obtained by sequentially measuring the intensity of the output light of the wavelength-tunable light generator each time the wave number is changed during the measurement by the optical coherence tomography device, or a numerical value that is proportional to the reciprocal number, by the intensity of the combined output light.

(58) Fifty-Eighth Invention

The optical coherence tomography device of the fifty-eighth invention is the optical coherence tomography device according to the fifty-sixth invention, wherein the correction is performed by multiplying a reciprocal number of a value that is obtained by pre-measuring, for each of the wave numbers, the intensity of the output light of the wavelength-tunable light source generator, or a numerical value that is proportional to the reciprocal number, by the intensity of the combined output light.

(59) Fifty-Ninth Invention

The optical coherence tomography device of the fifty-ninth invention is the optical coherence tomography device according to any of the fifty-fifth to fifty-eighth inventions, wherein the specifying means use a window function to modify the intensity of the combined output light or the intensity of the combined output light corrected so as to eliminate the effect of fluctuations in the intensity with respect to the wave number of the output light of the wavelength-tunable light generator.

(60) Sixtieth Invention

The optical coherence tomography device of the sixtieth invention is the optical coherence tomography device according to the fifty-fifth invention, wherein the specifying means correct the combined output light so as to obtain the same measurement result as the measurement result obtained when the intensity distribution with respect to the wave number of the output light of the wavelength-tunable light generator matches a desired window function.

EFFECTS OF INVENTIONS

<A> Wavelength-Tunable Light Generator and OCT Device

The present invention focuses attention on the fact that the wavelength-tunable light generator can be provided by a light source the wavelength of which can be changed at high speed (a semiconductor laser, for example) and permits tomographic observation, which is difficult with conventional OCT, of biological body parts hard to constrain by means of constructing an interferogram by wave number-scanning provided by the wavelength-tunable light generator. Further, tomographic observation is made possible, that removes the burden of constraint on the biological body by removing constraint even in the observation of constrainable parts. Thereupon, an adequate resolution and measurable range can also be secured by limiting the tunable wave number width, wave number interval, and frequency width, whereby efficient measurement is made possible.

In addition, the present invention permits the imaging of tomograms of moving parts such as digestive organs in peristaltic motions or a pulsating blood vessel or the like and, therefore, video imaging is made possible by continuously imaging these parts.

Therefore, this invention is the invention of new OCT devices and light sources thereof that scan wave numbers stepwise, and also the invention of use for the devices (or the light sources) as tomographic devices (or light sources) of biological body parts that are difficult to constrain. Likewise, the present invention can be said to be the invention of use as tomographic video-recording devices (or light sources) for biological parts in motion as a result of biological activity.

<B> Wavelength-Tunable Light Generator for Dental OCT and Dental OCT Device

The wavelength-tunable light generator for dental OCT and dental OCT device according to the present invention permit a light source that emits light in a longer wavelength range than the prior art, which is required to obtain a deeper penetration range, and also permit a device for OCT measurements by using the light source. Furthermore, because the measurement sensitivity increases, measurement can be achieved at a deeper penetration depth.

Further, by the OCT measurement device that also permits measurement of the polarization characteristic, a tomogram of the tissue of teeth that possesses birefingence like enamel, for example, can also be made clear.

Furthermore, because this is an OCT device capable of spectral measurement, this OCT device is also capable of measurement of the compositional ratio of the constituent substances, whereby more accurate diagnostic knowledge is obtained than that of an OCT device that measures only the intensity as the prior art.

Further, because this is an OCT device that implements a faster measurement speed than a conventional OCT device, distortion (artifacts) of the tomographic image caused by motion of the tooth as the measurement object during the measurement time can be reduced.

Accordingly, the cavity detecting device of the present invention is able to perform detection easily even in the case of a minute early stage cavity.

<C> Device for Measuring a Tomogram of Various Structures such as Biological Body or Coated Surface.

The present invention is produced by combining a new switching light source rendered by combining wavelength-tunable light sources, and an OFDR-OCT device. Unlike a combined light source, the new switching light source affords the effect that the resolution of the OCT signal increases inversely proportional to the optical spectral width expanded by using a plurality of light sources. Further, the problem of an increase in the side lobes seen with a combined light source is absent.

BRIEF DESCRIPTION OF THE DRAWINGS

FIG. 1(A) shows the procedure of the stepwise change of the wave number of the wavelength-tunable light generator for OCT of the present invention, in which the wave number is changed stepwise to increase gradually with the sweeping time;

FIG. 1(B) shows the procedure of the stepwise change of the wave number of the wavelength-tunable light generator for the OCT of the present invention, in which the wave number is changed stepwise to increase irregularly with the wave number sweeping time;

FIG. 22 is a schematic drawing of a probe of another embodiment of the dental OCT device of the present invention;

FIG. 24 are FD-OCT images of a person's extracted canine tooth;

FIG. 25(a)-(c) is an explanatory diagram of the method of scanning the wavelength of the light emitted from the wavelength-tunable light generator;

FIG. 36(a) shows an example of an OCT device that uses a combined light source and FIG. 36(b) shows an example of an OCT device that uses a wavelength-tunable light source with extremely narrowband width;

BEST MODE FOR CARRYING OUT THE INVENTION

Figure 2:
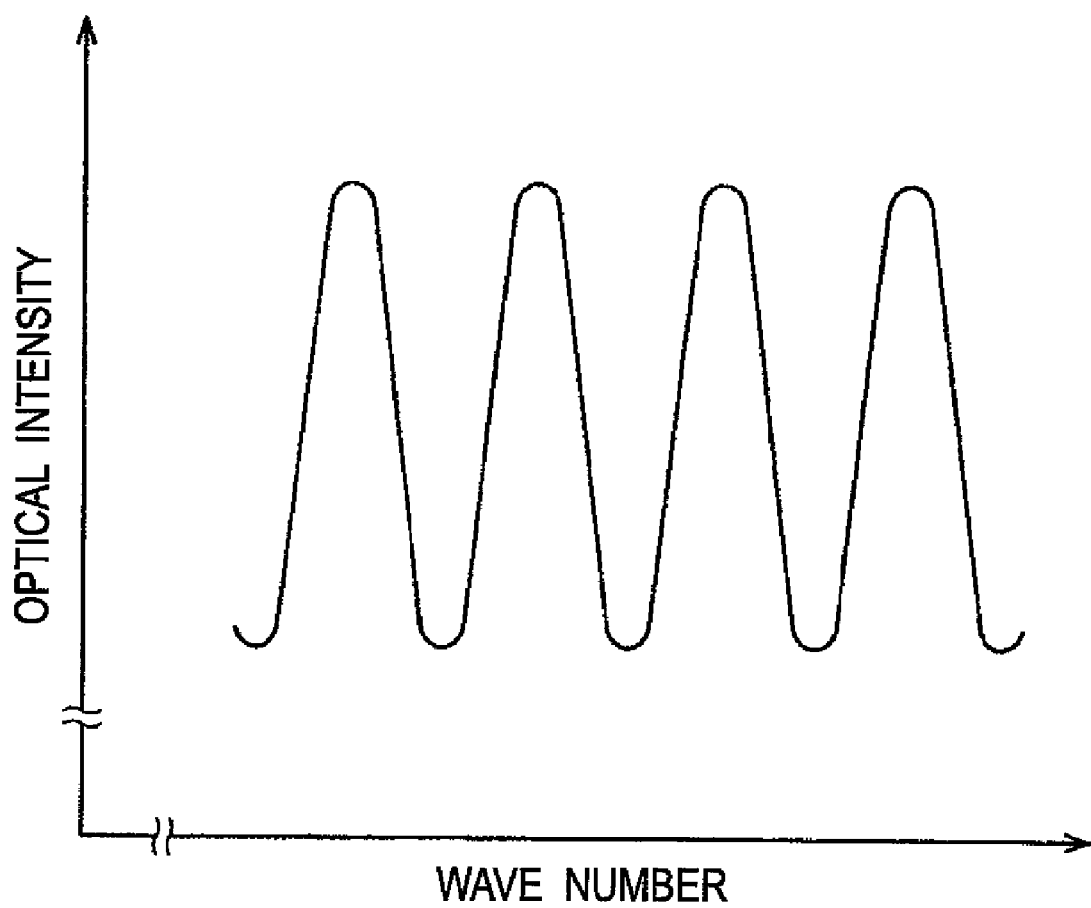
FIG. 2 shows a spectroscopic characteristic obtained by collecting the output optical intensities of the interferometer for each of the wave number.

<A> wavelength-Tunable Light Generator and OCT Device

First Embodiment

An example of the OCT device of the present invention will be described with reference to FIG. 3. The OCT device shown in FIG. 3 comprises a wavelength-tunable light generator 31 as a wavelength-tunable light source. The wavelength-tunable light generator 31 is constituted by a super structure grating distributed Bragg reflector semiconductor laser and control circuit thereof. The wavelength-tunable range of the wavelength-tunable light generator 31 is from 1533.17 to 1574.14 nm ($W_k = 1.07 \times 10^{-1}$ $\mu m^{-1}$) and the spectral frequency width is no more than 10 MHz. The scanning speed is 1 μs per chip and the scanning of 400 wave numbers is performed. Therefore, the wave number interval per step is $2.67 \times 10^{-4}$ μm. Because scanning of 400 wave numbers is performed at the scanning speed 1 μs/step, measurement time of the A scan (scanning in only the depth direction) is 0.4 ms and, when a B scan (scanning of the measurement points in the transverse direction while repeating A scans) includes 50 A scans, the measurement time is 20 ms.

When the static resolution is determined from Equation (2), $\Delta Z = 36$ μm. In this case, the resolution in a biological body with a refractive index of 1.36 is 26 μm. The refractive index depends on the composition of the sample and, therefore, the effect of the refractive index on the resolution is not considered in the present invention. As mentioned earlier, the refractive index of biological body is not so large and, therefore, even when the effect of the refractive index is ignored, the results obtained are substantially the same. Even if the biological sample moves at 1 mm/s, the distance moved by the sample during a B scan is only 20 μm and is relatively small in comparison with the static resolution of 36 μm, whereby degradation of the dynamic resolution does not occur. Further, the measurable range is determined by the wave number interval and is 12 mm as shown in Equation (4). Further, the measurable range computed from the instantaneous frequency width is 13 m (See Equation (3)).

The light emitted from the wavelength-tunable light generator 31 is divided into two in the ratio 90:10 by a first coupler 32. Here, one of the divided light components (90% division percentage) is further divided into two in the ratio 70:30 by the second coupler 33. Further, one of the divided light components (measurement light: 70% division percentage) is guided to a sample 37 constituting the measurement object by an optical circulator 34 and signal light 45 from the sample 37 is guided to a third coupler 38 by the optical circulator 34. The other (reference light: 30% division percentage) of the light components divided by the second coupler 33 is guided to the other input port of the third coupler 38 and combined with the signal light 45.

A Mach-Zehnder-type interferometer is made possible using the optical circulator 34. A B scan for obtaining a tomogram is performed by scanning measurement light over the surface of the sample 37 by means of a scanning mirror 36 between the optical circulator 34 and the sample 37. Further, the first, second, and third couplers 32, 33, and 38 are directional couplers. The output of the third coupler 38 is detected by a first differential amplifier 39 with optical detection function.

Because the third coupler 38 is a directional coupler, the two outputs $I_{o1}$ and $I_{o2}$ of the third coupler 38 are as follows. The first differential amplifier 39 detects the difference between the two outputs $I_{o1}$ and $I_{o2}$ of the third coupler 38 and outputs a log thereof. The first equation of Equation (7) is a well-known equation that represents the interference pattern when the optical path length difference is 2L. The second equation of Equation (7) is obtained from the property of the directional coupler.

(Equation 18)

$$2I_{o1} = I_r + I_s + 2\sqrt{I_r I_s} \cos(2Lk_n) \\ 2I_{o2} = I_r + I_s - 2\sqrt{I_r I_s} \cos(2Lk_n) \Bigg\} \quad (7)$$

Here, $k_n$ is the wave number of the emitted light of the wavelength-tunable light generator 31, $I_r$ is the intensity of the reference light 46 (the light guided directly to the third coupler 38 instead of being guided to the sample 37 by the optical circulator 34 among the light components divided by the second coupler 33: 30% division percentage), $I_S$ is the intensity of the signal light 45 from the sample 37, and 2L is the optical path length difference between the reference light 46 and the signal light 45 (in the case of a Michelson interferometer, the optical path length of the reference mirror and beam splitter is $L_r$, and when the optical path length between the reflective faces within the sample and the beam splitter is $L_S$, $L = L_S - L_r$).

Therefore, L corresponds to the coordinate in the depth direction of the sample. Further, in order to simplify the explanation, there is only one reflection point within the sample 37 and the phase shift accompanying the reflection is ignored. Incidentally, because the phase shift accompanying the reflection is no more than π, the difference in optical path length is no more than one half of the wavelength and can be ignored.

The Log output signal of the first differential amplifier 39 is input to a second differential amplifier 40. The other of the light components divided by the first coupler 32 (10% division percentage) passes through a Log amplifier 43 after being detected by a photodetector 42 and is guided to the second differential amplifier 40. The second differential amplifier 40 performs division to correct the fluctuations in the input light intensity. Hence, the output of the second differential amplifier 40 is expressed by Equation (8) below (the constant term is omitted).

(Equation 19)

$$\log\left[\sqrt{\frac{I_s}{I_r}} \cos(2Lk_n)\right] \quad (8)$$

The output of the second differential amplifier 40 is input to an analog/digital converter (not shown), whereupon the digital output thereof is guided to a data processor 41 to be processed thereby and interferograms are combined. The data processor 41 calculates a tomogram of the sample 37 from the interferograms. The data processor 41 also performs control of the wavelength-tunable light generator 31 and scanning mirror 36 at the same time.

Figure 4:
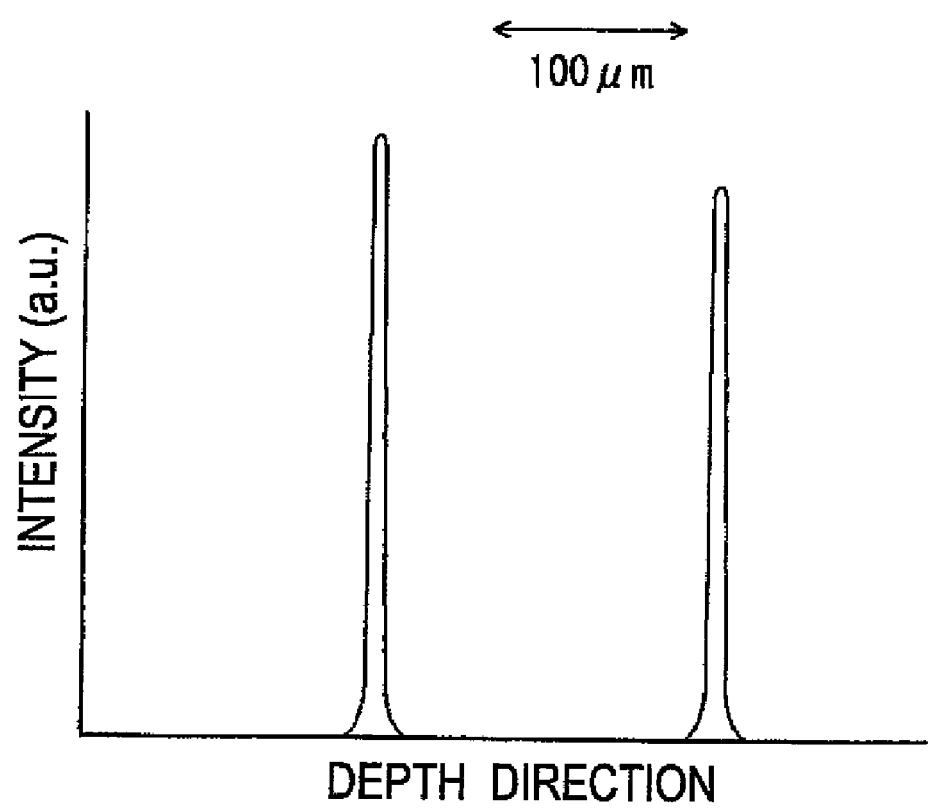
FIG. 4 shows an example in which an interferogram is obtained by the OCT device.

FIG. 4 shows an example of the combined interferograms. The result is an interferogram of cover glass 160 μm thick serving as the sample 37. Two peaks correspond to reflection from the upper and rear faces of the sample 37.

With such a device configuration, tomography is also possible for organs that have been conventionally difficult to constrain such as the digestive organs. Further, video imaging is also made possible by continuously imaging tomograms. The construction of the video image is performed by the data processor 41.

Figure 5:
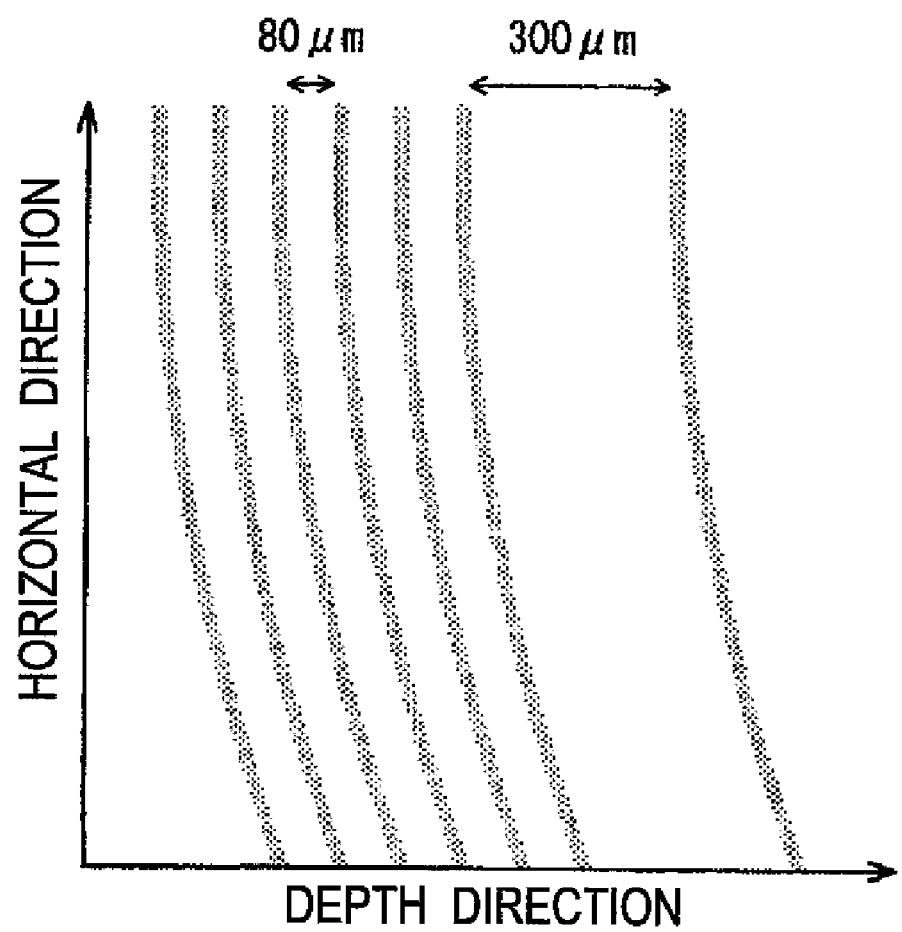
FIG. 5 shows the results of tomography of human nail as the measurement object.

FIG. 5 shows the result of tomogram of a human's nail as the measurement object. It can be seen that, from the surface of the nail, five layers about 80 μm thick were identified followed by a layer about 300 μm thick. Although securing of the sample finger was not performed during measurement, a clear image without blurring was obtained.

The first embodiment of the present invention uses a Mach-Zehnder-type interferometer and, therefore, a B scan was required to obtain a tomogram. However, because the light collecting efficiency is high and the measurement light can be guided close to the sample by an optical fiber, handling of the system is easy. Further, the fiber source coupler (trade name)

Figure 3:
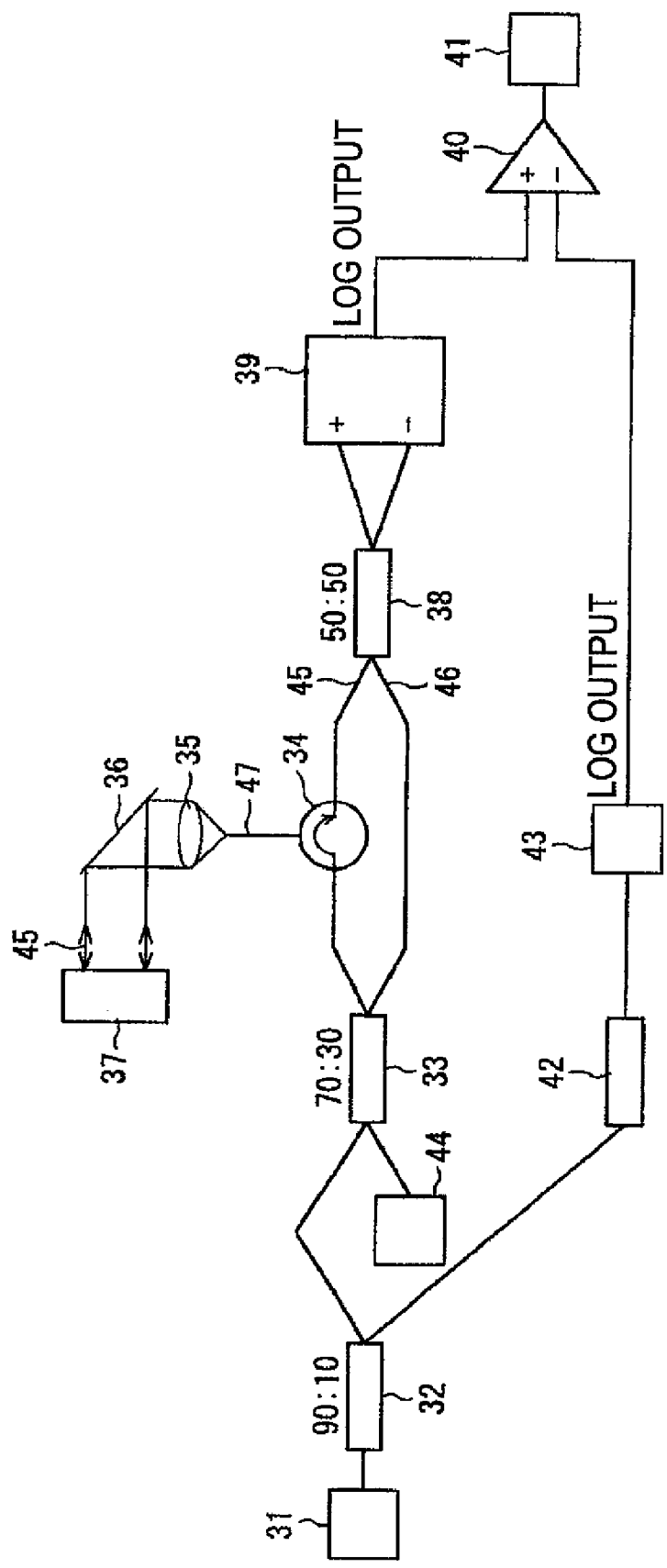
FIG. 3 shows an example of the configuration of the OCT device of the present invention.

35 shown in FIG. 3 is a so-called collimator set between the optical circulator 34 and scanning mirror 36. The fiber source coupler 35 makes the divergent light out of the optical fiber 47 parallel, and at the same time focuses the signal light 45 (parallel light) from the sample 37 and coupled to the optical fiber 47. Further, visible light that is output from an aiming light source 44, which is a visible light source, is also guided to and irradiated onto the sample 37 via the second coupler 33, the optical circulator 34, the fiber source coupler 35, and the scanning mirror 36, and as the result, the position of the measurement light on the sample 37 can be confirmed visually prior to a measurement.

The light-emitting element for the wavelength-tunable light generator 31 is not limited to a super structure grating distributed Bragg reflector semiconductor laser. Although the tunable wave number width is narrow, a distributed Bragg reflector laser (DBR) can also be used. Furthermore, otherwise, wavelength-tunable lasers include a laser known as a sampled grating distributed Bragg reflector semiconductor laser (the wavelength-tunable laser in U.S. Pat. No. 4,895,325, for example). The wave number switching time of these lasers accelerated up to a few ns.

Principle

The principle of the data processing performed in order to obtain an interferogram is as follows. The term in log of Equation (8) is derived from the square root of $I_s/I_r$ and the cos term. Here, $I_s/I_r$ is considered to be a constant because the $k_n$ dependency is small. Therefore, by data processing the output of the second differential amplifier 40 and removing the log, an output $I_d$ proportional to the $\cos(2L \cdot k_n)$ can be obtained. When the output $I_d$ at all the $k_n$ is measured, Fourier transform is performed on them, and an absolute value is adopted, a function with a sharp peak at the position x=2L is obtained. That is, the value 2L, which expresses the position of the reflective face within the sample, can be obtained by subjecting the output $I_d$ to a Fourier transform. It is shown hereinafter that the absolute value of the Fourier transform is a function with a sharp peak at the position x=2L. The cos component $Y_c(x)$, sin component $Y_s(x)$ and absolute value $Y_t(x)$ of the Fourier transform for the output $I_d$ are respectively expressed by Equations (9), (10), (11), and (12) below (Here, proportionality coefficient is omitted. The same is true below).

(Equation 20)

$$Y_c(x) = \sum_{n=1}^{N} \cos(k_n x)\cos(2Lk_n) \quad (9)$$

$$Y_s(x) = \sum_{n=1}^{N} \sin(k_n x)\cos(2Lk_n) \quad (10)$$

$$Y_t(x) = \sqrt{Y_c^2(x) + Y_s^2(x)} \quad (11)$$

$$k_n = k_s + \Delta k \cdot n \quad (12)$$

Here, $k_s$ represents the starting point of the wave number scanning range, n is a natural number, and N represents the total number of wave numbers scanned.

First, the cos component $Y_c(x)$ will be considered.

Equations (13) and (14) below are derived from a mathematical formula.

(Equation 21)

$$\cos\alpha\cos\beta = \frac{1}{2}[\cos(\alpha+\beta) + \cos(\alpha-\beta)] \quad (13)$$

$$= \frac{1}{4}[e^{j(\alpha+\beta)} + e^{-j(\alpha+\beta)} + e^{j(\alpha-\beta)} + e^{-j(\alpha-\beta)}]$$

$$\sum_{n=1}^{N} e^{jn\gamma} = \frac{e^{j\gamma} - e^{j(N+1)\gamma}}{1 - e^{j\gamma}} \quad (14)$$

$$= \frac{e^{j(\frac{N}{2}+1)\gamma}}{e^{j\frac{\gamma}{2}}} \cdot \frac{\frac{e^{j\frac{N}{2}\gamma} - e^{-j\frac{N}{2}\gamma}}{2}}{\frac{e^{j\frac{\gamma}{2}} - e^{-j\frac{\gamma}{2}}}{2}}$$

$$= e^{j\frac{N+1}{2}\gamma} \frac{\sin\left(\frac{N}{2}\gamma\right)}{\sin\left(\frac{1}{2}\gamma\right)}$$

To perform calculation for deriving Equation (9), Equations (13) and (14) are used. Further, j is an imaginary unit. First, the substitutions $\alpha=x\times k_n$, $\beta=2L\times k_n$ are made in Equation (13) and substituted in Equation (9). Equation (13) comprises four terms but $\Sigma$ is first computed for only the first two terms. Equation (14) is used in the computation of $\Sigma$. Thereupon, the substitution $\gamma=(x+2L)\times\Delta k$ is made and the relational expressions $jx(\alpha+\beta)=jx(x+2L)\times k_n=j(x+2L)\times(k_s+\Delta k \cdot n)=j(x+2L)\times k_s+j(x+2L)\cdot\Delta k \cdot n=j(x+2L)\times k_s+j\cdot\gamma\cdot n$ are used. Finally, the equation is simplified when $\cos(x)=[\exp(jx)+\exp(-jx)]/2$ is used. Equation (15) below is obtained when a similar procedure is also performed for the following two terms.

(Equation 22)

$$Y_c(x) = \frac{1}{2}\cos\left[\frac{(x+2L)}{2}\left(k_s + \frac{N+1}{2}\Delta k\right)\right]\frac{\sin\left[\frac{(x+2L)}{2}N\Delta k\right]}{\sin\left[\frac{(x+2L)}{2}\Delta k\right]} + \quad (15)$$

$$\frac{1}{2}\cos\left[\frac{(x-2L)}{2}\left(k_s + \frac{N+1}{2}\Delta k\right)\right]\frac{\sin\left[\frac{(x-2L)}{2}N\Delta k\right]}{\sin\left[\frac{(x-2L)}{2}\Delta k\right]}$$

Likewise, the sin component $Y_s(x)$ is also derived as Equation (16) below.

(Equation 23)

$$Y_s(x) = \frac{1}{2}\sin\left[\frac{(x+2L)}{2}\left(k_s + \frac{N+1}{2}\Delta k\right)\right]\frac{\sin\left[\frac{(x+2L)}{2}N\Delta k\right]}{\sin\left[\frac{(x+2L)}{2}\Delta k\right]} + \quad (16)$$

$$\frac{1}{2}\sin\left[\frac{(x-2L)}{2}\left(k_s + \frac{N+1}{2}\Delta k\right)\right]\frac{\sin\left[\frac{(x-2L)}{2}N\Delta k\right]}{\sin\left[\frac{(x-2L)}{2}\Delta k\right]}$$

Although Equations (15) and (16) both contain the terms of Equations (17) and (18) below, these equations have large values when x=2L or x=−2L but otherwise small values.

(Equation 24)

$$\frac{\sin\left[\frac{(x+2L)}{2}N\Delta k\right]}{\sin\left[\frac{(x+2L)}{2}\Delta k\right]} \quad (17)$$

$$\frac{\sin\left[\frac{(x-2L)}{2}N\Delta k\right]}{\sin\left[\frac{(x-2L)}{2}\Delta k\right]} \quad (18)$$

Meanwhile, the coefficient of these terms is a trigonometric function that oscillates between −1 and +1. Therefore, an approximate is obtained if the absolute values of the Fourier transform are substituted in Equation (11) by discriminating the terms of Equation (17) from Equations (15) and (16) in the neighborhood of x=−2L and the terms of Equation (18) from Equations (15) and (16) in the neighborhood of =2L. Therefore, the following equation (19) results in the neighborhood of x=−2L.

(Equation 25)

$$Y_t(x) \propto \left|\frac{\sin\left[\frac{(x-2L)}{2}N\Delta k\right]}{\sin\left[\frac{(x-2L)}{2}\Delta k\right]}\right| \quad (19)$$

That is, the position of the reflective face within the measurement object is specified from a set of output light intensities obtained for each of the wave numbers. Because one optical intensity is required for each wave number in such specification, the measurement time can be shortened in comparison with conventional FD-OCT.

Figure 6:
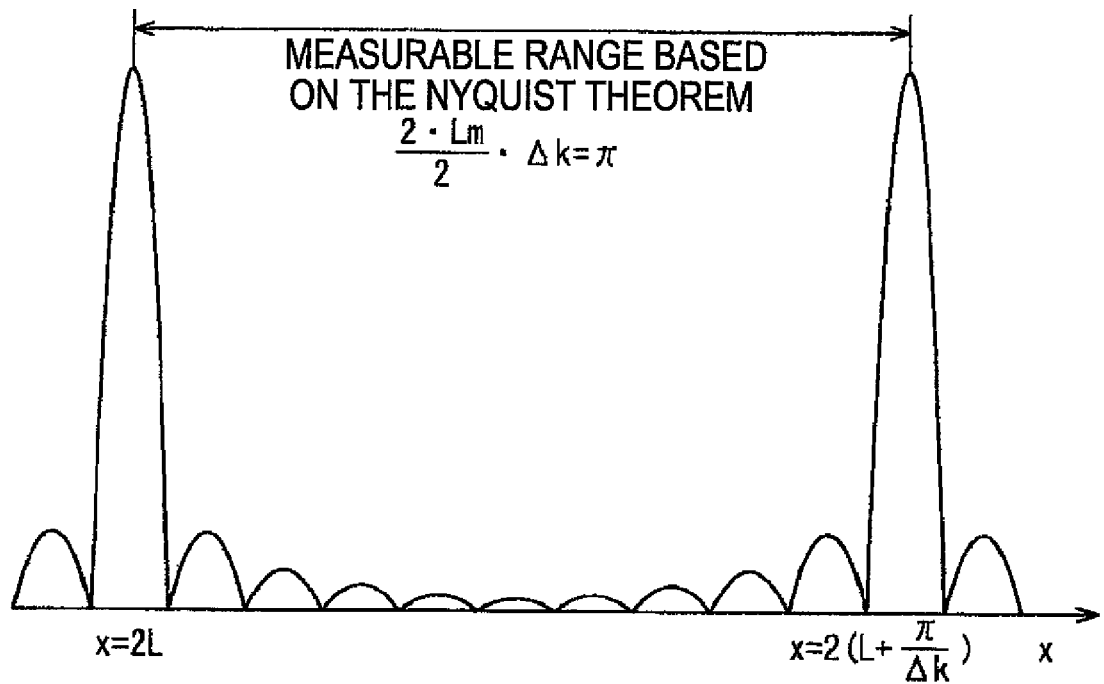
FIG. 6 is an explanatory diagram of the measurable range.
Figure 7:
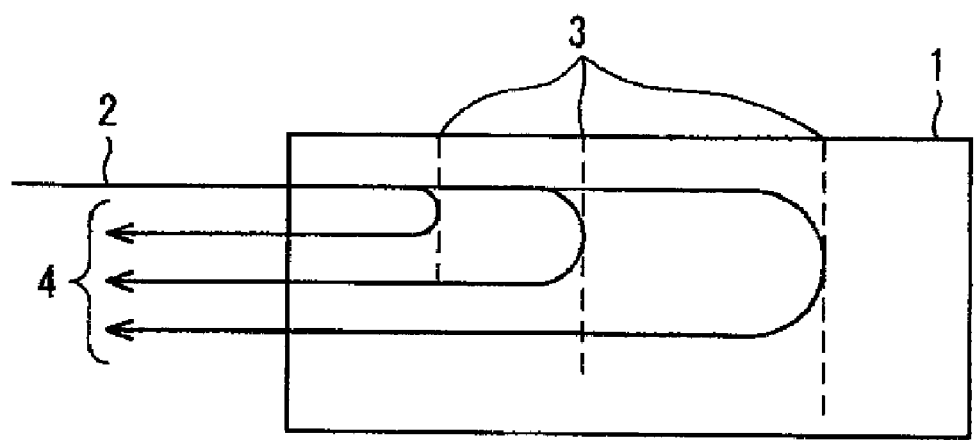
FIG. 7 shows the principle of OCDR-OCT measurement.

Equation (19) is a periodic function for x, and the period is determined by the sin function of the denominator of Equation (19) (FIG. 6). According to the Nyquist theorem, the measurable range $L_m$ is expressed by Equations (20) and (21) below.

(Equation 26)

$$2\frac{L_m}{2}\cdot\Delta k = \pi \quad (20)$$

That is, $$L_m = \frac{\pi}{\Delta k} \quad (21)$$

Further, Equation (19) takes a maximum value at x=2L, this value being N. That is, the peak value of interferogram obtained by the present invention increases proportional to N. Further, it can be seen from Equations (7) and (18) that the proportional constant is two times the square root of $I_r \times I_s$. On the other hand, the peak of OCDR-OCT is obtained at the point where there is a match between the phases of the reference light and signal light and, therefore, the product of the reference light intensity $I_r$ and the signal light intensity $I_s$, that is, two times the square root of $I_r \times I_s$.

Therefore, the peak value of interferogram obtained by the present invention is N times the peak of OCDR-OCT, where N is the total number of wave numbers used in the measurement, which is normally several hundred to several thousand. Hence, the interferogram obtained by the present invention is several hundred or several thousand times larger than that obtained by OCDR-OCT.

Meanwhile, because conventional FD-OCT also uses a Fourier transform, the interferogram proportional to the total number N of measurement wave numbers. However, when divided into N by a diffraction grating, the output light of the interferometer is weakened by the diffraction efficiency of the diffraction grating. Hence, the interferogram do not increase to the level of ED-OCT. In addition, because the light from the light source is expanded in the y direction, the interferogram becomes even smaller. Therefore, the interferogram obtained by the present invention is larger even compared with conventional FD-OCT.

Further, the resolution of the device of the present invention is derived from Equation (19). sin(x) can be approximated by x in the neighborhood of x=0 and it is therefore clear that the value of Equation (19) for x=2L is N. Hence, if Equation (22) below is solved for x, the full width at half maximum, that is, the resolution $\Delta Z$, is known. Further, due to the existence of the terms of Equation (17), $Y_t(x)$ also takes a large value at the position x=2π/Δk−2L. Therefore, a ghost appears in this position. There is no problem when the ghost can be easily identified due to the properties of the measurement object. However, when the ghost cannot be easily identified, $L_m$ must be increased by reducing the wave number interval.

(Equation 27)

$$\frac{\sin\left[\frac{X}{2}N\Delta k\right]}{\sin\left[\frac{X}{2}\Delta k\right]} = \frac{N}{2} \quad (22)$$

Here, the approximation formula (23) below is substituted into Equation (22) and Equation (24) is obtained upon solving by numerical analysis.

(Equation 28)

$$\sin\left(\frac{X}{2}\Delta k\right) \cong \frac{X}{2}\Delta k \quad (23)$$

$$\frac{X}{2}N\Delta k = 1.89549 \quad (24)$$

Equation (25) for the resolution is obtained by this equation.

(Equation 29)

$$\Delta Z = X = \frac{2 \times 1.89549}{N\Delta k} = \frac{3.79}{W_k} \quad (25)$$

Further, the resolution is the half width at half maximum with respect to x, but it is the full width at half maximum with respect to L, which corresponds to the coordinate in the depth direction of the sample.

If the phase difference between the measurement light and the reference light can be found, information on the light that is backscattered (or reflected) can be completely obtained and, therefore, the backscattering position (or reflection position) and the intensity thereof can be easily found. However, as mentioned earlier, the present invention only subjects a combination of real numbers comprising the intensity of the output light and the wave number to a Fourier transform. That is, the present invention is characterized in that, even when the phase difference between the measurement light and reference light is not measured, measurement of the backscattering position and the intensity thereof is possible and a complex device configuration for the purpose of measuring the phase difference is not necessary.

Second Embodiment

The configuration of the OCT device of the second embodiment is the same as that of FIG. 3. Further, in the second embodiment, the wavelength-tunable range of the wavelength-tunable light generator 31 is from 1511.74 to 1588.26 nm ($W_k=2.0\times10^{-1}$ µm) and the spectral frequency width is no more than 10 MHz. The scanning speed is 2 ns/step and the scanning of 8000 wave numbers is performed. Therefore, the wave number interval per step is $2.5\times10^{-5}$ µm.

Because scanning of 8000 wave numbers is performed at a scanning speed of 2 ns/step, the measurement time of an A scan (scan in only the depth direction) is 16 µs and, when a B scan (scanning of the measurement points in the horizontal direction that is performed while repeating an A scan) is constituted by 800 A scans, the measurement time is 13 ms. When the static resolution $\Delta Z$ is determined from Equation (2), $\Delta Z=19$ µm. Even if an biological sample moves at 1 mm/s, the distance displaced by the sample during a B scan is only 13 µm and is relatively small in comparison with the static resolution 19 µm, whereby degradation of the dynamic resolution does not occur.

Further, the measurable range is decided by the wave number interval and is 130 mm as can be seen from Equation (4). Further, the measurable range computed from the frequency width is 13 mm (See Equation (3)). Because the measurable range is sufficiently wide at 130 mm or more, even when the measurement points are changed, the reference mirror position need not be adjusted.

Figure 8:
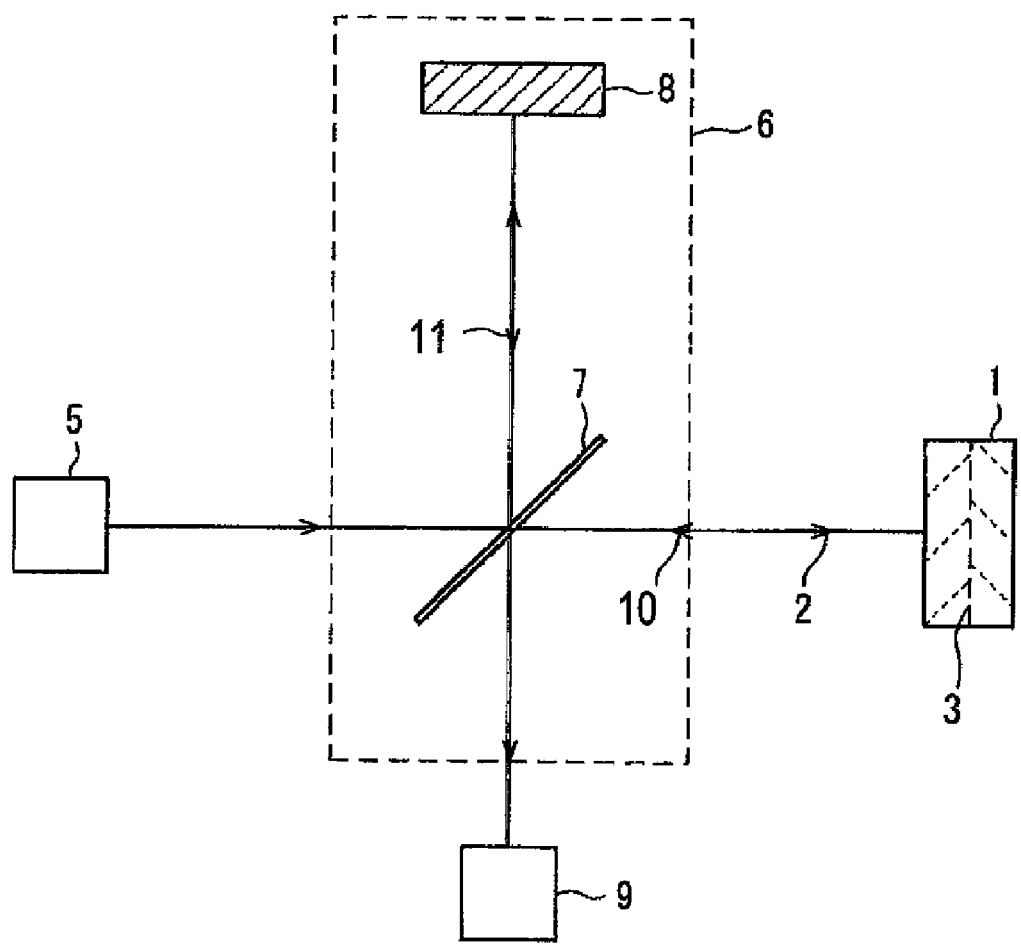
FIG. 8 shows the configuration of an OCDR-OCT device.
Figure 9:
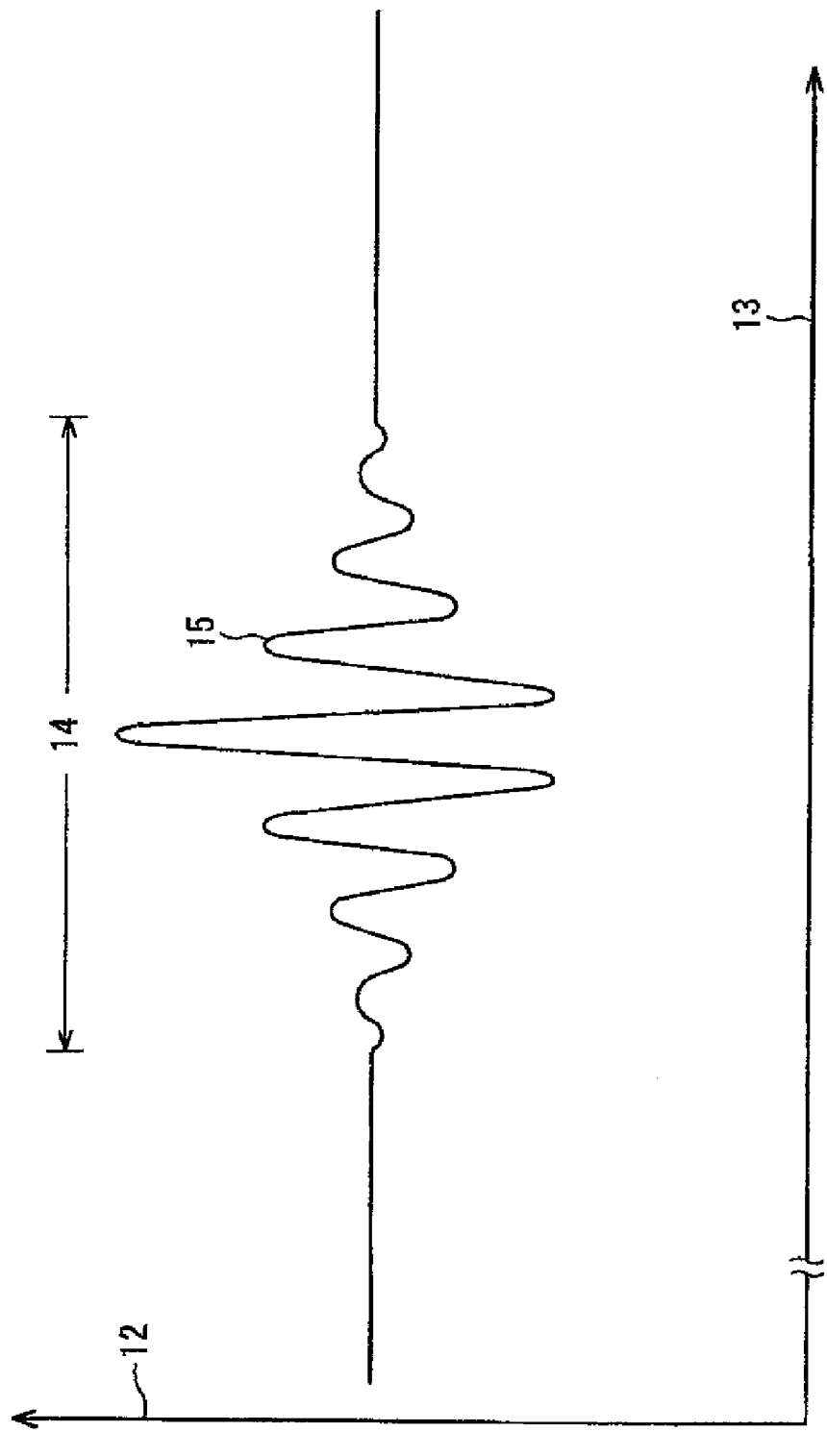
FIG. 9 shows an interference pattern (interferogram) obtained by the OCDR-OCT device.
Figure 10:
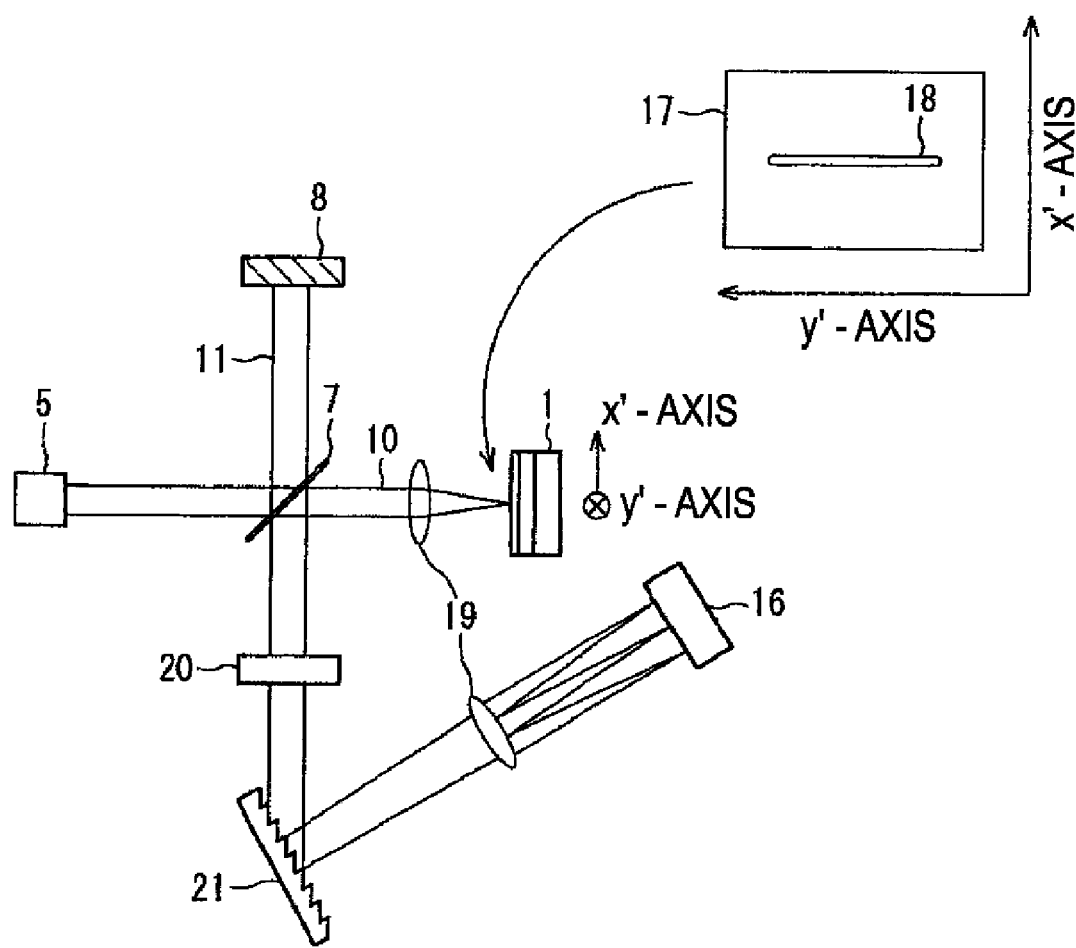
FIG. 10 shows the configuration of an FD-OCT device.
Figure 11:
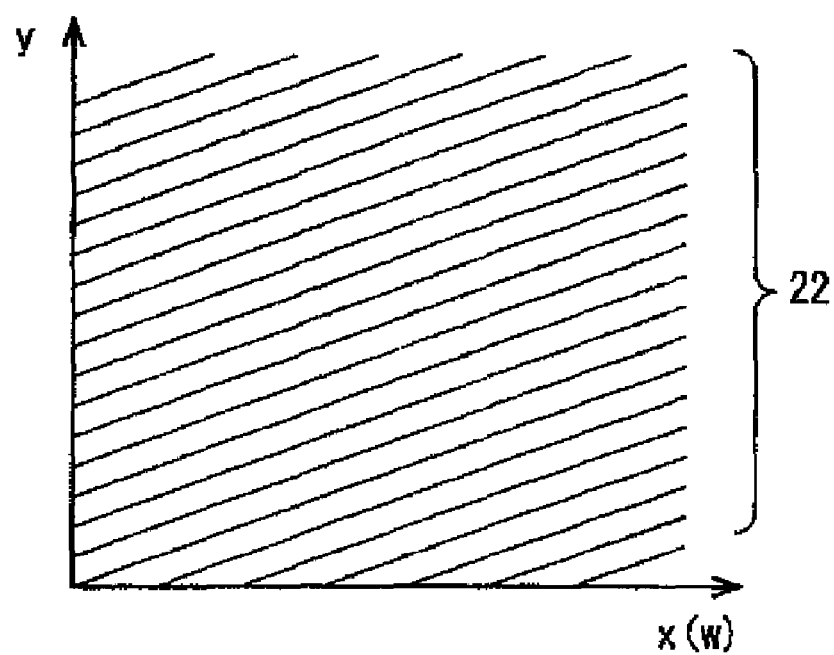
FIG. 11 shows a fringe (spatial interference pattern) that is obtained by the FD-OCT device.

Although a Mach-Zehnder-type interferometer was used as the interferometer in the above example, a Michelson interferometer may also be used as per the conventional technique in FIG. 8. That is, in the configuration of FIG. 8, the light source 5 may be substituted for the wavelength-tunable light generator 31 above. In this case, the movement of the reference mirror 8 is unnecessary. In the case of the configuration of FIG. 10, by using a cylindrical lens 19 that condenses the measurement light only in the direction of one axis and a CCD 16 as shown in FIG. 10, that is, by using the light source 5 in the configuration of FIG. 10 as a substitute for the wavelength-tunable light generator 31 above, a tomogram can be obtained by means of an A scan alone. In this case, the grating 21 is unnecessary.

Third Embodiment

The OCT of the third embodiment constitutes an optical system by means of a Michelson interferometer and a cylindrical lens in order to obtain a tomogram by means of an A scan alone. That is, as mentioned earlier, the configuration of FIG. 10 is a configuration in which the wavelength-tunable light generator is substituted for the light source 5. The grating 21 is unnecessary. Further, in the third embodiment, the wavelength-tunable range of the wavelength-tunable light generator is from 1511.74 to 1588.26 nm ($W_k=2.0\times10^{-1}$ µm) and the spectral frequency width is no more than 10 MHz. The scanning speed is 25 ns/step and the scanning of 80000 wave numbers is performed. Therefore, the wave number width per step is $2.5\times10^{-6}$ µm.

Because scanning of 80000 wave numbers is performed at a scanning speed of 25 ns/step, the measurement time (measurement time of an A scan) is 2.0 ms. When the static resolution $\Delta Z$ is found from Equation (2), $\Delta Z$ is 19 µm. Even when the biological sample moves at 9 mm/s, the distance moved by the sample in the measurement time is only 18 µm and is relatively small in comparison with the static resolution 19 µm, whereby degradation of the dynamic resolution does not occur.

Further, the measurable range is decided by the wave number interval and is 1300 mm as can be seen from Equation (4). Further, the measurable range computed from the frequency width is 13 m (See Equation (3)). Because the measurable range is sufficiently wide at 1300 mm or more, even when the measurement points are changed, the reference mirror position need not be adjusted.

Further, although only three examples of tunable wave number widths and wave number intervals and so forth of the wavelength-tunable light generator are mentioned, other possible combinations of tunable wave number widths and wave number intervals are not limited to the above illustrated examples. Combinations are listed in the table for means for solving the problem. The use of such combinations also affords effects similar to or greater than the above examples.

Furthermore, the OCT wavelength-tunable light generator may be a broadband light-emitting element such as an SLD or halogen lamp, a wavelength-tunable filter that extracts the output light of the broadband light-emitting element stepwise, and a control circuit thereof Examples of a wavelength-tunable filter that extracts the output light stepwise include a waveguide-type Fabry-Perot optical wavelength filter that appears in Patent Document 2, and an etalon, and so forth.

Fourth Embodiment

When a wavelength-tunable light generator based on this embodiment is employed, because the coherent length of the light provided by Equation (3) can be increased and the measurable range provided by Equation (4) is also increased, it is possible to implement a reflectometer device or tomography device by means of an optical system with an assembly of small parts without using a Michelson interferometer or Mach-Zehnder interferometer that is used in conventional OCT.

Figure 12:
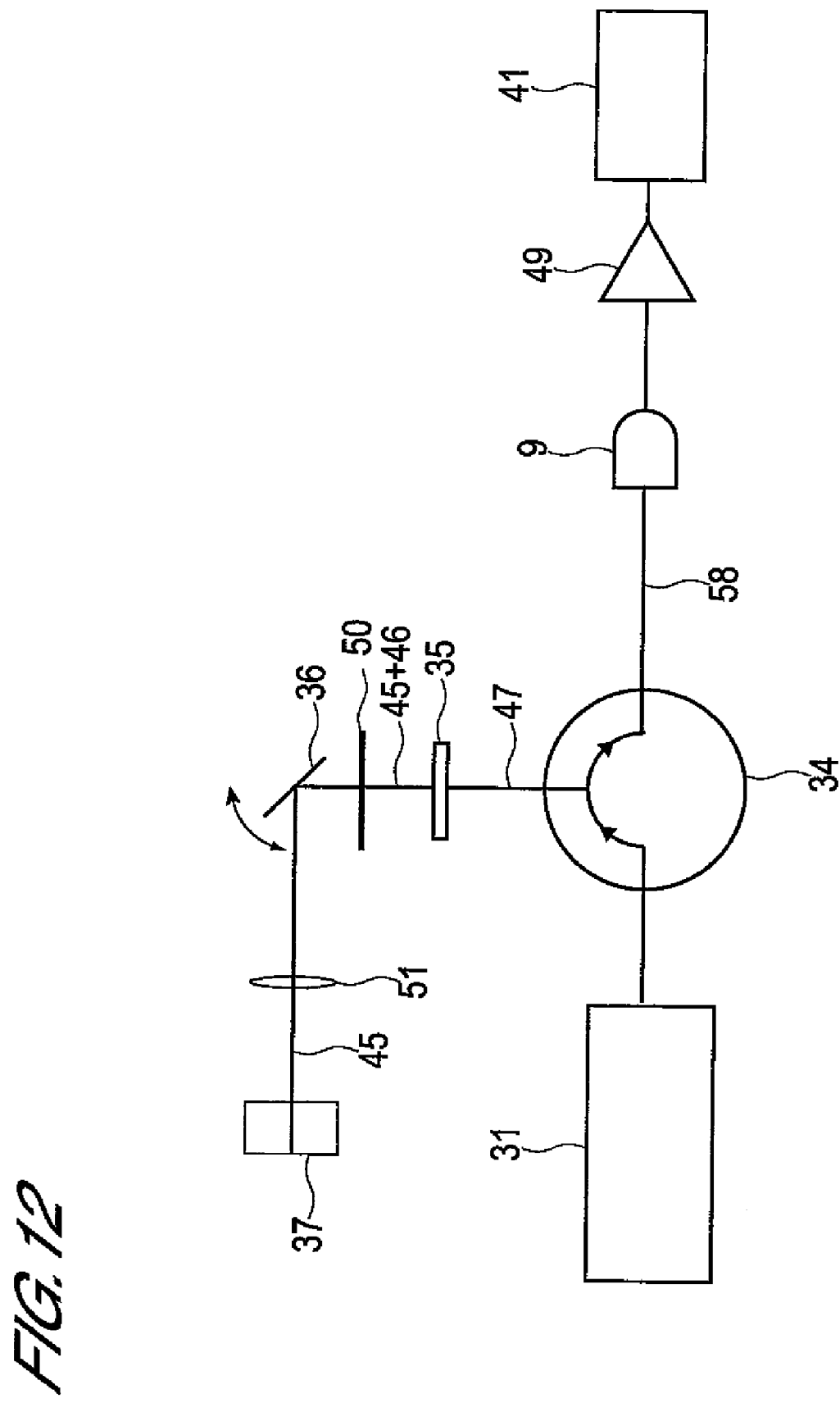
FIG. 12 shows the configuration of an FD-OCT device that does not divide the optical path of light.

The OCT device of this embodiment will now be described with reference to FIG. 12. In FIG. 12, the OCT device has a configuration in which the light of the wavelength-tunable light generator 31 is guided to the sample optical path by using the optical circulator 34 without being divided. In the sample optical path, the light passes through the optical fiber 47 from the optical circulator, leaves the end of the optical fiber, is collimated by the fiber source coupler 35, and is irradiated onto the sample 37 via the scanning mirror 36 and a focusing lens 51.

Light of intensity $I_S$ of the reflected light and backscattered light from the sample is collected after passing through the sample optical path and guided to a detection optical path 58 by the optical circulator 34. A reference light reflection element 50 is placed within the measurable range in which the distance from the measurement position of the deepest part of the sample is determined by the conditions of Equation (4). Part of the light with which the sample is irradiated is reflected along the sample optical path with intensity $I_r$, which is used as the reference light.

Such a configuration is made possible by using a wavelength-tunable light generator based on this embodiment which allows a long measurable range. The reflectance of the reflective mirror may be on the order of a few percent and, therefore, the reduction of the intensity of the light irradiated onto the sample and the light reflected and backscattered from the sample can be small.

In FIG. 12, the reference light reflection element 50 is disposed between the fiber source coupler 35 and the scanning mirror 36 but may be disposed anywhere on the sample optical path as long as the reference light reflection element 50 is in a position in the above measurable range.

When the reference light reflection element 50 is placed between the scanning mirror 36 and the sample 37, the reflective face may be bent to obtain a fixed reflection intensity in any direction in correspondence with changes in the direction of the irradiated light beam. Further, an extremely small total reflection prism may be placed in the widely collimated light beam instead of the partial reflection mirror. All partial reflection mechanisms that return part of the irradiated light in the sample optical path along the sample optical path are included in the technological scope of the present invention.

The partially reflected light and the reflected and backscattered light from the sample interfere and the intensity of the light that is detected by the photodetector 9 is given by Equation (26)

(Equation 30)

$$I_r + I_s + 2\sqrt{I_r I_s} \cos(2Lk_n) \quad (26)$$

Here, L is the distance between the partial reflection mirror and the position of the sample being measured. The output of the photodetector 9 is amplified by an amplifier 49 and then stored in the data processor 41 for each wave number $k_n$. The Equation (26) is the same function form as Equation (7) and the procedure to determine the reflectance as a function of depth from the interference term $2\sqrt{I_r I_s} \cos(2Lk_n)$ rendered by subtracting the dc terms $(I_r + I_s)$ is the same as the procedure described in detail in the first embodiment above.

Fifth Embodiment

Figure 13:
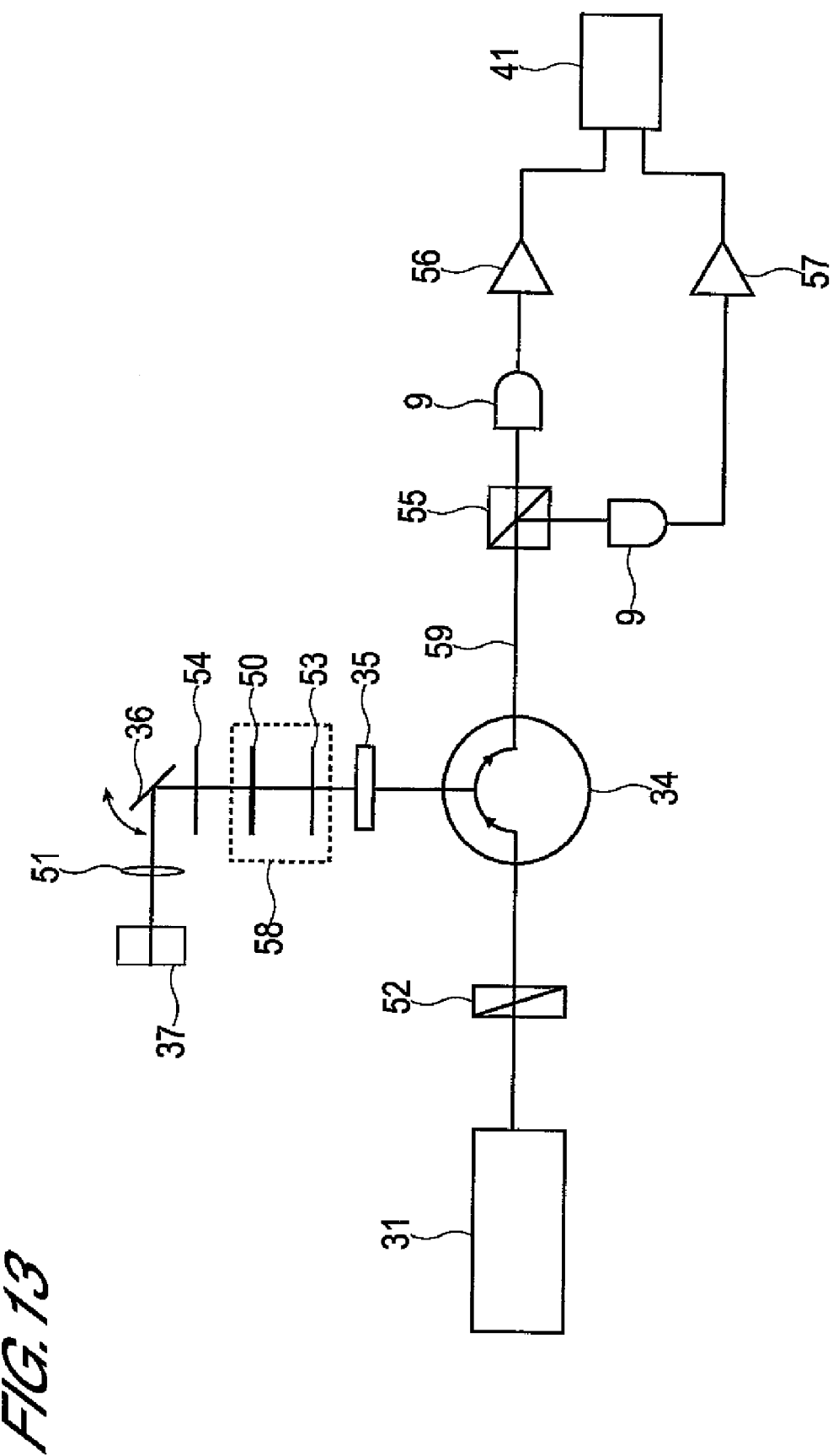
FIG. 13 shows the configuration of a FD-OCT device for performing polarization measurement, in which the optical path of light is not divided.

The OCT device of the fifth embodiment, which allows the configuration shown in FIG. 12 to measure a tomogram of the polarization characteristic of a sample, is described with reference to FIG. 13.

The polarization of the output light of the wavelength-tunable light generator 31 is usually linearly polarized, but in cases it is not linearly polarized, light is guided to the optical circulator 34 after linearly polarized by a polarization element 52. The optical circulator 34 guides the input light to the sample optical path and the light out of the optical fiber is turned into parallel light by the fiber source coupler 35.

A portion of the light that leaves the fiber source coupler 35 is reflected along the sample optical path with a portion of the light serving as reference light along the sample optical path after being afforded the desired polarization characteristic by the partial reflection mechanism 58 constituted by a wave plate 53 and the reference light reflection element 50.

As an example of a method for obtaining the desired polarization characteristic, a ¼ wave plate is used as the wavelength plate 53 and the direction of the axis of the wave plate may be inclined by 22.5 degrees (π/8 radians) with respect to the direction of the linear polarization of the input light. In this case, the light that is partially reflected is linearly polarized tilted through 45 degrees (π/4 radians) with respect to the polarization direction of the input light. This light is guided to an optical detection optical path 59 via an optical circulator 34 and, if the input polarization direction is tilted by 45 degrees with respect to the axis of a polarization beam splitter 55, the reference light intensity is equally divided into the two polarization directions of the polarization beam splitter 55.

A similar effect can be realized, without using the wavelength plate 53, by partially reflecting the input light that has been linearly polarized by means of the partial reflecting mirror and the polarization beam splitter 55 may be disposed so that the axis is tilted by 45 degrees with respect to the direction of linear polarization of the reflected light. Usage of the broad expression 'desired polarization characteristic' is due to the possibility of a variety of changes to obtain the same result by the combinations of polarization states of the input light, polarization-specific mechanisms of the sample, and the polarization beam splitter used for the detection.

Further, the conditions for the distance between the reference light reflection element 50 and the sample 37 are as described in the fourth embodiment above.

The irradiated light transmitted by the reference light reflection element 50 is irradiated onto the sample 37 after passing through a ¼ wavelength plate 54, which is a sample light polarization-specific mechanism for irradiating the sample after the irradiated light has been afforded the desired polarization characteristic. Although the desired polarization characteristic for the irradiated light is desirably that of circularly polarized light to make subsequent analysis is straightforward. However, if the polarization characteristic is specified, a tomogram of the polarization characteristic of the sample can be obtained for the sample irradiated in various polarization states of light, that includes elliptically polarized light and linearly polarized light, by the data processing of the data processor 41. Therefore, the irradiated light of desired polarization characteristic in the present invention includes all such cases.

The light that is reflected and backscattered from the sample 37 returns along the sample optical path, is guided to the detection optical path 59 by the optical circulator 34 together with the reference light, is divided into two components of mutually perpendicular polarizations by the polarization beam splitter 55, detected by the photodetector 9, amplified by an amplifier 56 and amplifier 57, and stored by the data processor 41 for each wave number $k_n$. Let the respective light intensities detected by the amplifiers be $I_\perp$ and $I_=$, the respective output intensities are given by the following Equations (27) and (28).

(Equation 31)

$$I_\perp = I_{r\perp} + I_{s\perp} + 2\sqrt{I_{r\perp} I_{s\perp}} \cos(2Lk_n) \quad (27)$$

$$I_= = I_{r=} + I_{s=} + 2\sqrt{I_{r=} I_{s=}} \cos(2Lk_n) \quad (28)$$

Here, $I_{r\perp}$ and $I_{r=}$ are the intensities of the reference light input to the two axial directions of the polarization beam splitter 55. However, if the axis of the linearly polarized reference light is input tilted by 45 degrees with respect to the axis of the polarization beam splitter, these reference-light intensities are equal. Even when the reference-light intensities are not equal, same can be corrected by the processing of the data processor 41.

If circularly polarized light is irradiated onto the sample of isotropic polarization characteristic, $I_{s\perp}$ and $I_{s=}$ of the scattered light of the two polarization directions are equal. If the sample has anisotropic polarization characteristic, $I_{s1}$ is different from $I_{s=}$, that is the scattered light of the two polarization directions, and the polarization characteristic of the sample can be determined from this difference.

Figure 19:
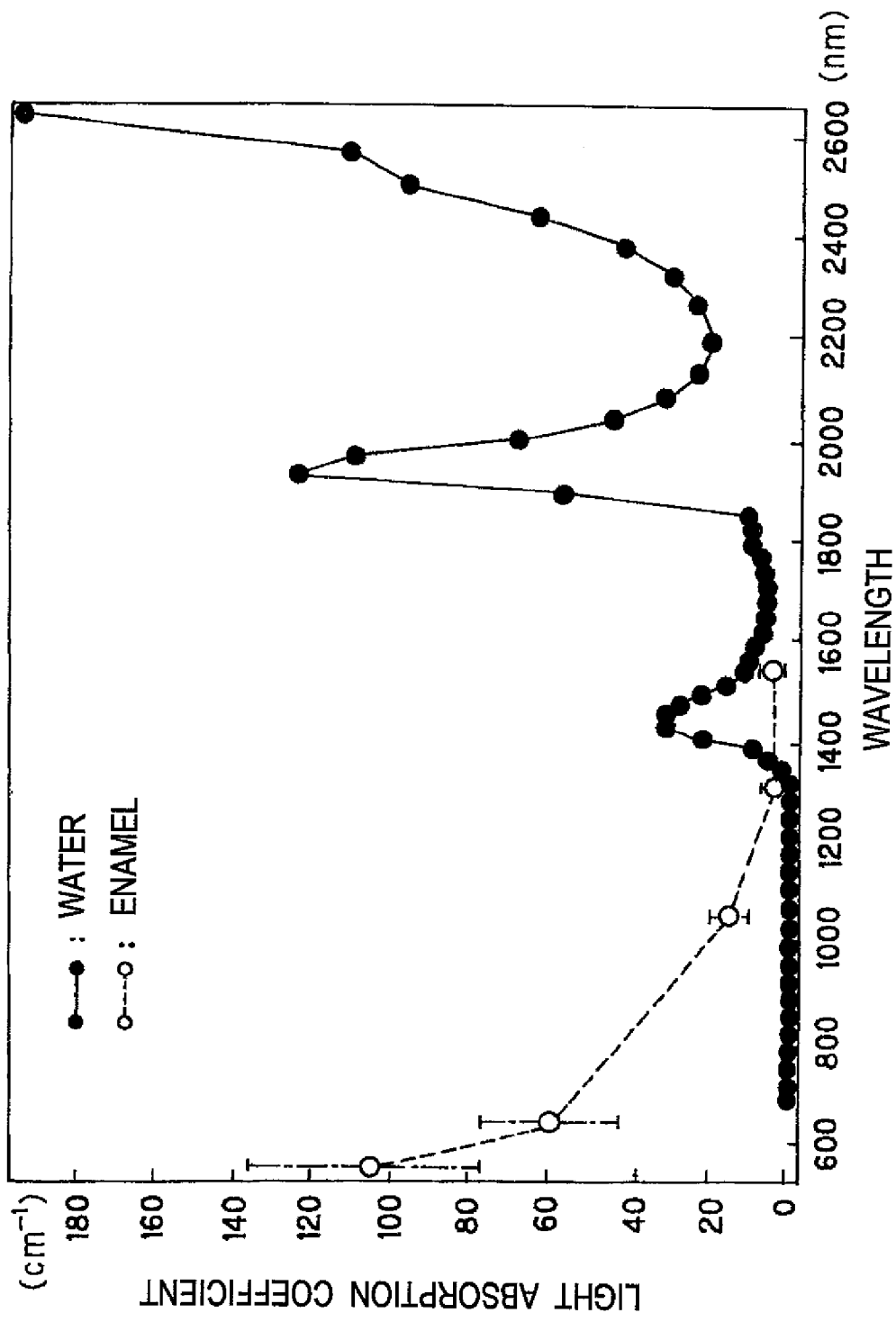
FIG. 19 shows the light absorption coefficient as a function of the center wavelengths of the measurement light for enamel and water.

\<B\> Wavelength-Tunable Light Generator for Dental OCT and Dental OCT Device Absorption coefficients of the light scattered by a tooth have been reported as 60 cm$^{-1}$ for a wavelength of 632 nm and 15 cm$^{-1}$ for a wavelength of 1053 nm for enamel, and 280 cm$^{-1}$ for a wavelength of 620 nm and 260 cm$^{-1}$ for a wavelength of 1053 nm for dentine (See page 593 of Non-Patent Document 5, for example). Longer wavelengths are advantageous in order to reduce the absorption coefficient of the scattered light. FIG. 19 shows the wavelength dependency of the light absorption coefficient of enamel and water. FIG. 19 shows the relationship between the center wavelength λ of the measurement light Lm and the light absorption coefficients for enamel 1101 and water. For enamel, because the light absorption coefficient decreases exponentially with an increase in the wavelength, longer wavelengths are advantageous. In order to enable OCT measurement via a layer 5 mm thick, the light absorption coefficient must be no more than 30 cm$^{-1}$ at −120 dB, which is the current sensitivity of OCT. On this basis, in order to be able to measure dentine by penetrating enamel 5 mm thick, the wavelength must be at least 0.9 μm as can be seen from FIG. 19.

FIG. 19 shows the absorption coefficient of light with 100% water. In reality, the compositional ratio of water in enamel is 1 to 2% and, for the purpose of a comparison with the effect of enamel absorption, the graph for the absorption of water in FIG. 19 must be compressed to 1/100 to 1/50 in the vertical axis direction. Thus, the effect of water absorption on the tissue of a tooth is small. However, there is a first absorption peak at approximately 1.45 μm and a strong absorption coefficient peak=at approximately 3 μm for water, and this absorption peak is useful=to detect the water contained in a cavity. However, the effects of thermal noise increase with an increase of the wavelength. Hence, wavelengths of no more than 5 μm are desirable.

OCDR, FD, and OFDR are known methods of OCT. Since OFDR is more sensitive than OCDR by 100 to 1000 times, OFDR is the best method from sensitivity when the intensity of light irradiated to the sample is restricted from the safety of the biological body.

OCDR and FD employ a broadband low-coherence light source. However, OFDR performs OCT measurements with a highly-coherent light source of narrow spectral width such as a laser and uses a wavelength-tunable light generator scanning the wavelength (See Non-Patent Document 4, for example). Hence, OFDR has the advantage that spectral OCT becomes possible by performing data analysis for separated wavelength ranges (See Patent Document 1, for example).

To a wavelength-tunable light generating means for OFDR, either of discrete or continuous change of wavelength may be used. However, for a light source which can change the wavelength discretely, no change of the wavelength occurs during one data acquisition, resulting in accurate determination of the wavelength dependence of the characteristics.

In a wavelength-tunable light generating means that perform discrete wavelength change, in order that the resolution for obtaining a tomogram of a tooth is at least 80 μm or more, the width of the tunable range of the wave numbers (2π/wavelength) must be at least $4.7 \times 10^{-2}$ μm$^{-1}$, and, in order that the measurable range based on the interference of light be at least 10 mm, the frequency width of the emitted light must be no more than 13 GHz. Further, in order that the distance at which overlapping of OCT images does not occur is at least 10 mm (at least 5 mm on one side), the wave number interval must be no more than $3.1 \times 10^{-4}$ μm$^{-1}$ and, in order to minimize the effect of movement of a human body such as the heart beat, measurement must be executed at high speed. Hence, the wave number interval time is desirably no more than 530 μs.

Here, when the wavelength is scanned discretely, as shown in FIG. 25(*a*), the wavelength may be increased gradually and, as shown in FIG. 25(*b*), the wavelength may be decreased gradually. As shown in FIG. 25(*c*), the wavelength may be changed irregularly. In short, predetermined wavelengths may all be scanned within the measurement time. Further, although, when regarded in terms of wave numbers, the 'predetermined wavelength' is preferably a set of wave numbers that stand in a row at equal intervals, the 'predetermined wavelength' is not limited thereto. By considering the computation processing when the tomographic image is created, for example, application is also possible in the case of a set of wavelengths in which the wave number interval is not fixed.

Further, as the wavelength range for the light to be measured, 1.2 to 5.0 μm is preferable because light-emitting means and light-detection means can be easily obtained. In particular, 1.3 to 1.6 μm (preferably 1.35 to 1.6 μm, more preferably 1.4 to 1.6 μm, and most preferably 1.5 to 1.6 μm) is highly preferable because optical communication light-emitting means and light-detection means can be used. In other words, the wavelength-tunable range of the wavelength-tunable light generating means is preferably wider than 1.3 to 1.6 μm within 1.2 and 5.0 μm and highly preferably wider than 1.35 to 1.6 μm within 1.3 and 1.6 μm in particular (preferably wider than 1.4 to 1.6 μm within 1.35 and 1.6 μm, more preferably wider than 1.5 to 1.6 μm within 1.4 and 1.6 μm, and most preferably within 1.5 and 1.6 μm).

A principal examination object of a tooth examination device is normally the structure of a tooth or, in particular, whether there aren't any cavities and, when a dental treatment has been performed, whether the state of a treatment such as a filling is normal or whether the state of the gums (such as gum disease) is normal. When used in a dental assessment, an OCT tomogram of various parts in the oral cavity is also useful. The present invention diagnose mainly teeth but can also be used in such cases.

The structure of a tooth is as follows: the outermost part is the enamel inside which is dentine, and the innermost part is the dental pulp. It is known that the enamel has a strongly birefringent structure and, even when the circularly polarized light is input, scattered light is polarized. Therefore, by measuring the polarization characteristic of the scattered light, the boundary between the enamel and dentine can be clearly distinguished. Further, because a filling accompanying a dental treatment has weak birefringence, the boundary with the enamel can be clearly discriminated by measurement of the polarization. As the refractive index depends on the wavelength, the birefingence also exhibits wavelength dependency and, therefore, OFDR-OCT that allows spectroscopic analysis by dividing the wavelength range is the most suitable.

Figure 23:
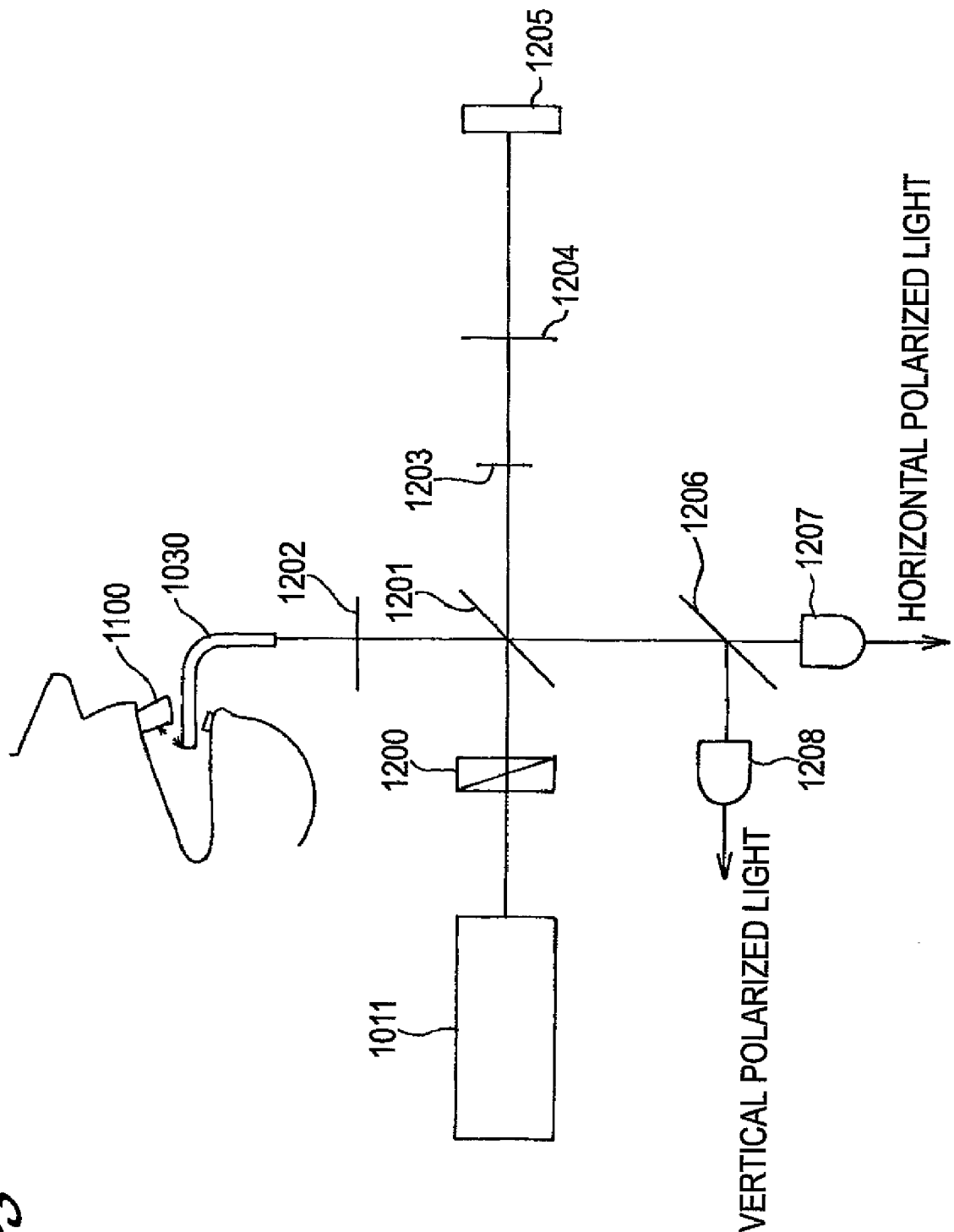
FIG. 23 is a drawing of an embodiment (an example of when the polarization characteristic of the tooth is measured) of the dental OCT device of the present invention.

Here, an embodiment (an example of a case where the polarization characteristic of a tooth is measured) of the dental OCT wavelength-tunable light generator and dental OCT device according to the present invention will be described based on FIG. 23. FIG. 23 is a schematic drawing of the dental OCT device.

As shown in FIG. 23, light is emitted from a wavelength-tunable light generator 1011 constituting the wavelength-tunable light generating means, the linear polarization direction of the light is determined by a polarizer 1200 and the light is divided into a sample optical path and reference optical path by a beam splitter 1201 constituting the main dividing means.

The sample optical path (measurement light) is circularly polarized by a wave plate 1202 and passes through a probe 1030 constituting flexible tubular measurement light irradiating means before being irradiated onto a tooth 1100. The reflected light from inside the tooth (signal light) is collected by the probe 1030 constituting signal light collecting means and returned to the beam splitter 1201 via the wave plate 1202. The beam splitter 1201 also acts as combining means. The scattered light is polarized depending on the birefrigence of the sample.

The light (reference light), that is divided by the beam splitter 1201 and enters the reference optical path (reference light) passes through an attenuation element 1203 and a wave plate 1204, is reflected by a reference mirror 1205 and returned to the reference optical path before entering the beam splitter 1201 and being combined with the signal light. The rate of attenuation of the attenuation element 1203 is set for an optimum signal-to-noise ratio. The wavelength plate 1204 is set so that the light returning to the beam splitter 1201 is circularly polarized.

A polarization beam splitter 1206 constituting polarized light separating means separates the light from the beam splitter 1201 into a horizontally polarized light and a vertically polarized light. The horizontally polarized light is detected by a photodetector 1207 and the vertical polarized light is detected by a photodetector 1208, whereupon each of the light components is amplified, A/D-converted, and input to a computer (not shown) constituting computation control means. Based on the mutual phase and intensity relationship between the horizontal polarized light and vertical polarized light thus detected, the polarization characteristic is computed by the computer as a function of the depth in the tooth.

That is, the dental OCT device according to this embodiment comprises polarization characteristic measuring means for measuring the polarization characteristic of a tooth, wherein the polarization characteristic measuring means comprise main dividing means (beam splitter 1201) that divide the light emitted by the wavelength-tunable light generating means (wavelength-tunable light generator 1011) into measurement light and reference light by controlling the polarization direction of the light, measurement light irradiating means (probe 1030) for irradiating the measurement light divided by the main dividing means (beam splitter 1201) onto the tooth 1100 in the oral cavity, signal light collecting means (probe 1030) for collecting the signal light that is irradiated onto the tooth 1100 and reflected thereby, combining means (beam splitter 1201) for combining the signal light collected by the signal light collecting means (probe 1030) and the reference light that is divided by the main dividing means (beam splitter 1201), polarization separation means (polarization beam splitter 1206) for separating the light combined by the combining means (beam splitter 1201) into components of two or more polarization directions, and computation control means (computer) for determining birefringence of the tooth 1100 on the basis of the intensity of the light of different polarization directions separated by the polarization beam splitter 1206.

Figure 14:
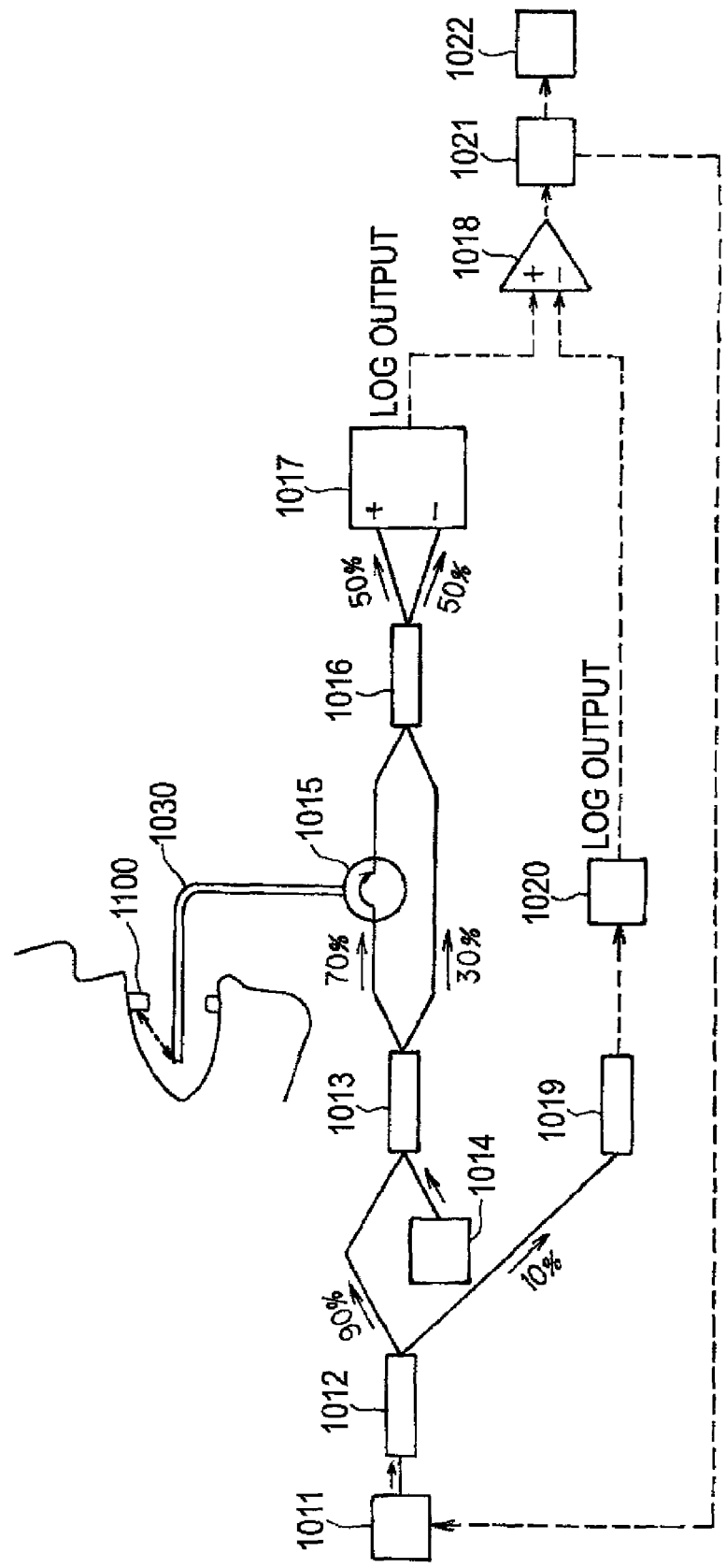
FIG. 14 is a schematic drawing of an embodiment of the dental OCT device of the present invention (an example of the case where a cavity is detected by means of the reflection intensity)
Figure 15:
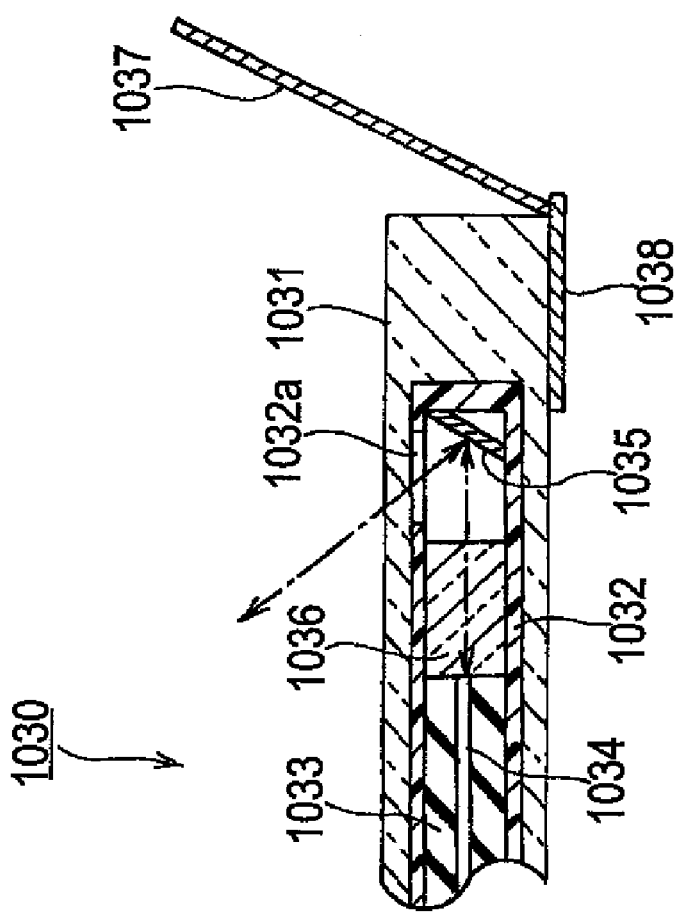
FIG. 15 is a schematic view of the probe in FIG. 14.

Furthermore, the dental OCT device of the present invention and an embodiment of the dental OCT device (an example in which a cavity is detected by means of the reflection intensity) will now be described on the basis of FIGS. 14 and 15. FIG. 14 is a schematic drawing of a cavity-detecting device constituted by the dental OCT device and FIG. 15 is a schematic drawing of the probe in FIG. 14.

As shown in FIG. 14, the output port one side of the wavelength-tunable light generator 1011 constituting the wavelength-tunable light generating means for emitting light while changing the wavelength such as a super structure grating distributed Bragg reflector semiconductor laser (See Non-Patent Document 4, for example), for example, is optically connected to the input port of the first coupler 1012 that comprises a directional coupler or the like that divides light into two (90:10, for example).

The output port one side (the 90% division percentage side) of the first coupler 1012 is optically connected to the input port of a second coupler 1013 that constitutes the main dividing (70:30, for example) means that comprise a directional coupler or the like. The output port of an aiming light source 1014, which is a visible light source that emits light in a visible region to observe the irradiation position of measurement light, is optically connected to input port of the second coupler 1013.

The output port on one side (the 70% division percentage side) of the second coupler 1013 is connected to the input port of an optical circulator 1015. The output port on the other side=(the 30% division percentage side) of the second coupler 1013 is optically connected to the input port of a third coupler 1016 constituting combining means comprising a directional coupler and so forth that divides light into two (50:50, for example). The optical circulator 1015 is optically connected to the input port of the third coupler 1016 and the base end of the flexible tubular probe 1030 is connected to the optical circulator 1015. The probe 1030 has the structure shown in FIG. 15.

As shown in FIG. 15, at least the leading end of a flexible outer tube 1031 comprising resin or the like is optically transparent and closed. A flexible inner tube 1032 comprising resin or the like with a closed tip is inserted into the outer tube 1031 and supported so that the inner tube 1032 is able to slidably rotate in a circumferential direction with respect to the outer tube 1031. A flexible filling material 1033 comprising resin or the like is made to fill the inside of the inner tube 1032 and an optical fiber 1034 is laid and supported coaxially. The base end of the optical fiber 1034 is optically connected to the optical circulator 1015.

An I/O light window 1032a is formed in a portion of the peripheral wall of the leading end of the inner tube 1032. A reflective mirror 1035 is laid at the leading end on the inside of the inner tube 1032. An optical member 1036 such as a condensing imaging lens is laid between the end of the optical fiber 1034 inside the inner tube 1032 and the reflective mirror 1035. An observation mirror 1037 used for visual confirmation is laid outside the leading end of the outer tube 1031. The observation mirror 1037 is fixed and supported by a bracket 1038 that is attached to the outer circumferential face of the leading end of the outer tube 1031. Further, a support tool (not shown) that allows flexible support and movement within the oral cavity is attached to the leading end of the outer circumferential face of the outer tube 1031.

That is, the measurement light that enters from the base side of the optical fiber 1034 passes through and exits the outer tube 1031 via the I/O light window 1032a of the inner tube 1032 via the reflective mirror 1035 after being collimated into a narrow parallel beam by the optical member 1036 and the signal light that is reflected (backscattered) after being irradiated onto the tooth 1100 enters the inside of the inner tube 1032 via the I/O light window 1032a of the inner tube 1032 after passing through the outer tube 1031, enters the inside from the leading end of the optical fiber 1034 via the reflective mirror 1035 and optical member 1036 before entering the optical circulator 1015. 1039 in FIG. 15 is a rotating bearing.

In this embodiment, linking means are constituted by a reflective mirror 1035 and an optical member 1036 and so forth and the irradiating and collecting means, which serve as both measurement light irradiating means and signal light collecting means, are constituted by the probe 1030 and optical circulator 1015 and so forth.

As shown in FIG. 14, the output port on both sides of the third coupler 1016 are optically connected to the light inputs ports of a first differential amplifier 1017 having optical detection function. The Log output of the first differential amplifier 1017 is electrically connected to the Log input of a second differential amplifier 1018 that perform computation to correct the fluctuations in the input signal intensity.

On the other hand, the other output port (the 10% division percentage side) of the first coupler 1012 is optically connected to the input port of a photodetector 1019. The output of the photodetector 1019 is electrically connected to the input of a Log amplifier 1020. The Log output of the Log amplifier 1020 is electrically connected to the Log input of the second differential amplifier 1018.

The output of the second differential amplifier 1018 is electrically connected via an analog/digital converter (not shown) to the input of a computation control device 1021 that combines interferogram, that is, a backscatter intensity distribution (See Non-Patent Document 4, for example). The output of the computation control device 1021 is electrically connected to the input of a display device 1022 such as a monitor or printer that displays the computation result. The computation control device 1021 is capable of controlling the wavelength-tunable light generator 1011 according to the input information. The computation control means are constituted in this embodiment by the first differential amplifier 1017, the second differential amplifier 1018, the photodetector 1019, the Log amplifier 1020, the computation control device 1021, and the display device 1022 and so forth.

A tooth scanning method (cavity detecting method) that uses a cavity detecting device constituting the dental OCT device according to this embodiment will be described next.

By inserting the leading end of the probe 1030 into a person's oral cavity, using a movement support tool to align and support the probe 1030 at a predetermined point of the oral cavity, and operating the computation control device 1021, the measurement light of the intended wavelength range is emitted by the wavelength-tunable light generator 1011 (wavelength-tunable range: 1500 to 1550 nm, spectral width: no more than 10 MHz, scanning wave number (A scan number):400) and visible light is emitted from the aiming light source 1014.

The light that is emitted by the wavelength-tunable light generator 1011 is divided into two by the first coupler 1012 (90:10). The light on one side (90% side) that has been divided into two by the first coupler 1012 is divided into two (70:30) by the second coupler 1013. Further, the light (corrected light) on the other side (10% side) that has been divided into two by the first coupler 1012 is sent to the photodetector 1019.

The light (measurement light) on one side (70% side) that has been divided into two by the second coupler 1013 passes inside the optical fiber 1034 of the probe 1030 via the optical circulator 1015 together with the visible light and is irradiated onto the tooth 1100 as a result of being emitted from the leading end of the probe 1030 as described earlier.

Thereupon, the probe 1030 is flexible, the inner tube 1032 can be slided and rotated in a circumferential direction with respect to the outer tube 1031, and visible light is emitted together with the measurement light. Hence, the measurement light can be easily irradiated onto the tooth 1100 in the intended position of the oral cavity.

The light (signal light) that is irradiated onto the tooth 1100 and reflected (backscattered) re-enters the probe 1030 as described earlier and is sent to the third coupler 1016 via the optical circulator 1015. Further, the light (reference light) of the other side (30% side) that has been divided into two by the second coupler 1013 is sent to the third coupler 1016 and combined with the signal light.

The light that is combined by the third coupler 1016 is sent to the first differential amplifier 1017. The first differential amplifier 1017 outputs a Log output signal to the second differential amplifier 1018. Further, the photodetector 1019 converts the light (corrected light) of the other side (10% side) that has been divided into two by the first coupler 1012 into an electrical signal and outputs the electrical signal to the Log amplifier 1020. The Log amplifier 1020 outputs a Log output signal to the second differential amplifier 1018. The second differential amplifier 1018 outputs the information signal to an analog/digital converter after performing input-intensity correction processing.

The analog/digital converter converts the input information signal into a digital signal and outputs the digital signal to the computation control device 1021. The computation control device 1021 performs computation processing on the basis of the variety of information thus input, determines the interferogram, that is, the intensity of the signal light, finds the characteristic of the tooth 1100 on the basis of the intensity and so forth (described in detail subsequently) and displays the result on the display device 1022.

The characteristics of teeth that enable early stage cavities and so forth to be detected can be found from characteristic data on the tooth 1100 that are found in this manner.

Here, an example of tooth measurement results for which the dental OCT device described earlier was employed is shown in FIG. 24. In this measurement, the first differential amplifier 1017 is connected directly to the computation control device 1021 without using the photodetector 1019, Log amplifier 1020, and second differential amplifier 1018 in FIG. 14 so that the proportional output of the differential amplifier 1017 is input directly. A super structure grating distributed Bragg reflector semiconductor laser light generator having a wavelength range of 1530 to 1570 nm, a wavelength interval of 0.1 nm, and a wavelength scanning speed of 0.1 nm/10 μs was used as the wavelength-tunable light generator 1011.

An extracted canine tooth was used as the sample. A photograph of the canine tooth is shown in FIG. 24(P). In FIG. 24, (A) to (E) are OCT images of the respective cross-sections along the lines (a) to (e) shown in the photograph (P). As shown in (A), the degree of penetration is an optical distance on the order of 4 mm. Towards the tip part, the dentine inside the surface enamel can be observed. At (B), the enamel is thick and the dentine cannot be seen clearly. In moving to the tip at (C), (D), and (E), the dentine inside the enamel can be seen more clearly. Further, at (D) and (E), the signal for the dentine inside is observed more strongly than the signal for the surface enamel. This corresponds to the fact that the dentine has a stronger scatter capacity than enamel.

In about the middle of (C) and (D), cracks that penetrate the dentine are observed midway along the enamel. These cracks are not observed at the surface. Thus, internal lesions that are not that do not appear at the surface can be observed by OCT.

Here, this principle will be described in more detail.

Figure 16:
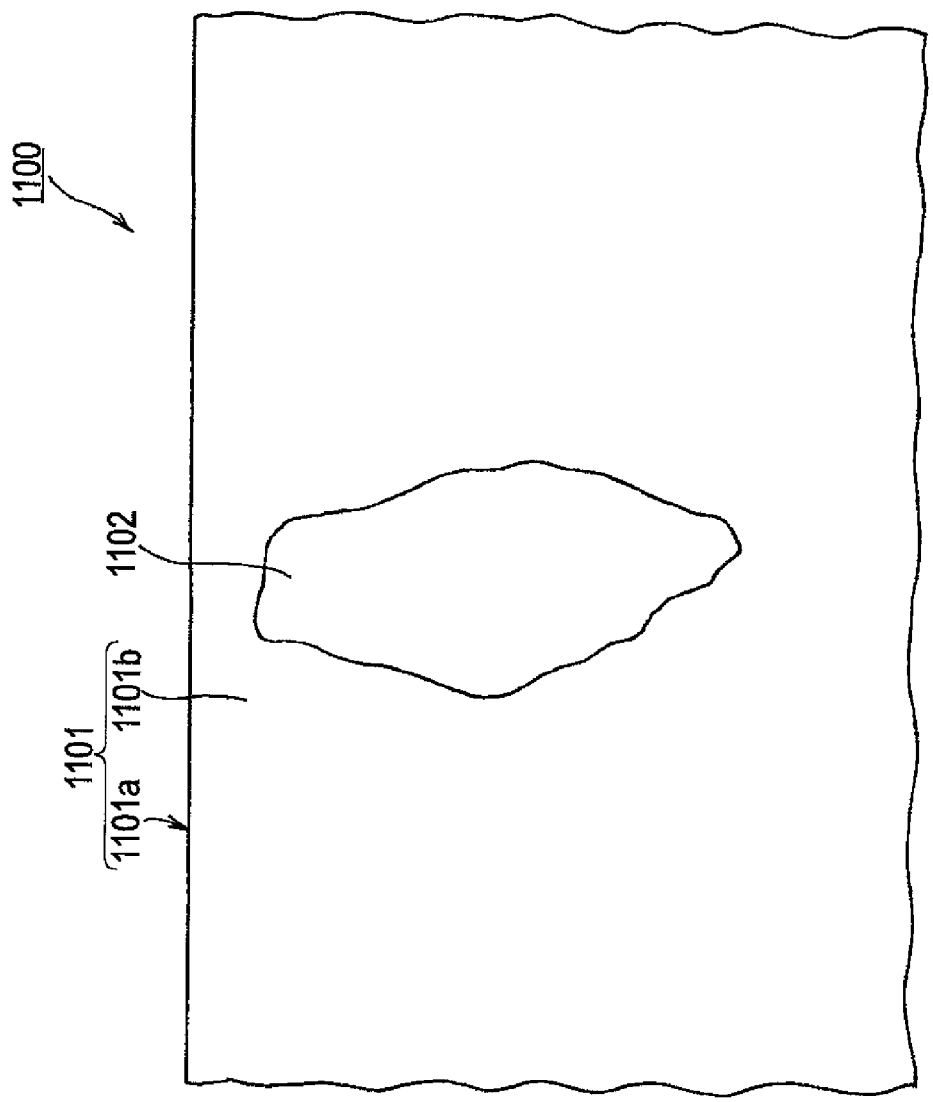
FIG. 16 is an explanatory drawing of an early stage cavity.

The enamel forming the outermost portion of the tooth 1100 is the hardest part within the human body and is a composition in which the weight ratios in percentages are 96% inorganic content, 2% organic content, and 2% water content. The inorganic part ultimately results in a cavity as result of the repeated intrusion (decalcification) of acid produced by tooth bacteria. As shown in FIG. 16, early stage cavities are formed as small pits 1102 in the interior portion 1101*b* of the enamel 1101 and are not generated in the surface 1101*a* of the enamel 1101 of the tooth 1100.

In the enamel 1101 of a healthy tooth 1100, the water concentration is extremely small as mentioned earlier. However, in the enamel 1101 of a tooth 1100 with an early stage cavity of the pits 1102 mentioned above, water concentration is high because of the invasion of saliva in the oral cavity into the pits 1102.

Therefore, in the present embodiment, by determining the abundance ratio per unit volume of water and the composition of the enamel 1101 of the tooth 1100, the characteristics of the tooth 1100 with an early stage cavity or the like can be easily detected.

Further, among OCT methods, an FD-OCT device to which FD method is applied using a wavelength-tunable light as the light source is also able to measure wavelength dependence of the light absorption coefficient of the biological body while imaging a tomogram of it, and usage thereof in the measurement of the oxygen saturation of the biological body, for example, has been proposed (See Patent Document 4, for example).

With such a conventional FD-OCT device, because water, that exists in most human tissues including bone in concentration as high as several ten percents, absorbs infrared light strongly, the use of near-infrared light is avoided in measurement. Light in the wavelength range of 650 to 1100 nm, named as the window of the biological body, is used.

On the other hand, the present embodiment focuses on the characteristics of the enamel 1101 of the tooth 1100 that barely contains water, that is largely different from other human tissues. And, by using the wavelength range not shorter than 1.2 μm, that is not used by conventional FD-OCT devices and in which absorption by the composition of enamel 1101 is negligible while absorption by water is strong, the present embodiment made possible to determine the characteristics (existence of pits 1102 and the positions thereof) of the tooth 1100 by determining the abundance ratio per unit volume of water and the composition of the enamel 1101 of the tooth 1100.

The method of calculating a signal light intensity distribution and light absorption coefficient distribution for the enamel 1101 of the tooth 1100, and a abundance distribution of the composition and water per unit volume will be described more specifically hereinafter.

Figure 17:
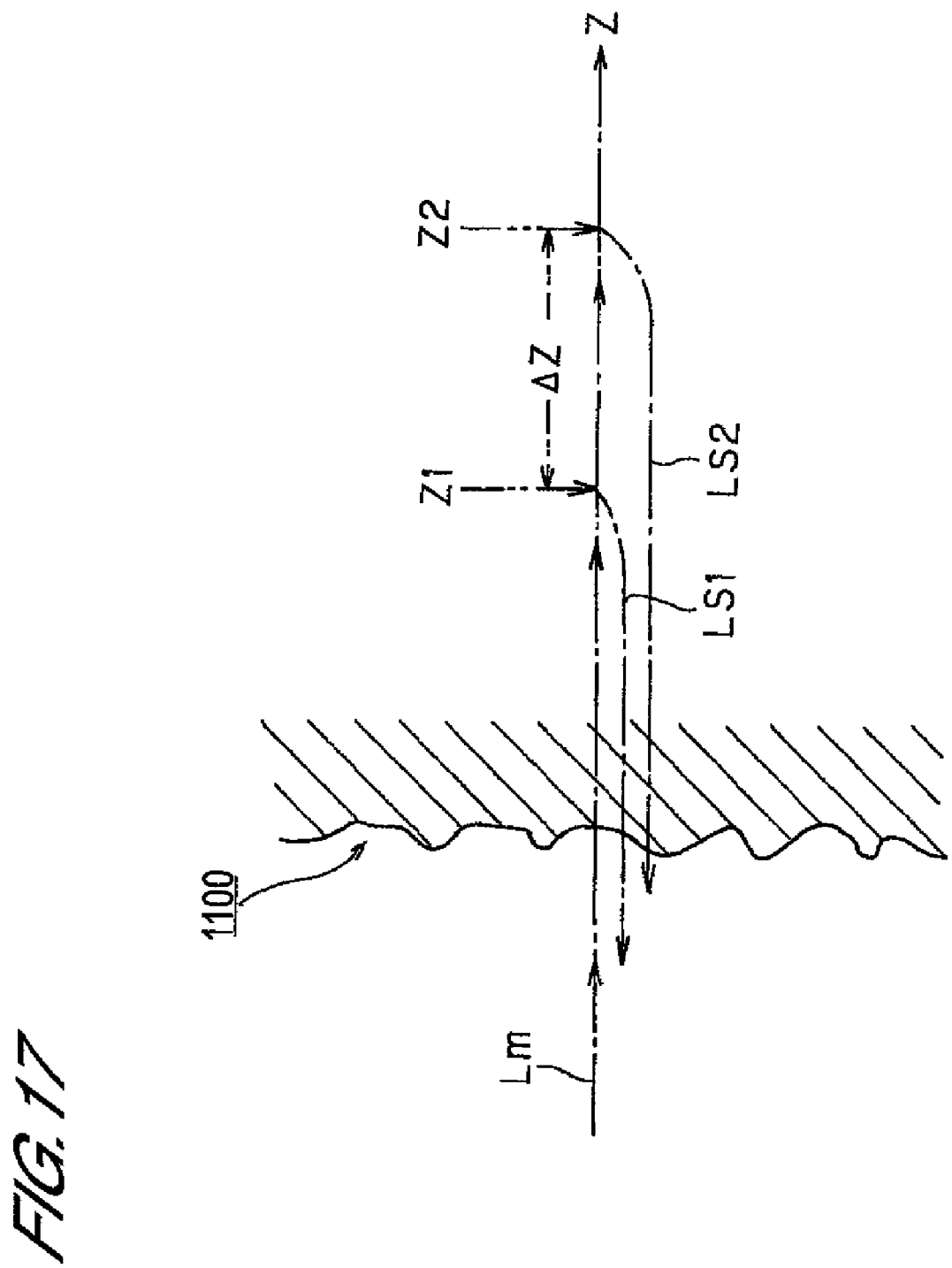
FIG. 17 is an explanatory drawing of the principle of measuring the light absorption coefficient in a minute region.

FIG. 17 is an explanatory diagram of the principle of measuring the light absorption coefficient of a small region. In FIG. 17, the measurement light Lm, in a wavelength range centered at wavelength λ, enters along the Z axis which is chosen along the thickness direction (depth direction) of the tooth 1100. In OCT, the signal light Ls that is reflected (backscattered) along the optical axis of the input measurement light Lm can be measured at a resolution of several tens of μm in the Z-axis direction.

As shown in FIG. 17, z1 is a certain position along the optical axis (Z axis) of the incident measurement light Lm and z2 is a different position that is separated by a short distance Δz (on the order of several tens of μm, for example). Further, it is assumed that, at positions z1 and z2, the light scattering coefficient is equal and light attenuation is all due to the absorption.

When the light absorption coefficient of the small region between z1 and z2 is expressed by μ(z1, λ) as a function of position z1 and the center wavelength λ of the measurement light Lm, the ratio of the intensity I(z1) (OCT signal intensity) of the signal light Ls1 reflected (backscattered) at position z1 to the intensity I (z2) of the signal light Ls2 reflected (backscattered) at position z2 can be expressed by Equation (29) according to the Beer-Lambert law for light absorption.

$$I(z1)/I(z2)=\exp[2\cdot\mu(z1,\lambda)\cdot\Delta z] \qquad (29)$$

Here, the coefficient 2 in Equation (29) is due to consideration for both the incident measurement light Lm and the reflected (backscattered) signal light Ls1 and Ls2. Based on Equation (29), the light absorption coefficient μ(z1, λ) between the positions z1 and z2 on the measurement light Lm at the center wavelength λ is determined.

When the distribution of abundance percentages per unit volume of the composition and water in the enamel 1101 of the tooth 1100 is determined, it is extremely preferable to measure the distribution of the light absorption coefficients for a plurality of different wavelength ranges. The greater the variety of center wavelengths λ of the measurement light Lm, the larger the number of parameters that can be determined, whereby the accuracy can be improved. However, in this embodiment, the measurement light Lm1 and Lm2 in two wavelength regions at two different center wavelengths λ1 and λ2, respectively, are used for convenience to explain.

Figure 18:
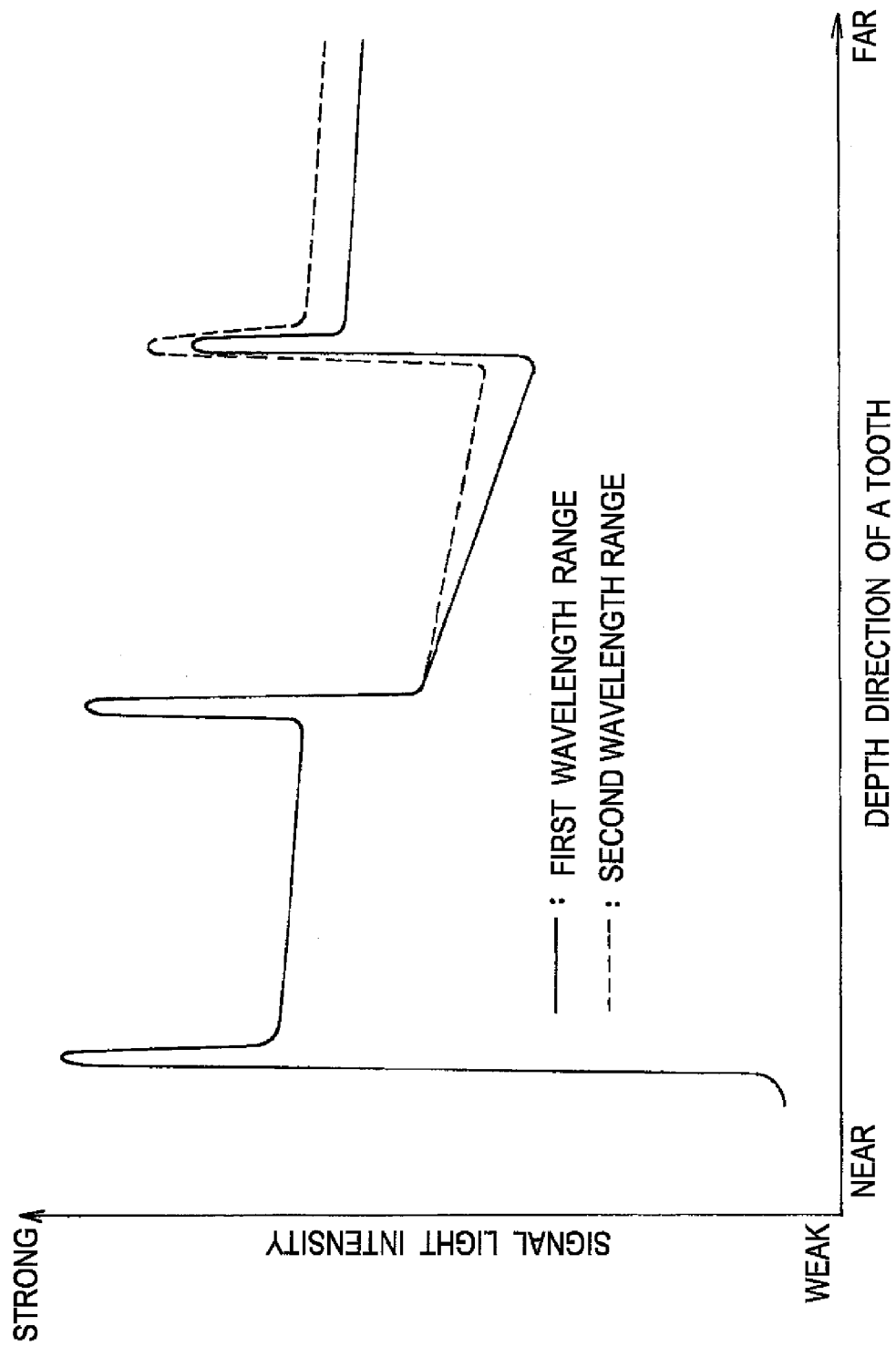
FIG. 18 shows the optical signal intensity as a function of the position in the thickness direction (depth direction) of a tooth.

More specifically, the wavelength-tunable range (1500 to 1550 nm) of measurement light Lm that can be output from the wavelength-tunable light generator 1011 is divided into two ranges which are the first wavelength range (1500 to 1525 nm) and the second wavelength range (1525 to 1550 nm). And, as shown in FIG. 18, the intensity (solid line) of the signal light Ls1 corresponding to the measurement light Lm1 of the first wavelength range and the intensity (dotted line) of the signal light Ls2 corresponding to the measurement light Lm2 of the second wavelength range are determined in the thickness direction (depth direction) of the tooth 1100.

Further, the distributions of the light absorption coefficients for each wavelength range are found from the distribution of the intensities of the signal light Ls1 and Ls2, and the distributions of the abundance ratio per unit volume of the composition and water in the enamel 1101 of the tooth 1100 are found from the distribution of the light absorption coefficient.

That is, a conventional FD-OCT device emits measurement light Lm over the whole of the wavelength-tunable range that can be output from the wavelength-tunable light generator 1011 and the light absorption coefficient is found from the intensity of the reflected light (backscattered light) of the measurement light Lm. However, in this embodiment, a plurality of measurement light Lm1, Lm2, . . . in the wavelength ranges of the mutually different center wavelengths λ1, λ2, within the wavelength-tunable range that can be output from the wavelength-tunable light generator 1011 are emitted, and the light absorption coefficients are determined from the intensities of the signal lights for the respective reflected light (backscattered light) corresponding the respective measurement light Lm1 and Lm2 . . . .

As can be seen from FIG. 19, the wavelength dependence of the light absorption coefficients of enamel 1101 and water differ largely.

For example, supposing that the center wavelength λ1 of the first measurement light Lm1 is 1512.5 nm and the center wavelength λ2 of the second measurement light Lm2 is 1537.5 nm, although the light absorption coefficient of the enamel 1101 represents substantially the same value (3.8 cm$^{-1}$) for the first and second measurement light Lm1 and Lm2, the light absorption coefficient of water represents a larger value for the first measurement light Lm1 (center wavelength λ1) than the second measurement light Lm2 (center wavelength λ2).

Here, suppose that the abundance ratio (density) of the composition of the enamel 1101 at position z1 is $C_E(z1)$ and the abundance ratio (density) of the water at position Z1 is $C_{H2O}(z1)$, these values can be found from the following equations (30) and (31).

$$\mu_{H2O}(\lambda1) \cdot C_{H2O}(z1) + \mu_E(\lambda1) \cdot C_E(z1) = \mu(z1, \lambda1) \quad (30)$$

$$\mu_{H2O}(\lambda2) \cdot C_{H2O}(z1) + \mu_E(\lambda2) \cdot C_E(z1) = \mu(z1, \lambda2) \quad (31)$$

Here, $\mu_{H2O}(\lambda1)$ is the light absorption coefficient of water of the first measurement light Lm1 at center wavelength λ1, $\mu_{H2O}(\lambda2)$ is the light absorption coefficient of water for the second measurement light Lm2 at center wavelength λ2, $\mu_E(\lambda2)$ is the light absorption coefficient of the enamel composition for the first measurement light Lm1 at center wavelength λ1, $\mu_E(\lambda2)$ is the light absorption coefficient of the enamel composition for the second measurement light Lm2 at the center wavelength λ2 and these values can be found from FIG. 19.

Furthermore, $\mu(z1, \lambda1)$ is the light absorption coefficient of the first measurement light Lm1 at center wavelength λ1 at position z1, $\mu(z1, \lambda2)$ is the light absorption coefficient of the second measurement light Lm2 at center wavelength λ2 at position z1. These values are determined by actual measurements.

Thus, by finding the respective light absorption coefficients on the basis of the intensity of the reflected light (backscattered light) of the first measurement light Lm1 and second measurement light Lm2 of center wavelengths λ1 and λ2 respectively in the small region between position z1 and position z2, that is spaced apart from position z1 by Δz (on the order of several tens of μm), that is, the intensity of signal light Ls1 and Ls2, the of the composition and the water of the enamel 1101 can be found.

Here, as mentioned earlier, because water exists (approximately 2%) in a small amount in the composition of the enamel 1101 of a healthy tooth 1100, the abundance ratio of the water found as mentioned above is a measurement result that includes water in the composition of the enamel 1101, but this does not produce a substantial problem.

Figure 20:
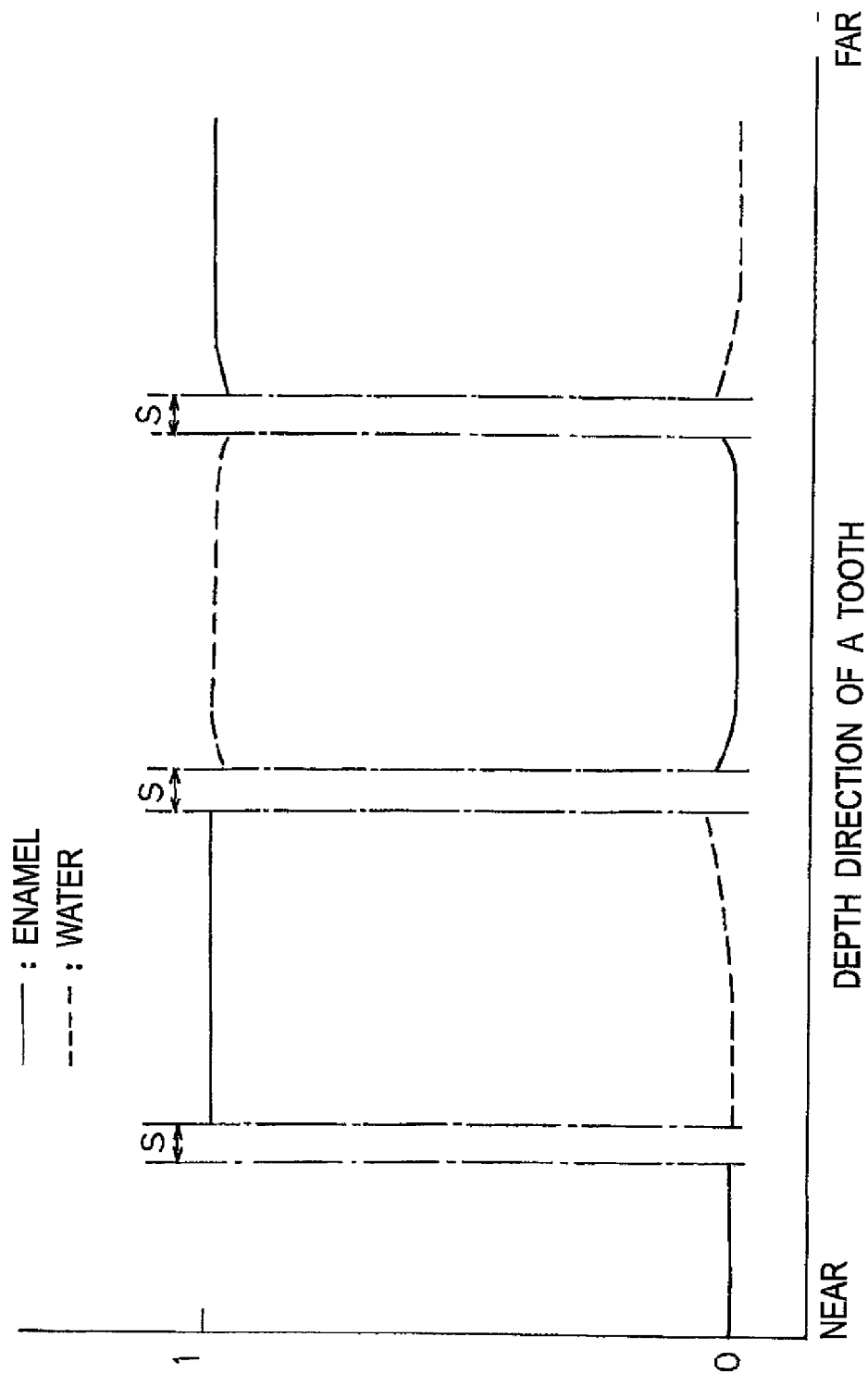
FIG. 20 shows distribution of the proportions of enamel tissue and water in the thickness direction (depth direction) of a tooth.

The distribution of the abundance ratio of the composition of the enamel 1101 and water in the thickness direction (depth direction) of the tooth 1100 found as mentioned hereinabove is shown in FIG. 20. As can be seen from FIG. 20, positions at which the abundance ratio of water is high (approximately 1) are points at which a pit 1102 exists. Further, at S of the surface (interface) of the tooth 1100 and pit 1102 and so forth, strong reflection light (backscattered light) that is produced by Fresnel reflection occurs, the measurement error in the light absorption coefficient is extremely large and, therefore, calculation of the percentage is omitted Thus, the present embodiment focuses on a phenomenon in which a fluid whose main component is water such as saliva invades the interior of the pit 1102 formed in the enamel 1101 of a tooth 1100 with a small amount of water and, by determining the distribution of the abundance ratio of the composition of enamel 1101 and water as mentioned earlier, the characteristics of the tooth 1100 such as the existence of pits 1102 and the size and position thereof are clearly obtained.

Further, by performing a two-dimensional measurement by scanning the incident measurement light Lm (B scan) and, more specifically, moving the measurement light Lm linearly along the surface of the tooth 1100 by sliding and rotating the inner tube 1032 in a circumferential direction with respect to the outer tube 1031 of the probe 1030, for example, a tomogram of the pit 1102 can be obtained. Furthermore, by repeating the two-dimensional measurement while shifting the scanning position a little at a time and displaying the two-dimensional images obtained in parallel, a three-dimensional (solid) tomogram of the pits 1102 can be obtained and characteristics of the tooth 1100 such as the existence of pits 1102 and the size and position thereof can be clearly obtained.

Further, even in the case of an advancing stage of decalcification before pits 1102 are formed in the enamel 1101 of the tooth 1100, because an inorganic component seeps from the enamel 1101 and microscopic gaps are generated in the enamel 1101, water invades the gaps at the molecular level and the amount of water per unit volume in the enamel 1101 rises and, therefore, the gaps can be detected in the same manner as mentioned hereinabove.

Further, by using the measurement light in a shorter wavelength range than 1.2 μm, the characteristics of the tooth 1100 can also be found on the basis of only the abundance per unit volume of the composition of the enamel 1101 without finding the amount of water per unit volume in the enamel 1101 of the tooth 1100. However, due to lack of accuracy, it is hardly preferable.

Further, detection can also be performed easily by directly finding the characteristics of the tooth 1100 on the basis of the intensity of the signal light for each wavelength range as shown in FIG. 18 instead of finding the abundance ratio per unit volume of the composition and water in the enamel 1101 of the tooth 1100 as shown in FIG. 20. When such simple detection is performed, it is particularly desirable to obtain data converted to a tomogram by performing the B scan mentioned earlier.

When tomography of the retina of an eye is performed, there is the possibility of adverse effects on the eye and so forth when the intensity of the measurement light is too strong. An OCDR-OCT device, which uses conventional OCDR method, uses an SLD, which is one type of light-emitting diode, for the light source, for which the efficiency of light coupling with the optical fiber is poor and an adequate intensity cannot be obtained for the measurement light. It is difficult to improve the S/N ratio with an SLD. However, because OCT measurements of retina do not require strong light, problems do not arise.

On the other hand, in the case of this embodiment, the wavelength-tunable light generator 1011 can be a semiconductor laser light generator. The efficiency of light coupling of the laser with optical fiber is high and sufficient intensity of the laser can be used as the light source of the measurement light, leading to an improvement of the S/N ratio. With such improved S/N ratio, the detection of the characteristics of the tooth 1100 such as early stage cavities becomes possible even without using the measurement light of a plurality of different wavelength ranges. However, when measurement light of a plurality of different wavelength ranges as described earlier is not used, the accuracy decreases, which is hardly preferable.

Furthermore, the present embodiment described a case where the absorption of measurement light Lm by the tooth 1100 is predominant, the attenuation of the signal light Ls caused by reflection scatter can be ignored, the backscatter efficiency is assumed to be the same in all positions, and the characteristics of the tooth 1100 are determined by using the measurement light Lm1 and Lm2 of the wavelength ranges of two mutually different center wavelengths λ1 and λ2. However, in cases where absorption of the measurement light Lm by elements other the composition and water of the enamel 1101 of the tooth 1100, for example, cannot be ignored, cases where attenuation of the signal light Ls by reflection and scattering cannot be ignored, and cases where the backscattering coefficient varies depending on the position, and so forth, by increasing correspondingly the number of measurement light Lm of wavelength ranges of mutually different center wavelengths λ, the increased number of parameters can be determined.

Moreover, in the present embodiment, the second coupler 1013 and third coupler 1016 were used by using the optical circulator 1015 to construct a Mach-Zehnder-type interferometer. However, main division and combining means, that works both as main dividing means and combining means, can also be used by constructing a Michelson-type interferometer.

Figure 21:
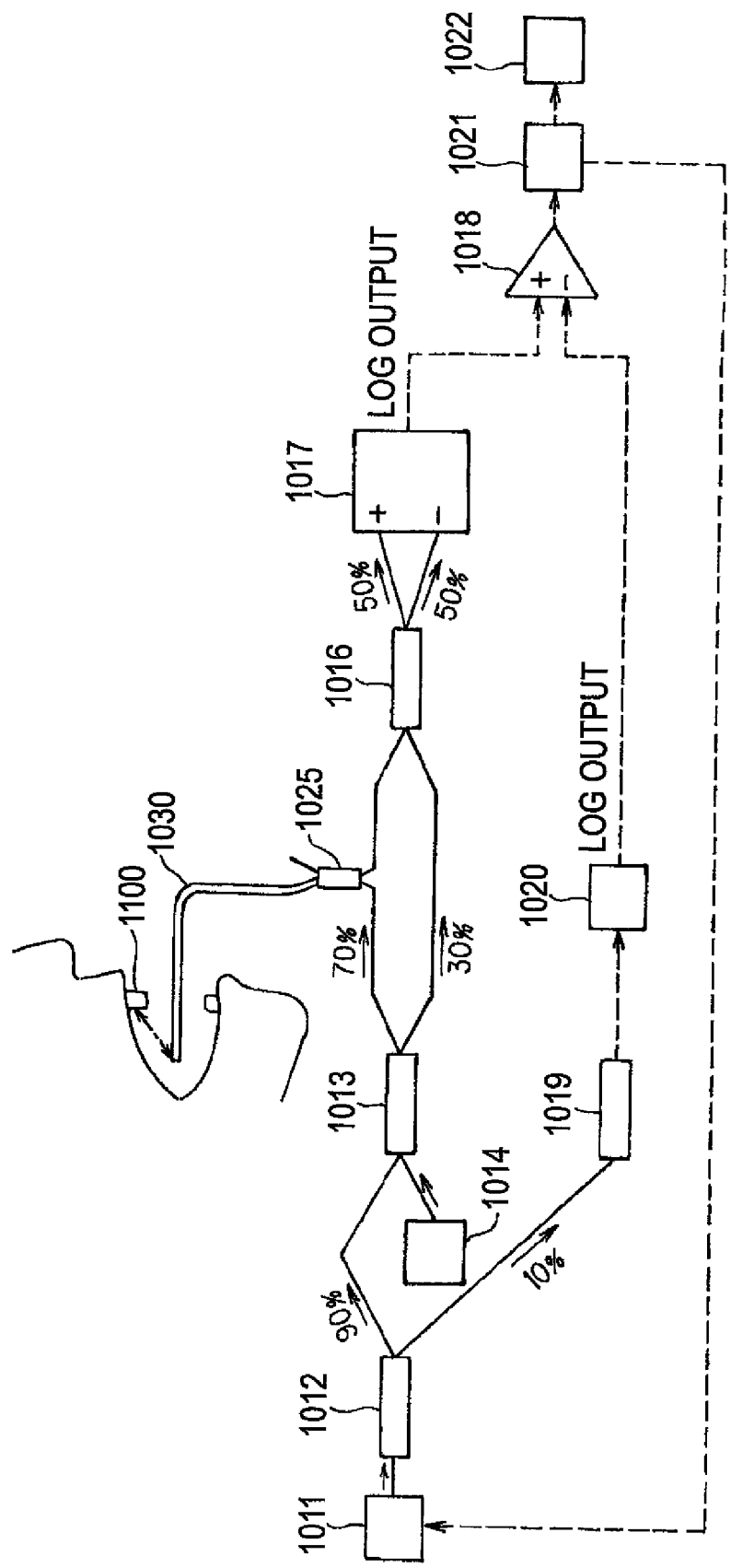
FIG. 21 shows a schematic drawing of another embodiment of the dental OCT device of the present invention.

Further, although the optical circulator 1015 was applied in the present embodiment, when the optical circulator 1015 does not operate with visible light, for example, a coupler 1025 can also be used as shown in FIG. 21, for example, in place of the optical circulator 1015.

Furthermore, in the present embodiment, a probe 1030 that allows guidance for the entry of signal light and guidance for the exit of measurement light to be implemented by means of the same optical fiber 1034 by using the optical circulator 1015 is applied. However, a probe 1030 can also be applied by omitting the optical circulator 1015 and, as shown in FIG. 22, providing two optical fibers 1034A and 1034B in parallel within the inner tube 1032 to guide the exit of measurement light by means of the one optical fiber 1034A and guide the entry of signal light by means of the other optical fiber 1034B, for example.

Here, the optical fibers 1034A and 1034B have optical axes that are slightly shifted with respect to one another and a difference between the optical axes of the emitted measurement light and the incident signal light is produced. However, in practice, there is no particular problem.

<C> Device for Measuring Tomogram of Various Structures such as Biological Body or Coated Surface or the Like (Causes Appearing in Task <C>)

In the actual OCDR-OCT measurement, a reference mirror is moved at speed v. Thereupon, the observation position is a function of time in the relationship x=vt and the signal is denoted by $F_t(t)$ of Equation (33). The ith component constituting the signal oscillates with frequency (Equation 32)

$$2f_{ci}v/C \qquad (43)$$

And the envelope is provided by a Gaussian-type time dependency with the following equation:

(Equation 33)

$$\exp\left[-\left(\frac{2\sqrt{\ln 2}}{\Delta Z_i}\right)^2 (vt)^2\right] \qquad (44)$$

In signal processing that extracts an envelope signal (44) from the signal $F_t(t)$ that varies with time in this manner and obtains the reflectance signal as a function of position x by setting vt=x, the excess signals are removed by a bandpass filter that passes only all frequencies of Equation (43), square-law detection is performed, and only envelope information of Equation (44) is found by using the low pass filter.

If a signal obtained with OCT is shown in logarithmic scale as a function of position x, side lobes appear, and a noise floor is also observed in a position apart from the signal position. This is due to the fact that the spectral shape of the light source used in OCDR-OCT is not completely Gaussian. Therefore, in order to reduce the side lobes and noise floor as much as possible, the OCDR-OCT is desirably a broadband light source with a spectral shape that is as close as possible to a Gaussian. The spectral shape of a combined light source is desirably a Gaussian shape also when the bandwidth is extended by means of the combined light source.

Figure 35:
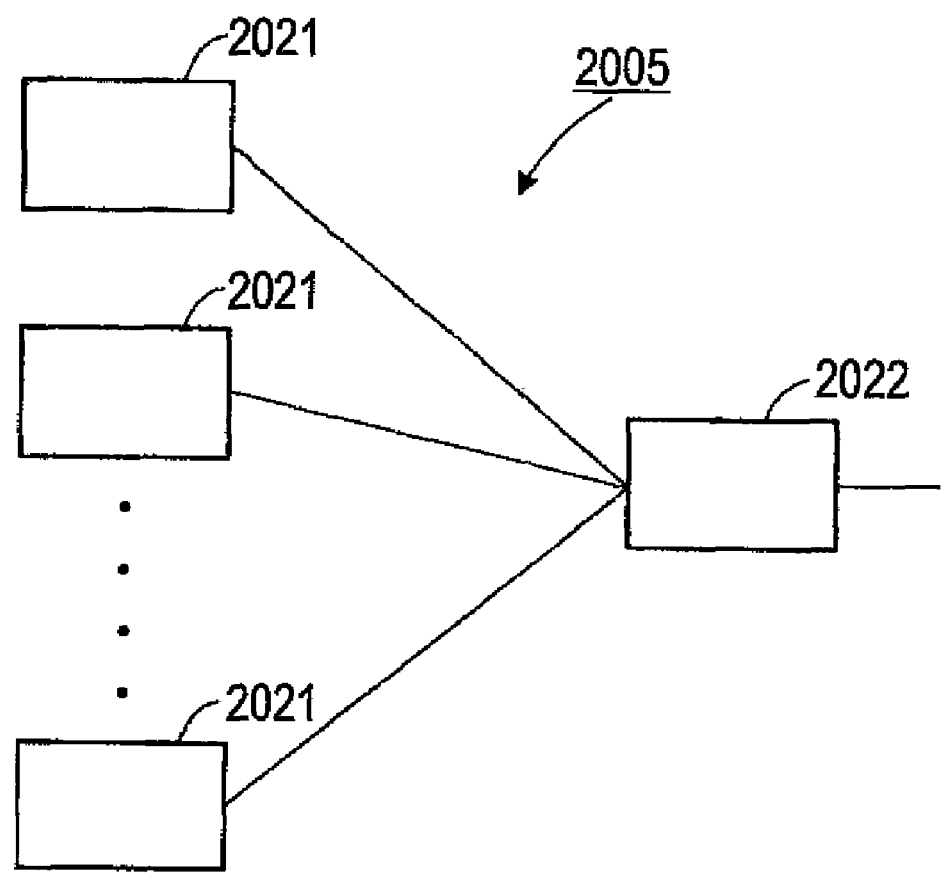
FIG. 35 shows the schematic configuration of a conventional combined light source.
Figure 37:
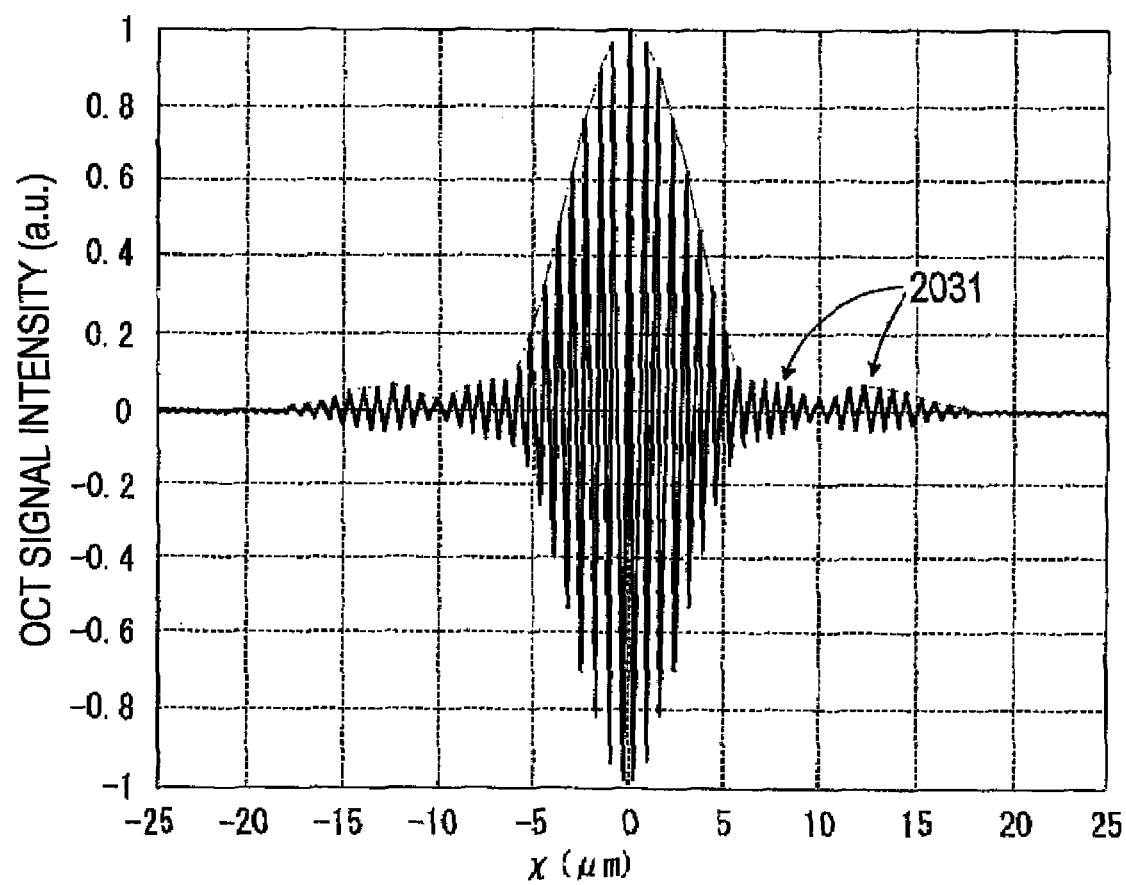
FIG. 37 shows the OCT signal intensity (occurrence of side lobes) when a conventional combined light source is used.
Figure 38:
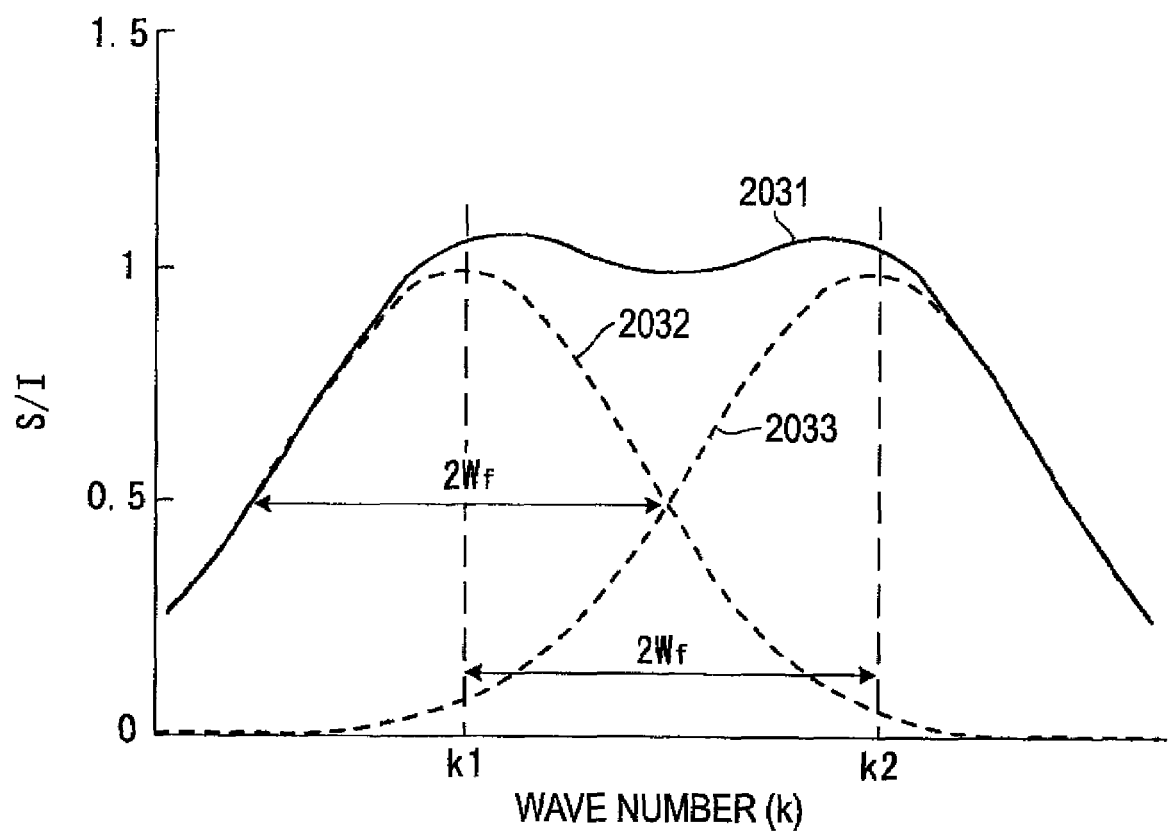
FIG. 38 shows the spectral shape of a conventional combined light source.
Figure 39:
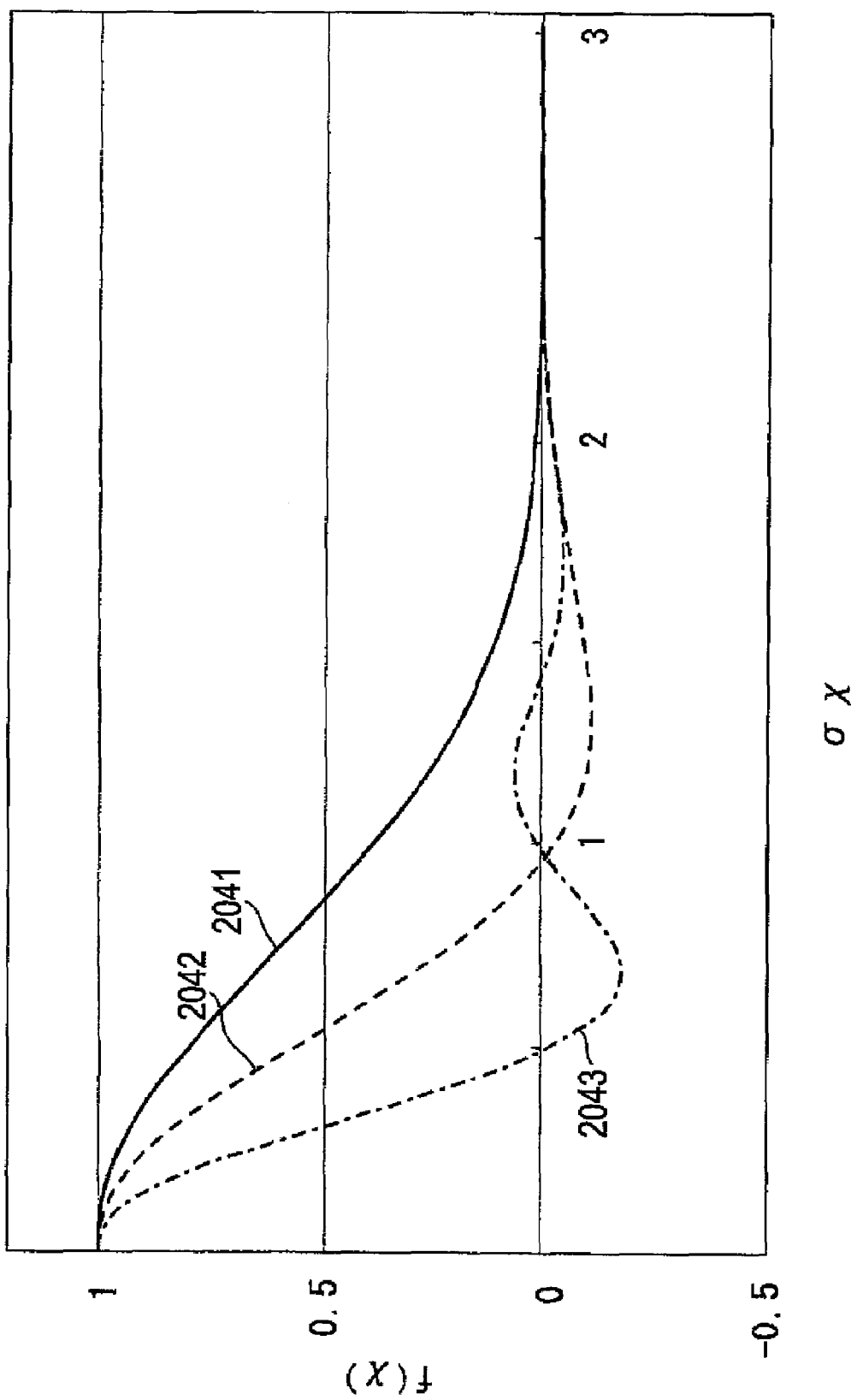
FIG. 39 shows the envelope (right half) of an OCT signal of a conventional combined light source, where the oscillation terms are removed.

In order to obtain a combined light source of OCDR-OCT, in Non-Patent Document 8, a sum of Gaussian light sources of a plurality of different center wavelengths is made as shown in FIG. 35. The spectrum of the light sources in this case form a multi-peak spectral shape comprising a plurality of mountains as shown in Equation (37) and the side lobes appear larger because the spectral shape is not a single-peak Gaussian. This is an unavoidable problem in OCDR-OCT that uses a combined light source to extend the wavelength bandwidth.

Principles of the Invention

The present invention was conceived on the basis of the above idea relating to a combined light source. The present invention shares the idea of enlarging the spectral width by combining a plurality of light sources with a combined light source. However, the present invention differs from the combined light source in that each of the light sources are sequentially used in chronological order instead of the light sources being used after being combined. When such a light source (called 'a switching light source' hereinafter) is used, the relationship between the resolution of the OCT signal and the spectral width of the light source does not change at all when a single light source is used and, therefore, as the spectral width increases when the number of combined light sources increases, the width of the OCT signal narrows in inverse proportion to the spectral width following the combining of the light sources as is the case with a single light source. Moreover, the problem of the increase in the side lobes that accompanies the combination does not arise.

In order to implement such a light source, for the OCT device of the present invention, OFDR-OCT that was invented by the present inventors was chosen instead of OCDR-OCT that is used for a combined light source, a light source constituted to produce a combined output from the outputs of a plurality of wavelength-tunable light sources with different wavelength sweep ranges was used, and wavelength sweeps of the respective wavelength-tunable light sources were performed one by one. Even when the wavelength-tunable light source used was switched, there was no fundamental difference in the spectral shape of the switching light source in a case where there was one wavelength-tunable light source and a case where there was a plurality of wavelength-tunable light sources because there is no difference from a case with one wavelength-tunable light source due to the fact that the intensity of the measurement light of a given wave number can be optionally established by controlling the wavelength-tunable light source. A light spectral as it is intended here is a spectral obtained by means of a wave number sweep of the switching light source and differs from a spectral that is obtained by wavelength-resolving light that is emitted at the same time as per the spectral of a combined light source. Therefore, where the shape of the switching light source is concerned, a spectral of an increased wave number width can be easily implemented in the same way as a case where there is one light source. Hence, the resolution grows narrower in inverse proportion to the wave number width also by widening the bandwidth and the problem of an increase in the side lobes is not produced.

Here, OFDR-OCT will be described in a little detail. In OFDR-OCT, light that is temporarily irradiated onto the sample is constituted by a single wave number component and an OCT signal is combined by subjecting an interference signal obtained by scanning the wave numbers to a Fourier transform (Non-Patent Document 6). To be precise, the sum of the second power of the Fourier cosine transform of the interference signal and the second power of the Fourier sine transform (or square root thereof) is taken.

FIG. 36(b) shows a conceptual view of OFDR-OCT. The difference from the OCDR-OCT method shown in FIG. 36(a) is that the light source in FIG. 36(a) is the broadband light source 2005, whereas the light source in FIG. 36(b) is a very narrowband light source 2131 with wavelength-tunable and the reference mirror 2008 is moved at speed v in FIG. 36(a), whereas the reference mirror 2008 is fixed in FIG. 36(b).

The signal from one reflective face 2003 in FIG. 36(b) that is observed when the wave number of the light source is $k_1$ is given by the following equation.

(Equation 34)

$$P_i(x) = I_o[r_r^2 + r_s^2 + 2\sqrt{r_r r_s} \cos(2k_i x)] \quad (45)$$

Here, $I_0$ is the intensity of the light source and is fixed even when the wave number changes. When differential detection is performed, the DC components of the first and second terms in the square brackets on the right side are neglected and, therefore, the detected signal is only the interference term as per the following equation.

(Equation 35)

$$P_i'(x) = 2\sqrt{r_r r_s} I_o \cos(2k_i x) \quad (46)$$

When the sample is continuous, the reflective face is continuously distributed and, therefore, the intensity $P_i$ of the interference term of the reflected light for $k_i$ from the whole of the sample is integrated for x as per the following equation.

(Equation 36)

$$P_i = 2\sqrt{r_r r_s} I_o \int \cos(2k_i x') dx' \quad (47)$$

The wave numbers $k_i$, i=1 to N, are scanned at equal intervals and the signal R(x) that is proportional to the reflectance at position x in the depth direction of the sample is found by means of the discrete Fourier transform of the following equation:

(Equation 37)

$$R(\chi)^2 = \left[\sum_{i=1}^{N} P_i \cos(2k_i \chi)\right]^2 + \left[\sum_{i=1}^{N} P_i \sin(2k_i \chi)\right]^2 \quad (48)$$

When the spectrum is broadened by means of the switching light source, the number N of the scanned wave numbers increases, the resolution of the spectrum increases, however the side lobes do not increase. An example of a spectrum of the output light of the switching light source is shown in FIG. 29 and an example of an OCT signal that is obtained by using such a light source is shown in FIG. 30 (this graph is for the sum of the second power of the Fourier cosine transform and the second power of the Fourier sine transform).

Figure 29:
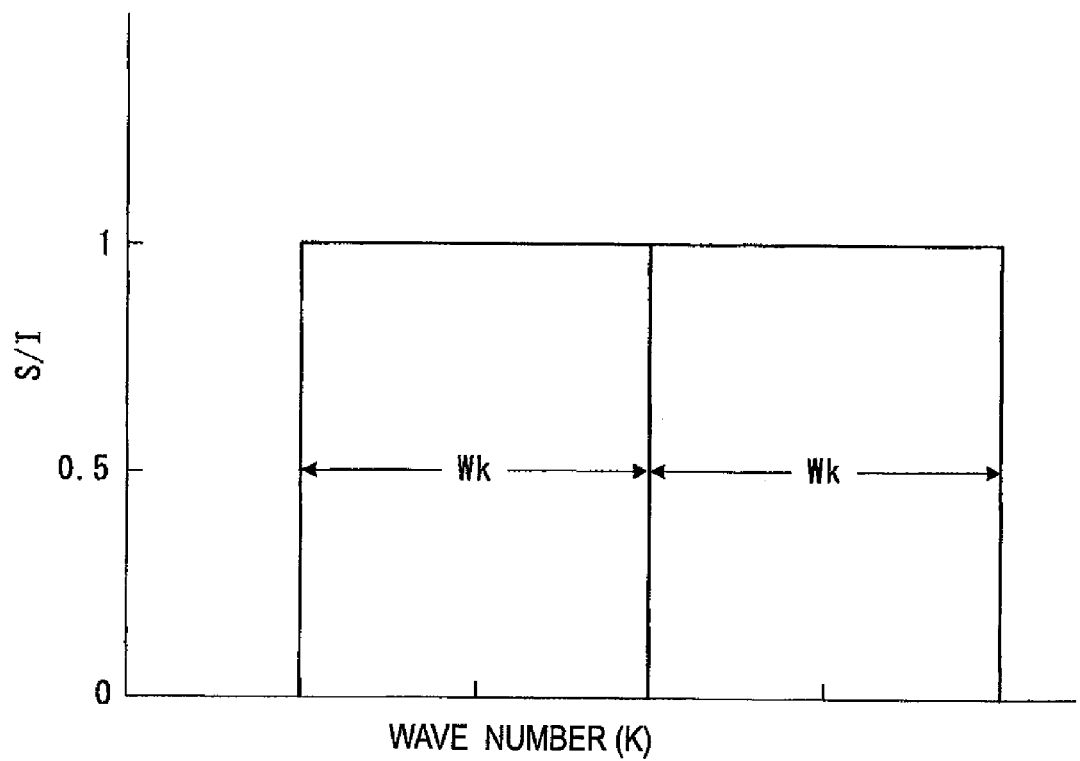
FIG. 29 shows an example of the spectral of the switching light source (wavelength-tunable light generator) of the present invention.
Figure 30:
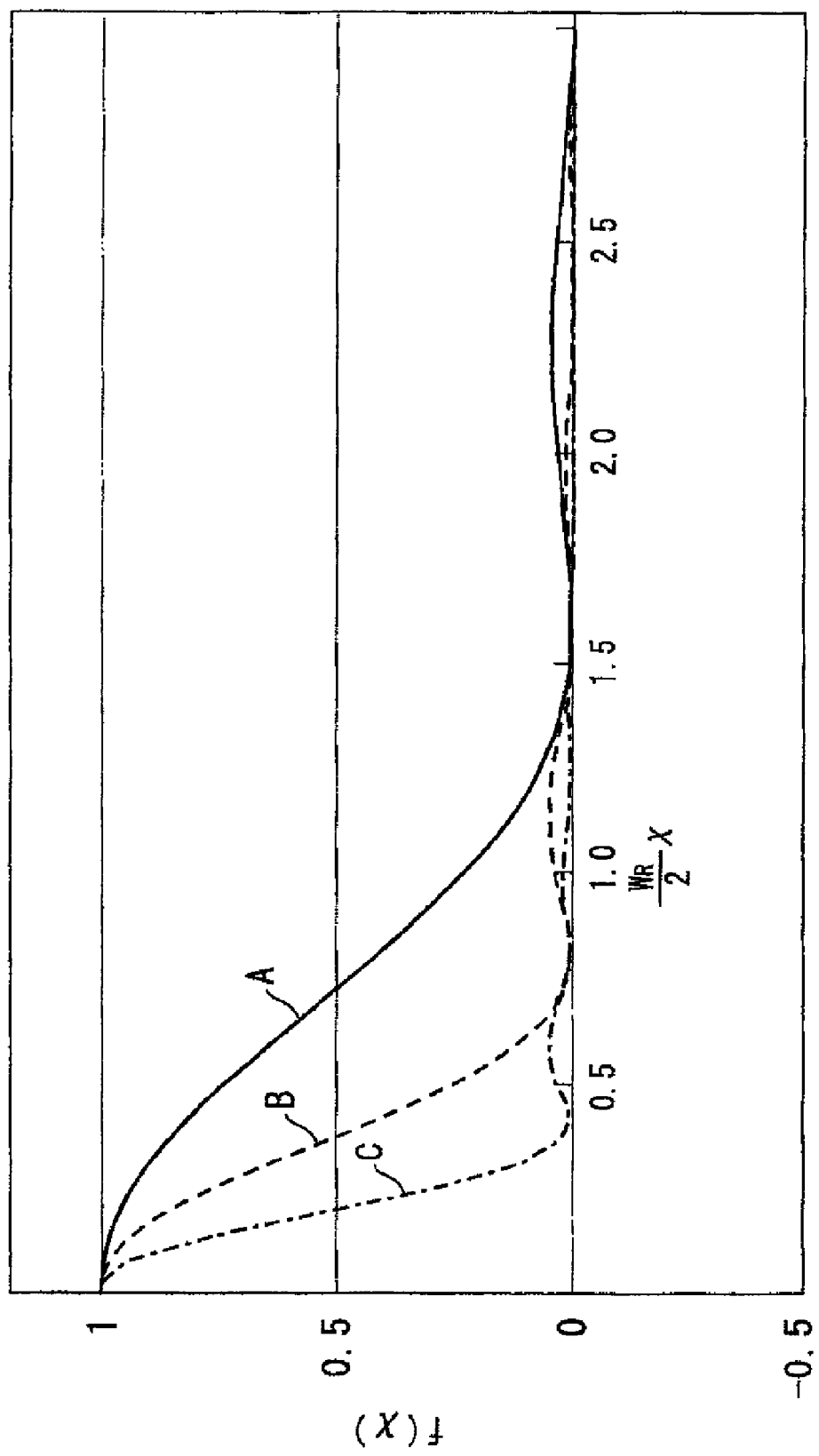
FIG. 30 shows an example of the OCT signal that is obtained by using the switching light source.

FIG. 29 shows a case where two wavelength-tunable light sources with a rectangular spectral shape are combined. The vertical axis in FIG. 30 is normalized by means of the value when x=0. The horizontal axis is normalized by the reciprocal number of the half width at half maximum $W_k/2$ of the spectral. A represents a case where there is one wavelength-tunable light source, B represents a case where there are two wavelength-tunable light sources, and C represents a case where there are four wavelength-tunable light sources (it is assumed that the spectral half width and intensity of each light source are the same and that the total number of swept wave numbers is proportional to the number of light sources). The half widths at half maximum of the OCT peaks become smaller as 0.695, 0.348, and 0.174, inversely proportional to the number of light sources. Because the spectral shape of the light source is rectangular, side lobes are produced but are clearly smaller than those produced by a combined light source and are not large even when the number of light sources increases. Further, the size of the side lobes grows smaller as x increases and the maximum value does not change even when the number of wavelength-tunable light sources is increased.

Figure 31:
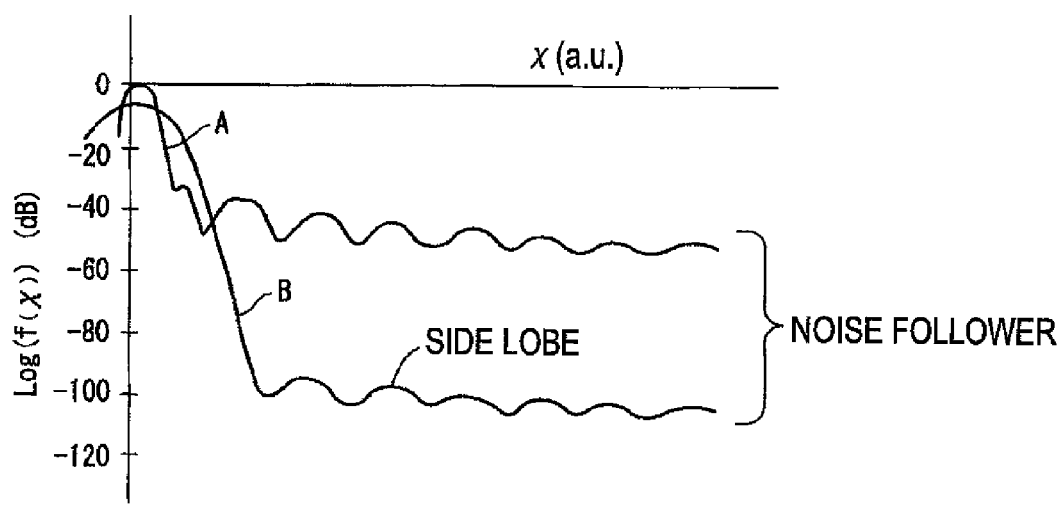
FIG. 31 shows the OCT signal when a Gaussian window is used.

In addition, the side lobes of such Fourier transforms can be removed by performing the Fourier transforms after attaching a suitable window function to the interference signal. FIG. 31 shows the result of a case where a Gaussian window is used. A is an OCT signal when a window function is not used and B is the result when a Gaussian window function is used. The vertical axis represented in logarithmic scale so that small side lobes can also be confirmed. The horizontal axis is in an arbitrary unit. By using a Gaussian window, the side lobes decrease by about −60 dB. If the parameters are suitably adjusted, the side lobes can be decreased still further.

Further, the advantage of FD-OCT that uses a switching light source is that fluctuations in the intensity of the respective wave numbers of each of the light sources can be corrected by means of numerical analysis. When a switching light source with a wide spectral is actually implemented, it is difficult to realize equal intensity for all the wave numbers. Rather, the intensity often fluctuates as a function of the wave number. The intensity for each wave number of the light source is measured during measurement or correction values are found beforehand if the measurements is reproducible and, if each measurement value $P_i$ is multiplied by a correction coefficient $C_i$ (a reciprocal number of the value obtained by measuring the intensity of the output light of the wavelength-tunable light generator each time the wave number is switched or a numerical value proportional to the reciprocal number), the product being equivalent to measured value using a light source of a fixed intensity, the discrete Fourier transform that adopts a window function $W_i$ becomes the following equation, corresponding to=Equation (48):

(Equation 38)

$$R(\chi)^2 = \left[\sum_{i=1}^{N} W_i P_i C_i \cos(2k_i \chi)\right]^2 + \left[\sum_{i=1}^{N} W_i P_i C_i \sin(2k_i \chi)\right]^2. \quad (49)$$

The use of a window function effectively corresponds to use the light source having the same spectral shape with the window function. Multiplying the correction coefficient $C_i$ corresponds to allowing the effective light source spectral shape approach the shape of a window function to the desired shape as close as possible. Thus, the advantage of FD-OCT is also that the overall effective light source spectral shape can be set to the desired function by the numerical calculation, even for the switching light source.

Further, although a case with adjoining spectra of the wavelength-tunable light sources is shown in FIG. 29, there may be intervals between the spectra. The OCT signal, that is obtained in this case is rendered by subtracting the OCT signal obtained by using all the wave numbers that exist in the intervals, from the total OCT signal that is obtained assuming that there is no interval. Therefore, unless the interval is too wide, the OCT signal to be subtracted has a broad and weak peak and modification of the signal is weak.

Figure 32:
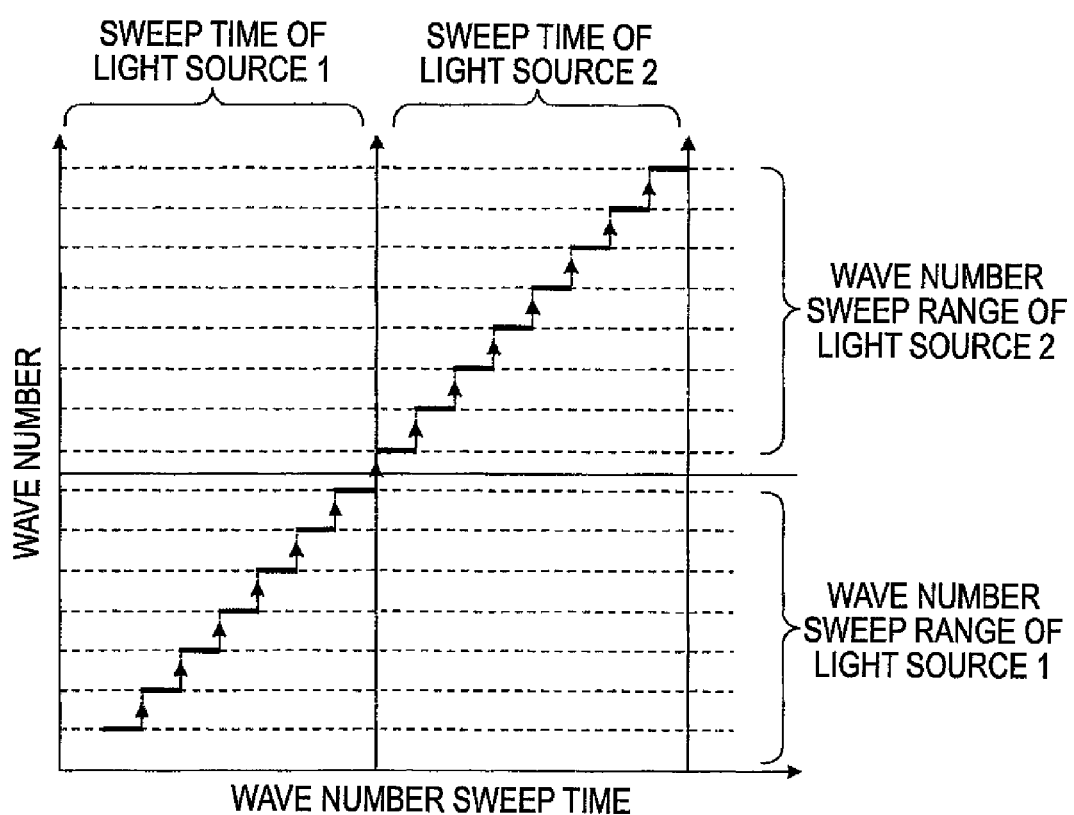
FIG. 32 shows an example of a case where a wave number sweep is performed for mutual compensation of the wave numbers that can be output of the individual wavelength-tunable light sources in the switching light source (wavelength-tunable light generator) of the present invention.

Moreover, in the case of the forty-third invention, there are cases where to extend the wave number range as shown in FIG. 32 (that is, enabling the wave number sweep range exceeds the wave number sweep range of a wavelength-tunable light source). And there are also cases where, as shown in FIG. 34, the wave numbers of two light sources with the same wave number intervals are shifted each other a little so that, when the two light sources are combined and considered as one light source, the resultant wave number interval is narrowed. These cases corresponds to enabling a wave number sweep so that the output wave numbers that can be output supplement one another Examples of wave number scanning methods are shown in FIGS. 32 to 34, where the wavelength-tunable light source allows the wave number to be switched discretely.

In the case of FIG. 32, when the wave number widths of the individual source are restricted, two discrete wavelength-tunable light sources with just adjoining wave number ranges are sequentially scanned and the scanning range is extended. By extending the wave number range, the resolution of the OCT measurement can be increased.

Figure 33:
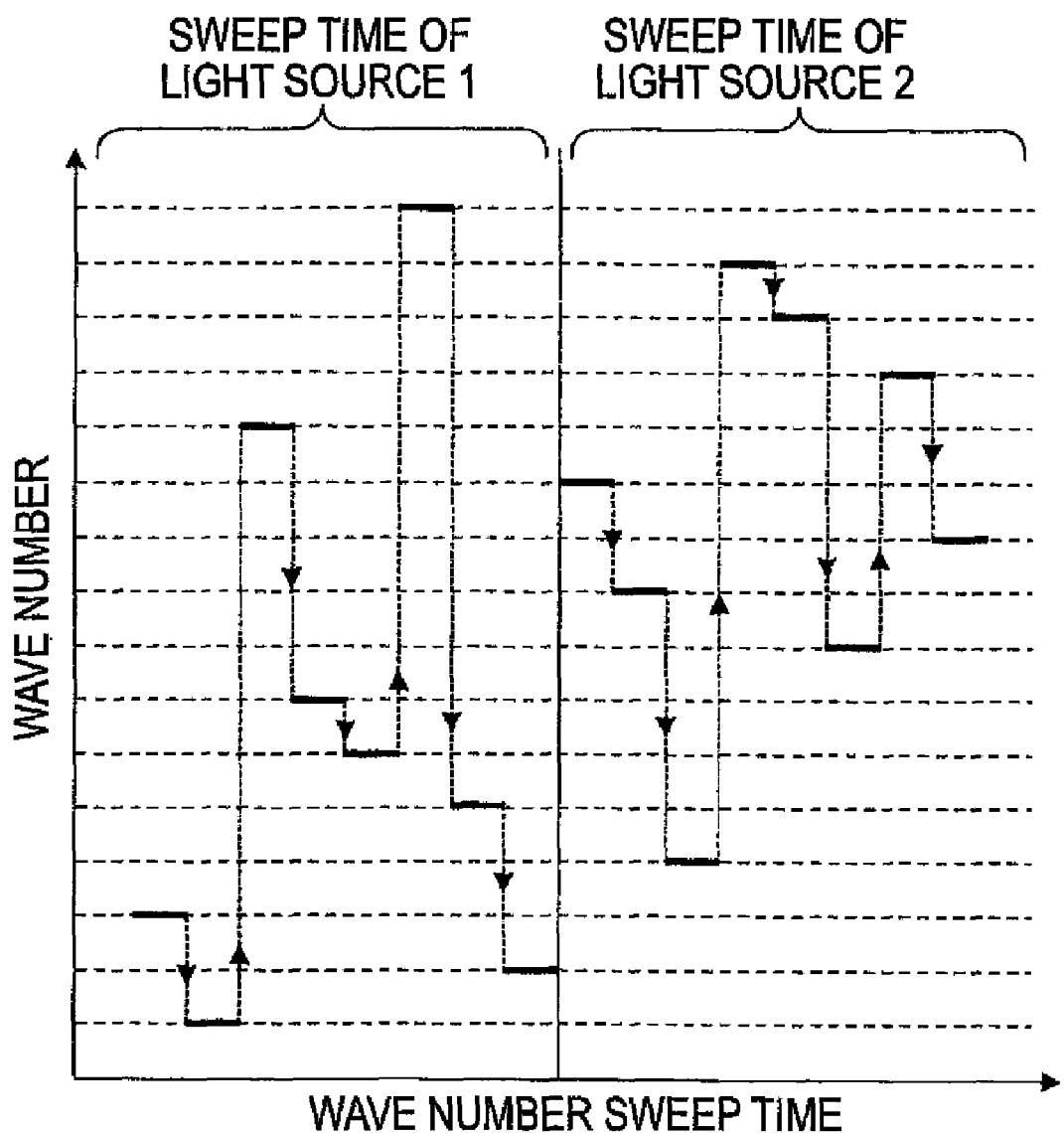
FIG. 33 shows another example of a case where a wave number sweep is performed for mutual compensation of the wave numbers that can be output of the individual wavelength-tunable light sources in the switching light source (wavelength-tunable light generator) of the present invention.
Figure 34:
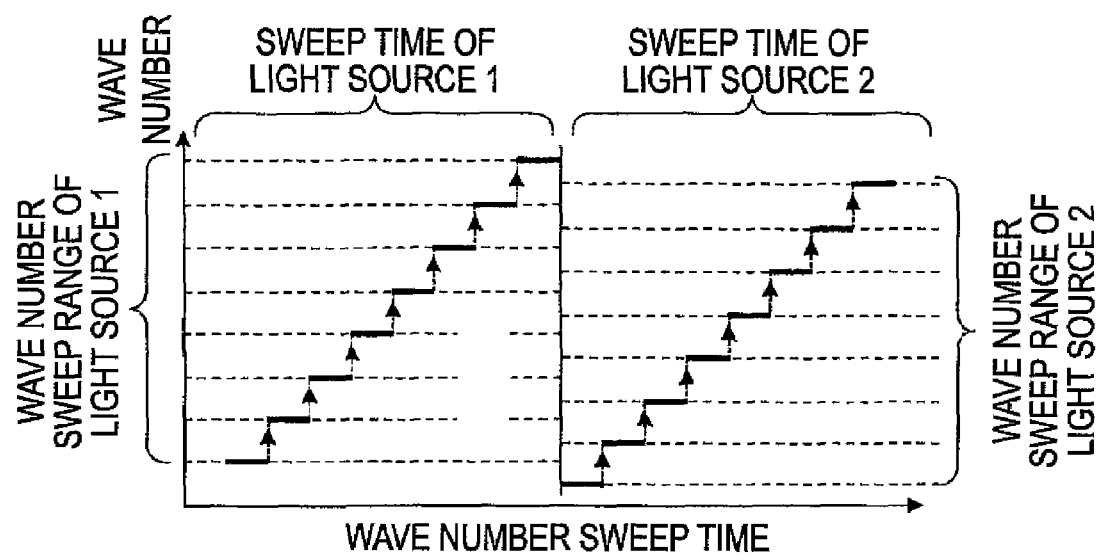
FIG. 34 shows another example of a case where a wave number sweep is performed for mutual compensation of the wave numbers that can be output of the individual wavelength-tunable light sources in the switching light source (wavelength-tunable light generator) of the present invention.

FIG. 33 shows that the wave number scanning need not necessarily increase gradually or decrease gradually and it is sufficient that all the predetermined wave numbers can be scanned in the measurement, even if scanning is irregular. Here, the predetermined wave numbers are desirably a set of wave numbers with equal intervals but are not necessarily restricted to such a set. The predetermined wave numbers may also be a set of wave numbers whose wave number interval is not fixed. When the wave number interval is not fixed, this may also be considered in the calculation process of the tomogram. As a result of being able to perform scanning irregularly, wavelengths that cannot be emitted by a certain light source can be emitted by another light source, whereby a predetermined wave number can be obtained.

FIG. 34 represents a case where the scanning of the wave numbers of the two light sources compliments the wave number intervals each other. The reciprocal number of the wave number interval is proportional to the measurable distance of the sample. Consider the case where the smallest wave number interval is restricted for one particular light source. If another source with the same wave number interval just compliments the wave number interval of the former source, the effective wave number interval is narrowed by the scanning shown in FIG. 34 and the measurable range of the sample can be increased.

Sixth Embodiment

Figure 26:
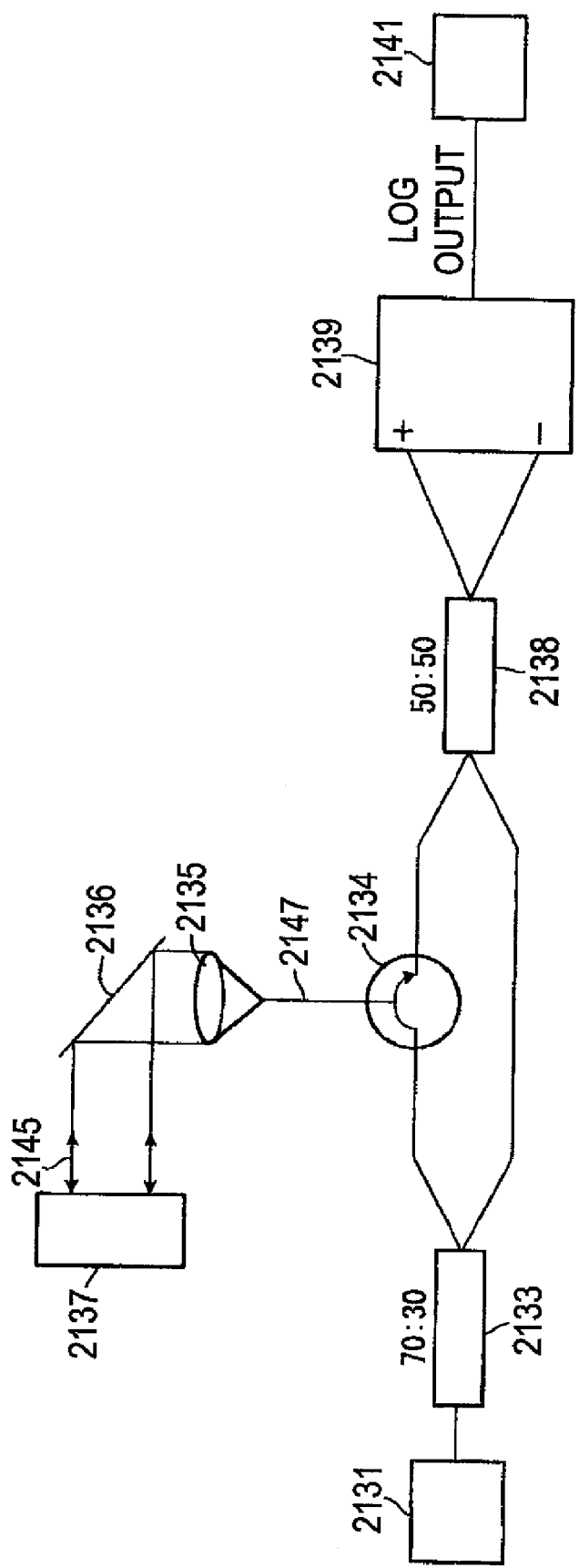
FIG. 26 shows the configuration of an OCT device according to a sixth embodiment of the present invention.

FIG. 26 shows an example of the OCT device of the present invention. Further, FIG. 27 shows the configuration of a wavelength-tunable light generator that is used as the light source of the OCT device, and FIG. 28 shows another configuration of the wavelength-tunable light generator.

The OCT device shown in FIG. 26 uses the switching light source 2131 as the light source (wavelength-tunable light generator) of the OCT device. The switching light source 2131 comprises a light-emitting section 2043 that is constituted to combine and output the outputs of a plurality of wavelength-tunable light sources 2041 of different wave number sweep ranges, and a control device 2044 that permits a wave number sweep in excess of the wave number sweep range of the individual wavelength-tunable light sources by sequentially sweeping the respective wavelength-tunable light sources 2041, as shown in FIG. 27. Further, wave number sweeps are not limited to a sweep in one direction. Wave numbers may be selected irregularly and, finally, the total wave number range may be selected, for example.

Figure 27:
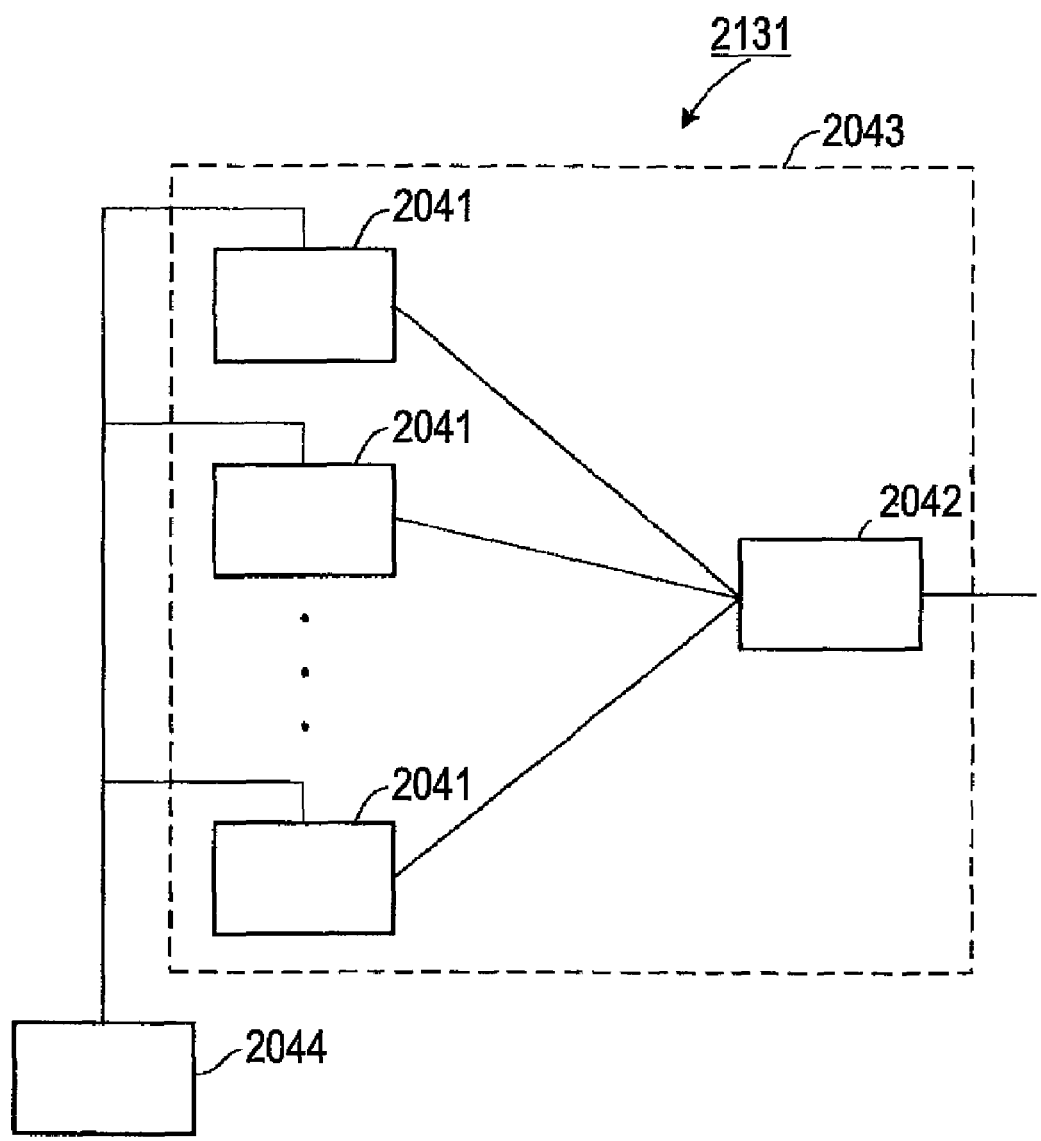
FIG. 27 shows the configuration of a wavelength-tunable light generator that is used as the light source of the OCT device.
Figure 28:
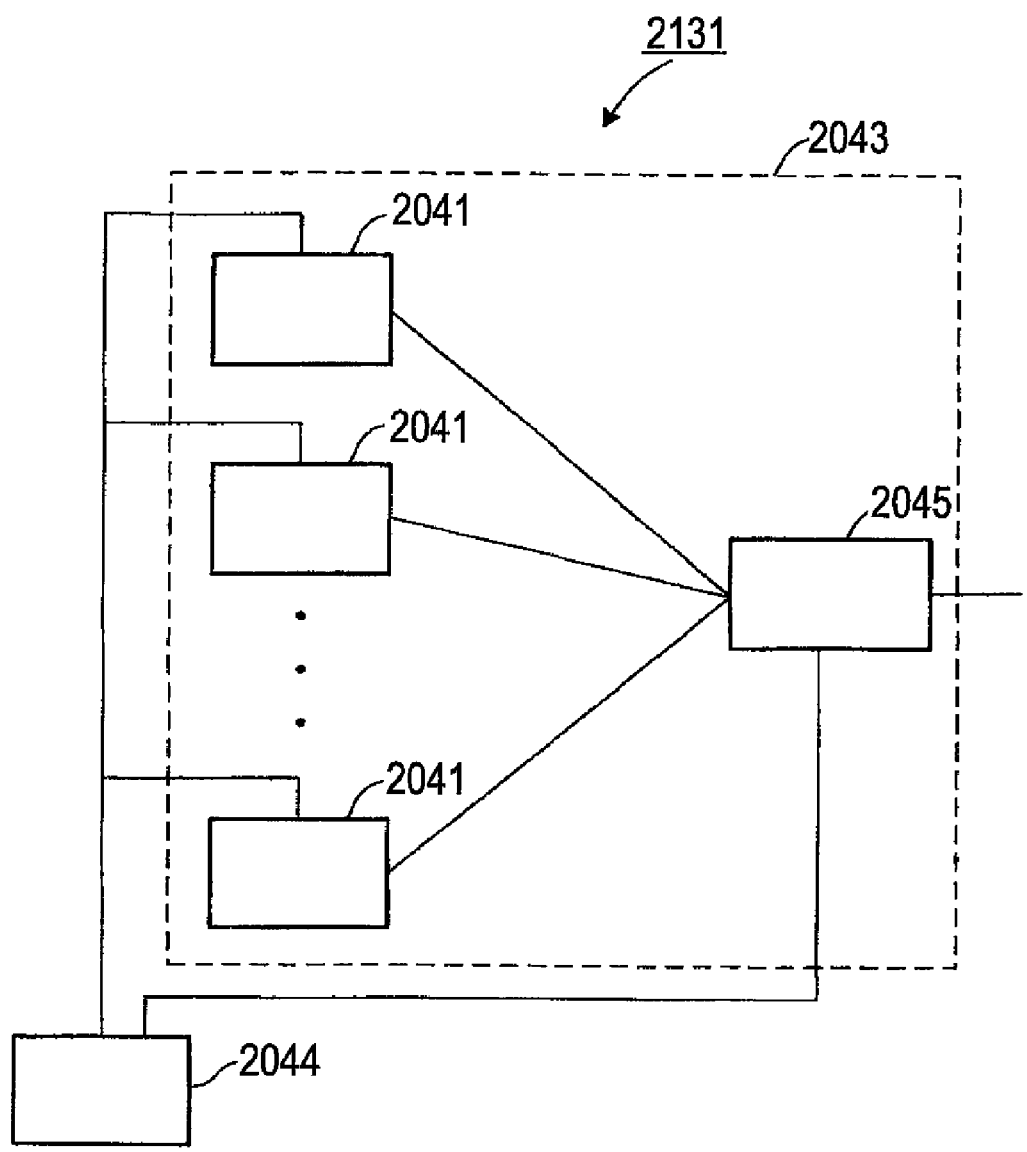
FIG. 28 shows another configuration of the wavelength-tunable light generator that is used as the light source of the OCT device.

The switching light source 2131 may use the optical switch 2045 in FIG. 28 instead of the light coupler 2042 in FIG. 27. Supposing that light of different wavelengths is to be coupled by using a light coupler, a coupling loss is readily produced. However, if the optical switch is mechanical in particular, the coupling loss can theoretically be eliminated. In this case, the control device 2044 controls the optical switch 2045 so that the wavelength-tunable light source 2041 that is undergoing a wave number sweep can be connected to the output side. Further, the switching light source, emitting section 2043 in particular, can be monolithic.

A super structure grating distributed Bragg reflector semiconductor laser (Non-Patent Document 4), for example, can be employed as the wavelength-tunable light source 2041. As the wavelength-tunable range (expressed in wavelengths for the sake of simplicity), four wavelength-tunable light sources 2041 of wavelength-tunable range from 1450 nm to 1490 nm, from 1490 nm to 1530 nm, from 1530 nm to 1570 nm, and from 1570 nm to 1610 nm, for example, are used. Scanning of 1600 wave numbers is performed with equal wave number intervals in these wavelength ranges. A sampled grating distributed Bragg reflector semiconductor laser (SG-DBR laser, U.S. Pat. No. 4,896,325) and a grating coupler sampled reflector laser (GCSR laser) can also be used as the wavelength-tunable light source 2041.

In the OCT device shown in FIG. 26, the light emitted from the switching light source 2131 is divided into two in the percentage 70:30 by a first coupler 2133. Further, one of the divided light components (70% division ratio) is guided to a measurement object 2137 via an optical circulator 2134 as measurement light. Signal light 2145 that is reflected (or backscattered) by the measurement object 2137 re-enters optical fiber 2147 and is guided to a second coupler 2138 by the optical circulator 2134. The signal light and the other light (reference light) that has been divided by the first coupler 2133 are combined by the second coupler 2138. By using the optical circulator 2134, a Mach-Zehnder-type interferometer can be constructed. Further, measurement light that is output from the optical fiber 2147 is irradiated onto the measurement object 2137 after collimated into a narrow parallel beam by a lens 2135.

Although a Mach-Zehnder-type interferometer was used in the above example, a Michelson interferometer (FIG. 36(b)) can also be used. In this case, means for dividing the light emitted by the switching light source 2131 and means for combining the signal light and reference light are the same (the beam splitter 2007, for example). Further, although a case where means for irradiating a measurement object with measurement light and means for collecting the reflected light are the same is exemplified, such means may be separate. For example, instead of the optical devices from the optical circulator 2134 to a scanning mirror 2136 an optical fiber A comprising a lens at the tip that is capable of emitting a parallel beam may be connected to the first coupler 2133 and an optical fiber B with the same structure as optical fiber A and glued in parallel to optical fiber A (the respective lenses thereof are also glued together) may be connected to the second coupler 2138.

The B scan for obtaining a tomogram is implemented by scanning measurement light in a straight line over the surface of the measurement object 2137 by means of the scanning mirror 2136 that is interposed between the optical fiber 2147 and measurement object 2137. The scanning of the wave numbers is known as the 'A scan'. Further, the first coupler 2133 and second coupler 2138 are constituted by a directional coupler. The output of the second coupler 2138 is detected by a differential amplifier 2139 with optical detection function. The DC component in Equation (45) is removed by this detection. The output of the differential amplifier 2139 is input to an analog/digital converter (not shown), the resultant digital output is guided to a data processor 2141 and the interferogram, that is, the backscatter intensity distributions are computed by the data processor 2141 (Patent Document 5 and Non-Patent Document 9). Further, the data processor 2141 also issues a control command for a wave number sweep to the control device 2044 of the switching light source 2131.

With such an FD-OCT device, the full width at half maximum of the OCT signal R(x) obtained by subjecting the interference light to a Fourier transform is expressed by the following equation and, therefore, a resolution of 6.4 µm in the biological body (of refractive index 1.38) can be implemented by using a switching light source in the wave number sweep range from 1450 nm to 1610 nm. In addition, a resolution of 3.0 µm in the biological body (refractive index 1.38) can be implemented by using the switching light source with the wavelength sweep range from 1.30 µm to 1.61 µm rendered by increasing the number of wavelength-tunable light sources.

(Equation 39)
$$\frac{3.79}{W_k} \quad (50)$$

For the resolution, an R(x)² signal is superior to an R(x) signal. The full width at half maximum when R(x)² is used as the signal, is (Equation 40)
$$\frac{2.78}{W_k} \quad (51)$$

and, therefore, for the resolution in the biological body, 4.7 µm can be implemented when a switching light source having a wave number sweep range from 1450 nm to 1610 nm is used and 2.2 µm can be implemented when a switching light source having a wave number sweep range from 1.30 µm to 1.61 µm is used. More precisely, the half width in the biological body is 20 µm with a single light source having a wavelength range of from 1.57 µm to 1.61 µm, 9.9 µm when two light sources are combined (wavelength range is from 1.53 µm to 1.61 µm), 4.7 µm when four light sources are combined (wavelength range is from 1.45 µm to 1.61 µm), and 2.2 µm when eight light sources are combined (wavelength range is from 1.30 µm to 1.61 µm). The size of the side lobes is 0.047 times the size of the main peak irrespective of the number of light sources.

When the wavelength ranges above are replaced with wave number ranges, the followings hold. That is, if the wave number range is at least 0.20 µm (wavelength range of 1530 nm to 1610 nm, for example), at least 0.43 µm (wavelength range of 1450 nm to 1610 nm, for example), and at least 0.93 µm (wavelength range of 1450 to 1610 nm, for example), the respective resolution in the biological body is no more than 9.9 µm, no more than 4.6 µm, and no more than 2.2 µm.

The noise floor also drops at least 40 dB. When a window function is used, it is possible to remove the side lobes and markedly reduce the noise floor. On the other hand, the resolution deteriorates as can also be seen from FIG. 31. Therefore, there is the negative aspect that the required resolution cannot be secured in using a window function in OFDR-OCT that employs a single wavelength-tunable light source. However, when a broadband switching light source is used, there is the advantage that an adequate resolution is obtained even taking the reduction in the resolution caused by the window function into consideration because the original resolution is sufficiently high. Further, in addition to using a Gaussian window as the window function, a Welch window, Parzen window, Hanning window, or a Hamming window, or the like can be used.

On the other hand, in the case of a combined light source (broadband light sources differing only in the center wavelength are combined), the half width in the biological body is 20 µm with a single broadband light source having a wavelength range from 1.57 µm to 1.61 µm, 13 µm when two light sources are combined (wavelength range is from 1.53 µm to 1.61 µm), and 6.7 µm when four light sources are combined (wavelength range is from 1.46 µm to 1.61 µm). The size of the side lobes is 0.27 times the size of the main peak when four light sources are combined.

In the description hereinabove, only the cases using a wavelength-tunable light generator, in which the wave number is switched discretely, was described. However, the wave number may be switched continuously. In this case, the present invention functions as a wavelength-tunable light generator for chirp OCT (See Handbook of Optical Coherence Tomography (Non-Patent Document 3, for example) rather than OFDR-OCT, and effects such as that of increasing the resolution without increasing the side lobes are afforded similarly to those for FD-OCT.

INDUSTRIAL APPLICABILITY

<A> Wavelength-Tunable Light Source Generator and OCT Device

The present invention relates to an OCT wavelength-tunable light source generator and an OCT device and is useful when applied to cases where tomographic observation of an biological body parts that is difficult to constrain, which is a problem for conventional OCT in particular, is performed, and is also useful when applied to cases where tomographic observation of parts that are difficult to constrain is performed.

<B> Dental OCT Wavelength-Tunable Light Generator and Dental OCT Device

The dental OCT wavelength-tunable light generator and dental OCT device of the present invention is used in the precision-instrument manufacturing industry as a result of the production of the dental OCT wavelength-tunable light generator and dental OCT device.

The invention claimed is:

1. A wavelength-tunable light generator for optical coherence tomography, comprising:
   a light-emitting section that combines and outputs the outputs of a plurality of wavelength-tunable light sources of different wave number sweep ranges; and
   a control device that permits a wave number sweep in excess of the wave number sweep range of individual wavelength-tunable light sources by sweeping said wavelength-tunable light sources one at a time, wherein the wave number is changed stepwise.

2. The wavelength-tunable light generator for optical coherence tomography according to claim 1, wherein said light-emitting section comprises an optical switch and said outputs are combined and output by said optical switch.

3. An optical coherence tomography device, comprising:
   a wavelength-tunable light generator;
   means for dividing output light of said wavelength-tunable light generator into measurement light and reference light;
   means for irradiating a measurement object with said measurement light and for collecting signal right produced as a result of said measurement light being reflected or backscattered by said measurement object;
   means for combining said signal light and said reference light;
   means for measuring intensity of the output light combined by said combining means for each wave number of said wavelength-tunable light generator; and
   means for specifying, in a depth direction of said measurement object, a position at which said measurement light is reflected or backscattered by said measurement object and a reflection or backscatter intensity, from a set of intensities of said combined output light measured for each of the wave numbers by said measuring means,
   wherein said wavelength-tunable light generator is the wavelength-tunable light generator according to claim 1.

4. An optical coherence tomography device comprising:
   a wavelength-tunable light generator including
      a light-emitting section that combines and outputs the outputs of a plurality of wavelength-tunable light sources of different wave number sweep ranges, and
      a control device that permits a wave number sweep in excess of the wave number sweep range of individual wavelength-tunable light sources by sweeping said wavelength-tunable light sources one at a time;
   means for dividing output light of said wavelength-tunable fight generator into measurement light and reference light;
   means for irradiating a measurement object with said measurement light and for collecting signal light produced as a result of said measurement light being reflected or backscattered by said measurement object;
   means for combining said signal light and said reference light;
   means for measuring intensity of the output light combined by said combining means for each wave number of said wavelength-tunable light generator; and
   means for specifying, in a depth direction of said measurement object, a position at which said measurement light is reflected or backscattered by said measurement object and a reflection or backscatter intensity, from a set of intensities of said combined output light measured for each of the wave numbers by said measuring means,
   wherein said specifying means subjects a combination of real numbers comprising said intensity of the output light combined by said combining means and said wave number to a Fourier transform,
   wherein said specifying means corrects said intensity of the output light combined by said combining means so as to eliminate the effect of fluctuations in the intensity with respect to the wave number of the output light of said wavelength-tunable light generator, and
   wherein said correction is performed by multiplying a reciprocal number of a value that is obtained by sequentially measuring the intensity of the output light of said wavelength-tunable light generator each time said wave number is changed during the measurement by said optical coherence tomography device, or a numerical value that is proportional to said reciprocal number, by said intensity of the output light combined by said combining means.

5. An optical coherence tomography device comprising:
   a wavelength-tunable light generator including
      a light-emitting section that combines and outputs the outputs of a plurality of wavelength-tunable light sources of different wave number sweep ranges, and
      a control device that permits a wave number sweep in excess of the wave number sweep range of individual wavelength-tunable light sources by sweeping said wavelength-tunable light sources one at a time;
   means for dividing output light of said wavelength-tunable light generator into measurement light and reference light;
   means for irradiating a measurement object with said measurement light and for collecting signal light produced as a result of said measurement light being reflected or backscattered by said measurement object;
   means for combining said signal light and said reference light;
   means for measuring intensity of the output light combined by said combining means for each wave number of said wavelength-tunable light generator; and
   means for specifying, in a depth direction of said measurement object, a position at which said measurement light is reflected or backscattered by said measurement object and a reflection or backscatter intensity, from a set of intensities of said combined output light measured for each of the wave numbers by said measuring means,
   wherein said specifying means subjects a combination of real numbers comprising said intensity of the output light combined by said combining means and said wave number to a Fourier transform,
   wherein said specifying means corrects said intensity of the output light combined by said combining means so as to eliminate the effect of fluctuations in the intensity with respect to the wave number of the output light of said wavelength-tunable light generator, and
   wherein said correction is performed by multiplying a reciprocal number of a value that is obtained by pre-measuring, for each of said wave numbers, the intensity of the output light of said wavelength-tunable light generator, or a numerical value that is proportional to said reciprocal number, by the intensity of said combined output light.

6. A wavelength-tunable light generator for optical coherence tomography, comprising:
   a light-emitting section that combines and outputs the outputs of a plurality of wavelength-tunable light sources of different wave number sweep ranges; and
   a control device that permits a wave number sweep in excess of the wave number sweep range of the individual wavelength-tunable light sources, wherein the wave number changes stepwise; and wherein the outputs of said wavelength-tunable light sources are sequentially output in chronological order.

7. The wavelength-tunable light generator for optical coherence tomography according to claim 6, wherein said light-emitting section comprises an optical switch and said outputs are combined and output by said optical switch.

8. An optical coherence tomography device, comprising:
a wavelength-tunable light generator;
means for dividing output light of said wavelength-tunable light generator into measurement light and reference light;
means for irradiating a measurement object with said measurement light and for collecting signal light produced as a result of said measurement light being reflected or backscattered by said measurement object;
means for combining said signal light and said reference light;
means for measuring intensity of the output light combined by said combining means for each wave number of said wavelength-tunable light generator; and
means for specifying, in a depth direction of said measurement object, a position at which said measurement light is reflected or backscattered by said measurement object and a reflection or backscatter intensity, from a set of intensities of said combined output light measured for each of the wave numbers by said measuring means,
wherein said wavelength-tunable light generator is the wavelength-tunable light generator according to claim 6.

9. An optical coherence tomography device, comprising:
a wavelength-tunable light generator including
a light-emitting section that combines and outputs the outputs of a plurality of wavelength-tunable light sources of different wave number sweep ranges, and
a control device that permits a wave number sweep in excess of the wave number sweep range of individual wavelength-tunable light sources,
wherein the outputs of said wavelength-tunable light sources are sequentially output in chronological order;
means for dividing output light of said wavelength-tunable light generator into measurement light and reference light;
means for irradiating a measurement object with said measurement light and for collecting signal light produced as a result of said measurement light being reflected or backscattered by said measurement object;
means for combining said signal light and said reference light;
means for measuring intensity of the output light combined by said combining means for each wave number of said wavelength-tunable light generator; and
means for specifying, in a depth direction of said measurement object, a position at which said measurement light is reflected or backscattered by said measurement object and a reflection or backscatter intensity, from a set of intensities of said combined output light measured for each of the wave numbers by said measuring means,
wherein said specifying means subjects a combination of real numbers comprising said intensity of the output light combined by said combining means and said wave number to a Fourier transform,
wherein said specifying means corrects said intensity of the output light combined by said combining means so as to eliminate the effect of fluctuations in the intensity with respect to the wave number of the output light of said wavelength-tunable light generator, and
wherein said correction is performed by multiplying a reciprocal number of a value that is obtained by sequentially measuring the intensity of the output light of said wavelength-tunable light generator each time said wave number is changed during the measurement by said optical coherence tomography device, or a numerical value that is proportional to said reciprocal number, by said intensity of the output light combined by said combining means.

10. An optical coherence tomography device, comprising:
a wavelength-tunable light generator including
a light-emitting section that combines and outputs the outputs of a plurality of wavelength-tunable light sources of different wave number sweep ranges, and
a control device that permits a wave number sweep in excess of the wave number sweep range of individual wavelength-tunable light sources,
wherein the outputs of said wavelength-tunable light sources are sequentially output in chronological order;
means for dividing output light of said wavelength-tunable light generator into measurement light and reference light;
means for irradiating a measurement object with said measurement light and for collecting signal light produced as a result of said measurement light being reflected or backscattered by said measurement object;
means for combining said signal light and said reference light;
means for measuring intensity of the output light combined by said combining means for each wave number of said wavelength-tunable light generator; and
means for specifying, in a depth direction of said measurement object, a position at which said measurement light is reflected or backscattered by said measurement object and a reflection or backscatter intensity, from a set of intensities of said combined output light measured for each of the wave numbers by said measuring means,
wherein said specifying means subjects a combination of real numbers comprising said intensity of the output light combined by said combining means and said wave number to a Fourier transform,
wherein said specifying means corrects said intensity of the output light combined by said combining means so as to eliminate the effect of fluctuations in the intensity with respect to the wave number of the output light of said wavelength-tunable light generator, and
wherein said correction is performed by multiplying a reciprocal number of a value that is obtained by pre-measuring, for each of said wave numbers, the intensity of the output light of said wavelength-tunable light generator, or a numerical value that is proportional to said reciprocal number, by the intensity of said combined output light.

* * * * *

UNITED STATES PATENT AND TRADEMARK OFFICE
CERTIFICATE OF CORRECTION

| | | |
|---|---|---|
| PATENT NO. | : 7,732,784 B2 | |
| APPLICATION NO. | : 11/867732 | |
| DATED | : June 8, 2010 | |
| INVENTOR(S) | : Kimiya Shimizu et al. | |

It is certified that error appears in the above-identified patent and that said Letters Patent is hereby corrected as shown below:

Include the second Assignee on the Title page, should read as follows:

(73) Assignee: School Juridical Person Kitasato Institute, Tokyo (JP)
                  Nippon Telegraph and Telephone Corporation, Tokyo (JP)

Signed and Sealed this

Twenty-third Day of November, 2010

David J. Kappos
*Director of the United States Patent and Trademark Office*